(12) United States Patent
Nagase et al.

(10) Patent No.: US 8,367,698 B2
(45) Date of Patent: Feb. 5, 2013

(54) 3-SUBSTITUTED SULFONYL PIPERIDINE DERIVATIVE

(75) Inventors: Tsuyoshi Nagase, Tokushima (JP); Takahide Sasaki, Kawasaki (JP); Toshiyuki Takahashi, Tsukuba (JP)

(73) Assignee: MSD K.K., Tokyo (JP)

( * ) Notice: Subject to any disclaimer, the term of this patent is extended or adjusted under 35 U.S.C. 154(b) by 0 days.

(21) Appl. No.: 13/478,680

(22) Filed: May 23, 2012

(65) Prior Publication Data

US 2012/0232109 A1 Sep. 13, 2012

Related U.S. Application Data

(62) Division of application No. 12/865,878, filed as application No. PCT/JP2009/051852 on Feb. 4, 2009, now Pat. No. 8,188,280.

(30) Foreign Application Priority Data

Feb. 6, 2008 (JP) .................................. 2008-25900

(51) Int. Cl.
| A61K 31/439 | (2006.01) |
| A61K 31/444 | (2006.01) |
| A61K 31/4545 | (2006.01) |
| A61K 31/454 | (2006.01) |
| C07D 471/08 | (2006.01) |
| C07D 401/12 | (2006.01) |
| C07D 211/96 | (2006.01) |

(52) U.S. Cl. ........ 514/304; 546/112; 546/194; 546/210; 546/234; 546/125; 514/299; 514/318; 514/326; 514/331

(58) Field of Classification Search ........................ None
See application file for complete search history.

(56) References Cited

U.S. PATENT DOCUMENTS

| 7,491,381 B2 | 2/2009 | Kotani et al. |
| 2005/0043347 A1 | 2/2005 | Betschmann et al. |
| 2006/0122197 A1* | 6/2006 | Yao et al. ..................... 514/256 |

FOREIGN PATENT DOCUMENTS

| WO | 03/028459 A1 | 4/2003 |
| WO | 2005/020598 A2 | 2/2006 |
| WO | 2006/020598 A3 | 2/2006 |
| WO | 2006/094633 A1 | 9/2006 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Kulkarni, S. S. et al., "Design and synthesis of noncompetitive metabotropic glutamate receptor subtype 5 antagonists", Bioorgainic & Medicinal Chemistry Letter, 2006, pp. 3371-3375, vol. 16.
Lee, S. H. et al., "Fatty Acid Synthesis by Elongases in Trypanosomes", Cell, 2006, pp. 691-699, vol. 125.
Matsuzaka, T. et al., "Cloning and characterization of a mamalian fatty acyl-CoA elongase as a lipogenic enzyme regulated by SREBPs", Journal of Lipid Research, 2002, pp. 911-920, vol. 43.
Matsuzaka, T. et al., "Crucial role of a long-chain fatty acid elongase, Elovl6, in obesity-induced insulin resistance", Nature Medicine, 2007, pp. 1193-1202, vol. 13, No. 10.
Moon Y. et al., "Identification of a Mammalian Long Chain Fatty Acyl Elongase Regulated by Sterol Regulatory Element-binding Proteins", The Journal of Biological Chemistry, 2001, pp. 45358-45366, vol. 276, No. 48.
Solovev. M. Y. et al., "Synthesis structure, and properties of a number of 3-sulfanilamidic derivatives of pyridine", Khimiya I Khimicheskaya Tekhnologiya, 2004, pp. 28-36, vol. 47, No. 2.

* cited by examiner

Primary Examiner — Dennis Heyer
(74) Attorney, Agent, or Firm — Janet E. Fair; Todaro C. Todaro

(57) ABSTRACT

[Problem] There is provided a compound useful as a preventive or remedy for cardiovascular disease, neurologic disease, metabolic disease, reproductive disease, and digestive disease.
[Means for Resolution] A compound or a pharmaceutically acceptable salt thereof represented by the following Formula (I)

[Chemical Formula 1]

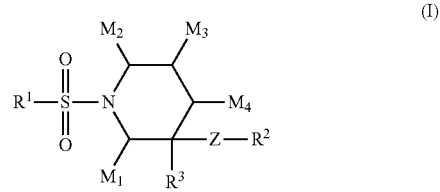

(I)

wherein Z represents

[Chemical Formula 2]

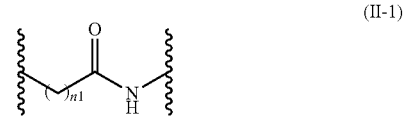

(II-1)

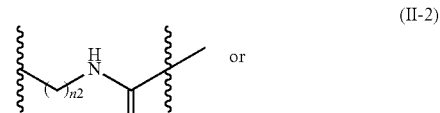

(II-2)

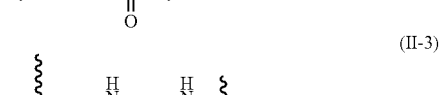

(II-3)

wherein n1, n2, and n3 are 0, 1, or 2, respectively; $R^1$ represents $C_{1-6}$ alkyl, $C_{3-8}$ cycloalkyl, or the like; $R^2$ represents aryl or heteroaryl; $R^3$ represents a hydrogen atom, $C_{1-6}$ alkyl, or the like; and $M_1$, $M_2$, $M_3$, and $M_4$ independently represent a hydrogen atom, $C_{1-6}$ alkyl, or the like, or $M_1$, together with $M_2$, $M_3$, or $M_4$, forms —$CH_2$— or the like.

11 Claims, No Drawings

3-SUBSTITUTED SULFONYL PIPERIDINE DERIVATIVE

CROSS-REFERENCE TO RELATED APPLICATIONS

This application is a divisional of U.S. patent application Ser. No. 12/865,878 now U.S. Pat. No. 8,188,280 which is a U.S. National Phase application under 35 U.S.C. §371 of PCT Application No. PCT/JP2009/051852, filed Feb. 4, 2009, which published as WO 2009/099086 A1 on Aug. 13, 2009, and claims priority under 35 U.S.C. §365(b) from Japanese patent application No. JP2008-025900, filed Feb. 6, 2008.

TECHNICAL FIELD

The present invention is useful in the field of medicine. Specifically, a 3-substituted sulfonylpiperidine derivative of the present invention serves as an inhibitor of long chain fatty acyl elongase (hereinafter, also referred to as "LCE"), and is useful as a remedy for a variety of diseases such as cardiovascular disease, neurologic disease, metabolic disease, reproductive disease, digestive disease, neoplasm, and infection. The invention is also useful as a herbicide.

BACKGROUND ART

Obesity is a condition characterized by accumulation of neutral fat in the fat cell after a sustained state of excessive caloric intake over consumed calories, manifested as a notably higher body weight than the standard body weight (Eiji Itagaki, *STEP Taisha•Naibunpi*, Kaibashobo Inc., 1st Ed., 1998, p. 105). The excess fat accumulation causes diseases, for example, such as insulin resistance, diabetes mellitus, hypertension, and hyperlipidemia. Combined, these factors are known to significantly increase the risk of atherosclerosis onset, and the term "metabolic syndrome" has been used to describe cases associated with such risk factors. Further, neutral fat hyperlipaemia or obesity is known to increase the risk of onset of diseases, for example, such as pancreatitis, liver dysfunction, cancers (including breast cancer, uterine cancer, ovarian cancer, colon cancer, and prostate cancer), emmeniopathy, arthritis, gout, cholecystitis, gastroesophageal reflux, obesity-hypoventilation syndrome (Pickwickian syndrome), and sleep apnea. It is widely known that diabetes often leads to, onset of, for example, such as angina, heart failure, stroke, claudication, retinopathy, failing vision, kidney failure, neuropathy, skin ulcer, and infection [*The Merck Manual of Medical Information*, 2nd Home Edition, Merck & Co., 2003].

LCE, present in the endoplasmic reticulum of the cell, is a member of enzymes that catalyze the carbon chain elongation reaction of fatty acids having carbon chains of 12 or more carbon atoms, catalyzing the rate-limiting condensation step. In mammals, many of the fatty acids that are synthesized de novo in the body possess chain lengths of 16 to 18 carbon atoms. These long chain fatty acids constitute more than 90% of all fatty acids present in cells. They are important components of cell membranes, and represent the major components of fat tissues, the largest energy storage reservoir in animals. The highest rate of de novo fatty acid synthesis occurs in liver, converting excess glucose in the body into fatty acids. Glycolysis converts glucose into pyruvate, which is converted to citrate in the mitochondria and transported to the cytosol. Cytosolic ATP citrate lyase generates acetyl-CoA, the precursor of fatty acids and cholesterol. Acetyl-CoA is carboxylated by acetyl-CoA carboxylase (ACC) to form malonyl-CoA. The multifunction enzyme fatty acid synthase (FAS) uses malonyl-CoA, acetyl-CoA, and NADPH to elongate fatty acids in 2-carbon increments. The principal end product of FAS in rodents is palmitoyl-CoA, which has a carbon chain of 16 carbon atoms. LCE elongates the carbon chain of palmitoyl-CoA in 2-carbon increments [*The Journal of Biological Chemistry*, 276(48), 45358-45366, (2001)]. It is known that an excess fatty acid synthesis in the body increases neutral or other fats, causing fat accumulation. For example, a direct association between LCE and obesity is indicated in WO2005/005665 (Patent Document 1). There is also a report that feeding varies the expression level of mouse FACE (LCE) (Matsuzaka T. et al., *J. Lipid Res.*, 43(6):911-920 (2002); Non-Patent Document 1).

LCE is also present in protozoa and nematodes, and its involvement in the proliferation of cells is known. For example, there has been a report that *Trypanosoma*, a protozoon that causes African trypanosomiasis (more commonly, African sleeping sickness), uses a fatty acid elongation pathway with LCE to synthesize long chain fatty acids, and that the inhibition of the fatty acid elongation reaction in the cell affects the growth of *Trypanosoma*(Lee S. H. et al., *Cell*, 126:691-699 (2006); Non-Patent Document 2).

There has been no compound known to possess an LCE inhibiting effect. The 3-substituted sulfonylpiperidine derivative, a compound of the present invention, has phenyl or heteroaryl at position 3 via an amide bond. To date, no compound has been known that has a specific substituent, such as arylamide or heteroarylamide, at position 3, or that forms an azabicyclo ring instead of a piperidine ring, and has a specific substituent, such as arylamide or heteroarylamide, at position 3.

Patent Document 1: A Pamphlet of International Publication 2005/005665
Non-Patent Document 1: *J. Lipid Res.*, 43(6), 911-920 (2002)
Non-Patent Document 2: *Cell*, 126:691-699 (2006)

DISCLOSURE OF THE INVENTION

Problems that the Invention is to Solve

An object of the present invention is to provide a novel compound having an LCE inhibiting effect.

Means for Solving the Problems

The inventors of the present invention conducted intensive studies, and found that a sulfonylpiperidine derivative having a specific substituent at position 3 of the piperidine skeleton has an excellent LCE inhibiting effect. The present invention was completed based on this finding.

Specifically, the present invention provides;
(1) a compound represented by the following Formula (I) or a pharmaceutically acceptable salt thereof (hereinafter, "compound of the present invention");

[Chemical Formula 1]

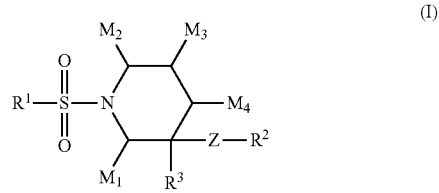

(I)

wherein,

Z is selected from the group consisting of the following Formulae (II-1), (II-2), and (II-3)

[Chemical Formula 2]

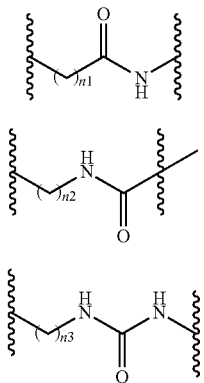

where n1, n2, and n3 are 0, 1, or 2, respectively
wherein, $R^1$ represents $C_{1-6}$ alkyl, $C_{3-8}$ cycloalkyl, aryl, or heteroaryl, wherein the alkyl, cycloalkyl, aryl, or heteroaryl may be substituted with a substituent selected from the group consisting of: hydroxy, cyano, carboxyl, sulfo, halogen, $C_{1-6}$ alkyl, halo $C_{1-6}$ alkyl, $C_{3-8}$ cycloalkyl, $C_{1-6}$ alkoxy, halo $C_{1-6}$ alkoxy, amino (the amino being optionally substituted with 1 to 2 $C_{1-6}$ alkyls, aryls, or heteroaryls), carbamoyl (the carbamoyl being optionally substituted with 1 to 2 $C_{1-6}$ alkyls, aryls, or heteroaryls), sulfanyl (the sulfanyl being optionally substituted with one $C_{1-6}$ alkyl, aryl, or heteroaryl), $C_{1-6}$ alkylsulfinyl, arylsulfinyl, heteroarylsulfinyl, $C_{1-6}$ alkylsulfonyl, arylsulfonyl, heteroarylsulfonyl, sulfamoyl (the sulfamoyl being optionally substituted with 1 to 2 $C_{1-6}$ alkyls, aryls, or heteroaryls), $C_{1-6}$ alkylsulfonylamino, arylsulfonylamino, heteroarylsulfonylamino, $C_{1-6}$ alkylcarbonyl, arylcarbonyl, heteroarylcarbonyl, $C_{1-6}$ alkoxycarbonyl, aryloxycarbonyl, heteroaryloxycarbonyl, carbamoylamino (the carbamoylamino being optionally substituted with 1 to 2 $C_{1-6}$ alkyls, aryls, or heteroaryls), $C_{1-6}$ alkoxycarbonylamino, aryloxycarbonylamino, heteroaryloxycarbonylamino, $C_{1-6}$ alkylcarbonylamino, arylcarbonylamino, heteroarylcarbonylamino, aryl, heteroaryl, aralkyl, heteroaralkyl, aralkyloxy, and heteroaralkyloxy;

$R^2$ represents phenyl or heteroaryl, wherein the phenyl or heteroaryl may be substituted with a substituent selected from the group consisting of: hydroxy, cyano, carboxyl, sulfo, halogen, $C_{1-6}$ alkyl, halo $C_{1-6}$ alkyl, $C_{3-8}$ cycloalkyl, $C_{1-6}$ alkoxy, halo $C_{1-6}$ alkoxy, amino (the amino being optionally substituted with 1 to 2 $C_{1-6}$ alkyls, aryls, or heteroaryls), carbamoyl (the carbamoyl being optionally substituted with 1 to 2 $C_{1-6}$ alkyls, aryls, or heteroaryls), sulfanyl (the sulfanyl being optionally substituted with one $C_{1-6}$ alkyl, aryl, or heteroaryl), $C_{1-6}$ alkylsulfinyl, arylsulfinyl, heteroarylsulfinyl, $C_{1-6}$ alkylsulfonyl, arylsulfonyl, heteroarylsulfonyl, sulfamoyl (the sulfamoyl being optionally substituted with 1 to 2 $C_{1-6}$ alkyls, aryls, or heteroaryls), $C_{1-6}$ alkylsulfonylamino, arylsulfonylamino, heteroarylsulfonylamino, $C_{1-6}$ alkylcarbonyl, arylcarbonyl, heteroarylcarbonyl, $C_{1-6}$ alkoxycarbonyl, aryloxycarbonyl, heteroaryloxycarbonyl, carbamoylamino (the carbamoylamino being optionally substituted with 1 to 2 $C_{1-6}$ alkyls, aryls, or heteroaryls), $C_{1-6}$ alkoxycarbonylamino, aryloxycarbonylamino, heteroaryloxycarbonylamino, $C_{1-6}$ alkylcarbonylamino, arylcarbonylamino, heteroarylcarbonylamino, aryl (the aryl being optionally substituted with $C_{1-6}$ alkoxy), heteroaryl, aryloxy, heteroaryloxy, aralkyl, heteroaralkyl, aralkyloxy, and heteroaralkyloxy;

$R^3$ represents a hydrogen atom, $C_{1-6}$ alkyl, $C_{3-8}$ cycloalkyl, aralkyl, heteroaralkyl, aryl, or heteroaryl, wherein the alkyl, cycloalkyl, aralkyl, heteroaralkyl, aryl, or heteroaryl may be substituted with a substituent selected from the group consisting of halogen, $C_{1-6}$ alkyl, halo $C_{1-6}$ alkyl, $C_{1-6}$ alkoxy, and halo $C_{1-6}$ alkoxy; and $M_1$, $M_2$, $M_3$, and $M_4$ represent each independently a hydrogen atom or $C_{1-6}$ alkyl which may be substituted with halogen; or $M_1$, together with $M_2$, $M_3$ or $M_4$, forms —$CH_2$— or —$CH_2$—$CH_2$—, or $M_4$, together with $M_2$, forms —$CH_2$— or —$CH_2$—$CH_2$—, provided that any two of $M_1$, $M_2$, $M_3$ and $M_4$ together form —$CH_2$— or —$CH_2$—$CH_2$— when $R^3$ is a hydrogen atom.

The present invention further provides:

(2) A long chain fatty acyl elongase (LCE) inhibitor, which contains the compound of Formula (I) or the pharmaceutically acceptable salt thereof as an active ingredient;

(3) A pharmaceutical composition, which contains the compound of Formula (I) or the pharmaceutically acceptable salt thereof; and (4) A preventive or remedy for diabetes mellitus, obesity, or non-alcoholic fatty liver, which contains the compound of Formula (I) or the pharmaceutically acceptable salt thereof as an active ingredient.

A compound of the present invention has an LCE inhibiting effect, and is therefore useful as a preventive or remedy for a variety of diseases involving LCE, for example, such as cardiovascular disease, including, for example, hypertension, angina, heart failure, myocardial infarction, stroke, claudication, diabetic nephropathy, diabetic retinopathy, failing vision, electrolyte abnormalities, and atherosclerosis; central neurologic disease, including, for example, bulimia and diabetic neuropathy; metabolic disease, including, for example, metabolic syndrome, obesity, diabetes mellitus, insulin resistance, hyperlipidemia, hypercholesteremia, neutral fat hyperlipaemia, dyslipidemia, non-alcoholic fatty liver, abnormal hormone secretion, gout, and fatty liver; reproductive disease, including, for example, menstrual disturbance and sexual dysfunction; digestive disease, including liver dysfunction, pancreatitis, cholecystitis, and gastroesophageal reflux; respiratory disease, including obesity-hypoventilation syndrome (Pickwickian syndrome), and sleep apnea; bacterial, fungal, or parasitic infectious disease; malignant neoplasm; and inflammatory disease, including arthritis, and skin ulcer. A compound of the present invention is also useful as a herbicide.

A compound of the present invention is particularly useful as a remedy for, for example, diabetes mellitus, obesity, or non-alcoholic fatty liver, or as a herbicide.

The present invention is described below in more detail, beginning with the definitions of the terms used herein.

The "halogen" means a fluorine atom, a chlorine atom, a bromine atom, or an iodine atom.

The "$C_{1-6}$ alkyl" means straight-chain or branched alkyl having 1 to 6 carbon atoms, for example, such as methyl, ethyl, propyl, isopropyl, butyl, isobutyl, sec-butyl, tert-butyl, pentyl, isopentyl, hexyl, and isohexyl.

The "halo $C_{1-6}$ alkyl" means the $C_{1-6}$ alkyl as defined above, substituted with one or more, preferably 1 to 3 halogen atoms at arbitrary available substitution positions, the halogen atoms being the same or different and as defined above.

Examples include fluoromethyl, difluoromethyl, trifluoromethyl, 2-fluoroethyl, 1,2-difluoroethyl, chloromethyl, 2-chloroethyl, 1,2-dichloroethyl, bromomethyl, and iodomethyl.

The "$C_{3-8}$ cycloalkyl" means cycloalkyl having 3 to 8 carbon atoms, for example, such as cyclopropyl, cyclobutyl, cyclopentyl, and cyclohexyl.

The "$C_{1-6}$ alkoxy" means straight-chain or branched alkoxy having 1 to 6 carbon atoms, for example, such as methoxy, ethoxy, propoxy, isopropoxy, butoxy, sec-butoxy, isobutoxy, tert-butoxy, pentyloxy, isopentyloxy, hexyloxy, and isohexyloxy.

The "halo $C_{1-6}$ alkoxy" means the $C_{1-6}$ alkoxy as defined above, substituted with one or more, preferably 1 to 3 halogen atoms at arbitrary available substitution positions, the halogen atoms being the same or different and as defined above. Examples include fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, and iodomethoxy.

The "$C_{1-6}$ alkoxycarbonyl" is a group with the $C_{1-6}$ alkoxy bound to carbonyl. Examples include methoxycarbonyl, ethoxycarbonyl, and n-propyloxycarbonyl.

The "$C_{1-6}$ alkoxycarbonylamino" is a group in which one of the hydrogen atoms of the amino group (—NH$_2$) is substituted with the $C_{1-6}$ alkoxycarbonyl. Examples include methoxycarbonylamino, ethoxycarbonylamino, and n-propyloxycarbonylamino.

The "$C_{1-6}$ alkylcarbonyl" is a group with the $C_{1-6}$ alkyl bound to carbonyl. Examples include acetyl, propionyl, isobutyryl, valeryl, isovaleryl, and pivaloyl.

The "$C_{1-6}$ alkylcarbonylamino" is a group in which one of the hydrogen atoms of the amino group is substituted with the $C_{1-6}$ alkylcarbonyl. Examples include acetylamino, propionylamino, isobutyrylamino, valerylamino, isovalerylamino, and pivaloylamino.

The "$C_{1-6}$ alkylsulfonyl" means a group with the $C_{1-6}$ alkyl bound to a sulfonyl group. Examples include methylsulfonyl, ethylsulfonyl, and n-propylsulfonyl.

The "$C_{1-6}$ alkylsulfonylamino" is a group in which one of the hydrogen atoms of the amino group is substituted with the $C_{1-6}$ alkylsulfonyl. Examples include methylsulfonylamino, ethylsulfonylamino, and n-propylsulfonylamino.

The "$C_{1-6}$ alkylsulfinyl" is a group with the $C_{1-6}$ alkyl bound to a sulfinyl group. Examples include methylsulfinyl, ethylsulfinyl, and n-propylsulfinyl.

Examples of the "aryl" include phenyl and naphthyl.

The "heteroaryl" means a five- or six-membered monocyclic heteroaryl having one or more, preferably 1 to 3 heteroatoms, the same or different, selected from the group consisting of an oxygen atom, a nitrogen atom, and a sulfur atom, or a condensed-ring heteroaryl formed by the condensation of the monocyclic heteroaryl and the aryl, or by the condensation of the monocyclic heteroaryls which may be the same or different. Examples include pyrrolyl, furyl, thienyl, imidazolyl, pyrazolyl, thiazolyl, isothiazolyl, oxazolyl, isooxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzoimidazolyl, benzopyrazolyl, benzooxazolyl, benzoisooxazolyl, benzothiazolyl, benzoisothiazolyl, indazolyl, purinyl, quinolyl, isoquinolyl, phthalazinyl, naphthyridinyl, quinoxalinyl, quinazolinyl, cinnolinyl, pteridinyl, and pyrido[3,2-b]pyridyl.

The "aryl" or "heteroaryl" may be substituted with a substituent selected from the group consisting of hydroxy, cyano, halogen, $C_{1-6}$ alkyl, halo $C_{1-6}$ alkyl, $C_{3-8}$ cycloalkyl, $C_{1-6}$ alkoxy, halo $C_{1-6}$ alkoxy, $C_{3-8}$ cycloalkoxy, amino, $C_{1-6}$ alkylamino, di-$C_{1-6}$ alkylamino, halo $C_{1-6}$ alkylamino, dihalo $C_{1-6}$ alkylamino, $C_{3-8}$ cycloalkylamino, di-$C_{3-8}$ cycloalkylamino, carbamoyl, $C_{1-6}$ alkylcarbamoyl, di-$C_{1-6}$ alkylcarbamoyl, halo $C_{1-6}$ alkylcarbamoyl, dihalo $C_{1-6}$ alkylcarbamoyl, $C_{3-8}$ cycloalkylcarbamoyl, di-$C_{3-8}$ cycloalkylcarbamoyl, thiol, $C_{1-6}$ alkylthio, halo $C_{1-6}$ alkylthio, $C_{3-8}$ cycloalkylthio, $C_{1-6}$ alkylsulfinyl, halo $C_{1-6}$ alkylsulfinyl, $C_{3-8}$ cycloalkylsulfinyl, $C_{1-6}$ alkylsulfonyl, halo $C_{1-6}$ alkylsulfonyl, $C_{3-8}$ cycloalkylsulfonyl, $C_{1-6}$ alkylcarbonyl, halo $C_{1-6}$ alkylcarbonyl, $C_{3-8}$ cycloalkylcarbonyl, $C_{1-6}$ alkoxycarbonyl, halo $C_{1-6}$ alkoxycarbonyl, $C_{3-8}$ cycloalkoxycarbonyl, $C_{1-6}$ alkoxycarbonylamino, halo $C_{1-6}$ alkoxycarbonylamino, $C_{3-8}$ cycloalkoxycarbonylamino, $C_{1-6}$ alkylcarbonylamino, halo $C_{1-6}$ alkylcarbonylamino, and $C_{3-8}$ cycloalkylcarbonylamino.

The "arylcarbonyl" is a group with the aryl bound to carbonyl.

The "heteroarylcarbonyl" is a group with the heteroaryl bound to carbonyl.

The "arylcarbonylamino" is a group in which one of the hydrogen atoms of the amino group is substituted with the arylcarbonyl.

The "heteroarylcarbonylamino" is a group in which one of the hydrogen atoms of the amino group is substituted with the heteroarylcarbonyl.

The "aryloxy" is a group with the aryl bound to an oxygen atom.

The "heteroaryloxy" is a group with the heteroaryl bound to an oxygen atom.

The "aryloxycarbonyl" is a group with the aryloxy bound to carbonyl.

The "heteroaryloxycarbonyl" is a group with the heteroaryloxy bound to carbonyl.

The "aryloxycarbonylamino" is a group in which one of the hydrogen atoms of the amino group is substituted with the aryloxycarbonyl.

The "heteroaryloxycarbonylamino" is a group in which one of the hydrogen atoms of the amino group is substituted with the heteroaryloxycarbonyl.

The "arylsulfinyl" is a group with the aryl bound to a sulfinyl group.

The "heteroarylsulfinyl" is a group with the heteroaryl bound to a sulfinyl group.

The "arylsulfonyl" is a group with the aryl bound to a sulfonyl group.

The "heteroarylsulfonyl" is a group with the heteroaryl bound to a sulfonyl group.

The "arylsulfonylamino" is a group in which one of the hydrogen atoms of the amino group is substituted with the arylsulfonyl.

The "heteroarylsulfonylamino" is a group in which one of the hydrogen atoms of the amino group is substituted with the heteroarylsulfonyl.

The "aralkyl" means a group with the $C_{1-6}$ alkyl bound to the aryl. Examples include benzyl, 1-phenylethyl, 2-phenylethyl, 1-naphthylmethyl, and 2-naphthylmethyl.

The "heteroaralkyl" means a group with the $C_{1-6}$ alkyl bound to the heteroaryl.

The "aralkyloxy" means a group with the aralkyl bound to an oxygen atom.

The "heteroaralkyloxy" means a group with the heteroaralkyl bound to an oxygen atom.

The "heterocyclyl" is a saturated, partially saturated, or unsaturated monocyclic or bicyclic ring having 4 to 10 atoms that include 1 to 3 hetero atoms selected from nitrogen, oxygen, and sulfur, wherein the ring nitrogen atom may be substituted with a group selected from $C_{1-6}$ alkyl, amino-$C_{1-6}$ alkyl, aryl, aryl-$C_{1-6}$ alkyl, and acyl, and wherein the ring carbon atom may be substituted with $C_{1-6}$ alkyl, amino-$C_{1-6}$ alkyl, aryl, aryl-$C_{1-6}$ alkyl, heteroaryl, $C_{1-6}$ alkoxy, hydroxy, or oxo. Examples include pyrrolidinyl, oxazolidinyl, thiazolidinyl, piperidinyl, morpholinyl, piperazinyl, dioxolanyl, and tetrahydropyranyl.

A "salt" of a compound of the present invention means a pharmaceutically acceptable salt commonly used. For example, in the case of a carboxyl group, the salt may be a base addition salt formed at the carboxyl group. The salt may be an acid addition salt of amino group or the basic heterocyclic group.

Examples of the base addition salt include: alkali metal salts such as sodium salt, and potassium salt; alkali-earth metal salts such as calcium salt, and magnesium salt; ammonium salts; and organic amine salts such as trimethylamine salt, triethylamine salt, dicyclohexylamine salt, ethanolamine salt, diethanolamine salt, triethanolamine salt, procaine salt, and N,N'-dibenzylethylenediamine salt.

Examples of the acid addition salt include: inorganic acid salts such as hydrochloride, sulfate, nitrate, phosphate, and perchlorate; organic acid salts such as maleate, fumarate, tartrate, citrate, ascorbate, and trifluoroacetate; and sulfonates such as methanesulfonate, isethionate, benzenesulfonate, and p-toluenesulfonate.

The following discloses a compound of the present invention in more detail based on specific preferable examples of various symbols used in Formula (I).

The "arbitrary available substitution positions", as that term is used herein, refer to the position where a hydrogen atom chemically acceptable for substitution is present on carbon, nitrogen, oxygen and/or sulfur atoms, and at which substitution of the hydrogen atom creates a chemically stable compound.

A compound of the present invention, depending on the type of the substituent or its salt form, may exist as a stereoisomer, such as an optical isomer, a diastereomer, and a geometric isomer, or as a tautomer. A compounds of the present invention encompass all such stereoisomers, tautomers, and mixtures thereof.

The present invention encompass various crystals, amorphous forms, salts, hydrates, and solvates of a compound of the present invention.

A prodrug of a compound of the present invention also falls within the scope of the present invention. Generally, such a prodrug is a functional derivative of a compound of the present invention, easily convertible into a compound required in the body. Accordingly, in the treatment of various diseases according to the present invention, the term "administration" encompasses not only the administration of a specific compound but the administration of a compound that converts into a specific compound in the body after being given to a patient. Routine means for the selection and production of a suitable prodrug derivative are described in, for example, *Design of Prodrugs*, ed. H. Bundgaard, Elsevier, 1985, the entire disclosure of which is hereby incorporated herein by reference. The metabolites of these compounds are inclusive of active compounds produced from a compound of the present invention in a biological environment, and such metabolites also fall within the scope of the present invention.

$R^1$ represents $C_{1-6}$ alkyl, $C_{3-8}$ cycloalkyl, aryl, or heteroaryl, wherein the alkyl, cycloalkyl, aryl, or heteroaryl may be substituted with a substituent selected from the group consisting of hydroxy, cyano, carboxyl, sulfo, halogen, $C_{1-6}$ alkyl, halo $C_{1-6}$ alkyl, $C_{3-8}$ cycloalkyl, $C_{1-6}$ alkoxy, halo $C_{1-6}$ alkoxy, amino (the amino being optionally substituted with 1 to 2 $C_{1-6}$ alkyls, aryls, or heteroaryls), carbamoyl (the carbamoyl being optionally substituted with 1 to 2 $C_{1-6}$ alkyls, aryls, or heteroaryls), sulfanyl (the sulfanyl being optionally substituted with one $C_{1-6}$ alkyl, aryl, or heteroaryl), $C_{1-6}$ alkylsulfinyl, arylsulfinyl, heteroarylsulfinyl, $C_{1-6}$ alkylsulfonyl, arylsulfonyl, heteroarylsulfonyl, sulfamoyl (the sulfamoyl being optionally substituted with 1 to 2 $C_{1-6}$ alkyls, aryls, or heteroaryls), $C_{1-6}$ alkylsulfonylamino, arylsulfonylamino, heteroarylsulfonylamino, $C_{1-6}$ alkylcarbonyl, arylcarbonyl, heteroarylcarbonyl, $C_{1-6}$ alkoxycarbonyl, aryloxycarbonyl, heteroaryloxycarbonyl, carbamoylamino (the carbamoylamino being optionally substituted with 1 to 2 $C_{1-6}$ alkyls, aryls, or heteroaryls), $C_{1-6}$ alkoxycarbonylamino, aryloxycarbonylamino, heteroaryloxycarbonylamino, $C_{1-6}$ alkylcarbonylamino, arylcarbonylamino, heteroarylcarbonylamino, aryl, heteroaryl, aralkyl, heteroaralkyl, aralkyloxy, and heteroaralkyloxy.

$R^1$ is preferably, $C_{1-6}$ alkyl, $C_{3-8}$ cycloalkyl, aryl, or heteroaryl, examples of which include those optionally substituted with a substituent selected from the group consisting of halogen, $C_{1-6}$ alkyl, and $C_{1-6}$ alkoxy.

Specific examples of $R^1$ include methyl, ethyl, propyl, isopropyl, butyl, isobutyl, cyclopropyl, cyclobutyl, cyclopentyl, cyclohexyl, phenyl, 2-chlorophenyl, 3-chlorophenyl, 4-chlorophenyl, 2-fluorophenyl, 3-fluorophenyl, 4-fluorophenyl, 2,3-difluorophenyl, 2,4-difluorophenyl, 2-trifluoromethylphenyl, 3-trifluoromethylphenyl, 4-trifluoromethylphenyl, 2-methoxyphenyl, 3-methoxyphenyl, 4-methoxyphenyl, pyridin-2-yl, pyridin-3-yl, pyridin-4-yl, pyrimidin-2-yl, pyrazin-2-yl, pyridazin-3-yl, 2-thienyl, 3-thienyl, 1-methyl-1H-imidazol-4-yl, 5-methyl-1,3,4-thiadiazol-2-yl, 1,3-thiazol-2-yl, 1,3-oxazol-2-yl, and 1,3,4-thiadiazol-2-yl. Preferably, it is recommended that $R^1$ be propyl, isopropyl, butyl, isobutyl, cyclopropyl, phenyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-methoxyphenyl, 3-methoxyphenyl, 4-methoxyphenyl, pyridin-2-yl, pyridin-3-yl, pyridin-4-yl, pyrimidin-2-yl, pyrazin-2-yl, pyridazin-3-yl, 2-thienyl, 3-thienyl, 1-methyl-1H-imidazol-4-yl, 5-methyl-1,3,4-thiadiazol-2-yl, 1,3-thiazol-2-yl, 1,3-oxazol-2-yl, or 1,3,4-thiadiazol-2-yl.

$R^2$ represents phenyl or heteroaryl, wherein the phenyl or heteroaryl may be substituted with a substituent selected from the group consisting of hydroxy, cyano, carboxyl, sulfo, halogen, $C_{1-6}$ alkyl, halo $C_{1-6}$ alkyl, $C_{3-8}$ cycloalkyl, $C_{1-6}$ alkoxy, halo $C_{1-6}$ alkoxy, amino (the amino being optionally substituted with 1 to 2 $C_{1-6}$ alkyls, aryls, or heteroaryls), carbamoyl (the carbamoyl being optionally substituted with 1 to 2 $C_{1-6}$ alkyls, aryls, or heteroaryls), sulfanyl (the sulfanyl being optionally substituted with one $C_{1-6}$ alkyl, aryl, or heteroaryl), $C_{1-6}$ alkylsulfinyl, arylsulfinyl, heteroarylsulfinyl, $C_{1-6}$ alkylsulfonyl, arylsulfonyl, heteroarylsulfonyl, sulfamoyl (the sulfamoyl being optionally substituted with 1 to 2 $C_{1-6}$ alkyls, aryls, or heteroaryls), $C_{1-6}$ alkylsulfonylamino, arylsulfonylamino, heteroarylsulfonylamino, $C_{1-6}$ alkylcarbonyl, arylcarbonyl, heteroarylcarbonyl, $C_{1-6}$ alkoxycarbonyl, aryloxycarbonyl, heteroaryloxycarbonyl, carbamoylamino (the carbamoylamino being optionally substituted with 1 to 2 $C_{1-6}$ alkyls, aryls, or heteroaryls), $C_{1-6}$ alkoxycarbonylamino, aryloxycarbonylamino, heteroaryloxycarbonylamino, $C_{1-6}$ alkylcarbonylamino, arylcarbonylamino, heteroarylcarbonylamino, aryl (the aryl being optionally substituted with $C_{1-6}$ alkoxy), heteroaryl, aryloxy, heteroaryloxy, aralkyl, heteroaralkyl, aralkyloxy, and heteroaralkyloxy.

$R^2$ is preferably phenyl or heteroaryl, examples of which include those substituted with a substituent selected from the group consisting of halogen, $C_{1-6}$ alkyl, halo $C_{1-6}$ alkyl, $C_{1-6}$ alkoxy, $C_{3-6}$ cycloalkyl, aryl (the aryl being optionally substituted with $C_{1-6}$ alkoxy), aralkyl, and aralkyloxy.

Specific examples of $R^2$ include phenyl, 2-methoxyphenyl, 3-methoxyphenyl, 4-methoxyphenyl, 2-ethoxyphenyl, 3-ethoxyphenyl, 4-ethoxyphenyl, 2-isopropoxyphenyl, 3-isopropoxyphenyl, 4-isopropoxyphenyl, 2-isobutyloxyphenyl, 3-isobutyloxyphenyl, 4-isobutyloxyphenyl, 2-cyclopropyloxyphenyl, 3-cyclopropyloxyphenyl, 4-cyclopropyloxyphenyl, 2-fluorophenyl, 3-fluorophenyl, 4-fluorophenyl, 2-chlorophenyl, 3-chlorophenyl, 4-chlorophenyl, 2-trifluoromethylphenyl, 3-trifluoromethylphenyl, 4-trifluoromethylphenyl, 2-phenoxyphenyl, 3-phenoxyphenyl, 4-phenoxyphenyl, 2-benzyloxyphenyl, 3-benzyloxyphenyl, 4-benzyloxyphenyl, 2-benzylphenyl, 3-benzylphenyl, 4-benzylphenyl, 2-methylphenyl, 3-methylphenyl, 4-methylphenyl, 2-isopropylphenyl, 3-isopropylphenyl, 4-isopropylphenyl, 5-isopropoxyphenylpyridin-2-yl, 6-isopropoxyphenylpyridin-3-yl, 5-isopropoxypyrimidin-2-yl, 3-methoxypyridin-2-yl, 3-cyclopropyl-1H-pyrazol-5-yl, and 5-isopropoxy-1H-pyrazol-3-yl. Preferably, it is recommended that $R^2$ be phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-isopropylphenyl, 3-isopropylphenyl, 4-isopropylphenyl, 2-isopropoxyphenyl, 3-isopropoxyphenyl, 4-isopropoxyphenyl, 2-benzylphenyl, 3-benzylphenyl, 4-benzylphenyl, 2-benzyloxyphenyl, 3-benzyloxyphenyl, 4-benzyloxyphenyl, 5-isopropoxyphenylpyridin-2-yl, 6-isopropoxyphenylpyridin-3-yl, 5-isopropoxypyrimidin-2-yl, 3-methoxypyridin-2-yl, 3-cyclopropyl-1H-pyrazol-5-yl, or 5-isopropoxy-1H-pyrazol-3-yl.

$R^3$ represents a hydrogen atom, $C_{1-6}$ alkyl, $C_{3-8}$ cycloalkyl, aralkyl, heteroaralkyl, aryl, or heteroaryl, wherein the alkyl, cycloalkyl, aralkyl, aryl, or heteroaryl may be substituted with a substituent selected from the group consisting of halogen, $C_{1-6}$ alkyl, halo $C_{1-6}$ alkyl, $C_{1-6}$ alkoxy, and halo $C_{1-6}$ alkoxy.

Specific examples of $R^3$ include a hydrogen atom, methyl, ethyl, propyl, butyl, pentyl, hexyl, isopropyl, isobutyl, isopentyl, phenyl, pyridin-2-yl, pyridin-3-yl, pyridin-4-yl, pyrimidin-2-yl, and benzyl. Preferable examples include a hydrogen atom, methyl, ethyl, propyl, isopropyl, phenyl, pyridin-2-yl, pyridin-3-yl, pyridin-4-yl, and benzyl. Particularly, it is recommended that $R^3$ be a hydrogen atom.

Z is selected from the group consisting of the following Formulae (II-1), (II-2), and (II-3).

[Chemical Formula 3]

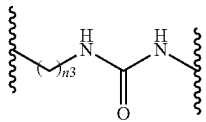
(II-1)

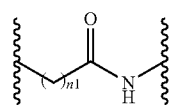
(II-2)

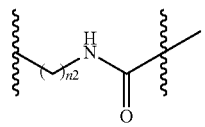
(II-3)

wherein n1, n2, and n3 are 0, 1, or 2, respectively.

Z is preferably (II-1) or (II-2). When Z is (II-1), it is recommended that n1=0. When Z is (II-2), it is recommended that n2=1.

$M_1$, $M_2$, $M_3$, and $M_4$ independently represent a hydrogen atom, or $C_{1-6}$ alkyl optionally substituted with halogen; or $M_1$, together with $M_2$, $M_3$, or $M_4$, forms —$CH_2$— or —$CH_2$—$CH_2$—; or $M_4$, together with $M_2$, forms —$CH_2$— or —$CH_2$—$CH_2$—;
provided that $R^3$ is a hydrogen atom, then any two of $M_1$, $M_2$, $M_3$, and $M_4$ together form —$CH_2$— or —$CH_2$—$CH_2$—.

Specific examples of $M_1$, $M_2$, $M_3$, and $M_4$ include a hydrogen atom, methyl, ethyl, n-propyl, n-butyl, chloromethyl, fluoromethyl, and trifluoromethyl. Alternatively, $M_1$, together with $M_2$, $M_3$, or $M_4$, forms —$CH_2$— or —$CH_2$—$CH_2$—, or $M_4$, together with $M_2$, forms —$CH_2$— or —$CH_2$—$CH_2$—.

Examples of specific combinations of $M_1$, $M_2$, $M_3$, and $M_4$ include:

(1) $M_1$, together with $M_2$, forming —$CH_2$— or —$CH_2$—$CH_2$—, and $M_3$ and $M_4$ being independently a hydrogen atom, or $C_{1-6}$ alkyl optionally substituted with halogen;

(2) $M_1$, together with $M_3$, forming —$CH_2$— or —$CH_2$—$CH_2$—, and $M_2$ and $M_4$ being independently a hydrogen atom, or $C_{1-6}$ alkyl optionally substituted with halogen;

(3) $M_1$, together with $M_4$, forming —$CH_2$— or —$CH_2$—$CH_2$—, and $M_1$ and $M_2$ being independently a hydrogen atom, or $C_{1-6}$ alkyl optionally substituted with halogen;

(4) $M_4$, together with $M_2$, forming —$CH_2$— or —$CH_2$—$CH_2$—, and $M_1$ and $M_3$ being independently a hydrogen atom, or $C_{1-6}$ alkyl optionally substituted with halogen; and (5) $M_1$, $M_2$, $M_3$, and $M_4$ all being hydrogen atoms.

Preferable combinations of $M_1$, $M_2$, $M_3$, and $M_4$ include:
$M_1$, together with $M_3$, forming —$CH_2$— or —$CH_2$—$CH_2$—, and $M_2$ and $M_4$ being independently a hydrogen atom, or $C_{1-6}$ alkyl optionally substituted with halogen;

$M_1$, together with $M_2$, forming —$CH_2$— or —$CH_2$—$CH_2$—, and $M_3$ and $M_4$ being independently a hydrogen atom, or $C_{1-6}$ alkyl optionally substituted with halogen; and $M_1$, $M_2$, $M_3$, and $M_4$ all being hydrogen atoms.

Particularly, it is recommended that:
$M_1$, together with $M_2$, form —$CH_2$—$CH_2$—, and $M_3$ and $M_4$ each represent a hydrogen atom;

$M_1$, together with $M_3$, form —$CH_2$—$CH_2$—, and $M_2$ and $M_4$ each represent a hydrogen atom; or $M_1$, $M_2$, $M_3$, and $M_4$ all represent hydrogen atoms.

A compound of the present invention may include one or more asymmetric centers, and can therefore occur as a racemate or a racemic mixture, a single enantiomer, a mixture of diastereomers, or an individual diastereomer. Each such asymmetric center will independently produce two optical isomers, and the present invention encompass all possible optical isomers and diastereomers, either as a mixture, a pure compound, or a partially purified compound.

Preferably, it is recommended that the compound of Formula (I) is:
(1R,4S,6R**)-N-(4-isopropoxyphenyl)-2-[(1-methyl-1H-imidazol-4-yl)sulfonyl]-2-azabicyclo[2.2.2]octane-6-carboxamide;

(1S\*\*,4R\*\*,6S\*\*)-N-(4-isopropoxyphenyl)-2-[(1-methyl-1H-imidazol-4-yl)sulfonyl]-2-azabicyclo[2.2.2]octane-6-carboxamide;

(1R\*,4S\*,6R\*)-2-(butylsulfonyl)-N-(3-cyclopropyl-1H-pyrazol-5-yl)-2-azabicyclo[2.2.2]octane-6-carboxamide;

(1R\*,4S\*,6R\*)-N-(5-isopropoxypyridin-2-yl)-2-(pyridin-2-ylsulfonyl)-2-azabicyclo[2.2.2]octane-6-carboxamide;

(1R\*\*,4S\*\*,6R\*\*)-N-(5-isopropoxypyridin-2-yl)-2-[(1-methyl-1H-imidazol-4-yl)sulfonyl]-2-azabicyclo[2.2.2]octane-6-carboxamide;

(1S\*\*,4R\*\*,6S\*\*)-N-(5-isopropoxypyridin-2-yl)-2-[(1-methyl-1H-imidazol-4-yl)sulfonyl]-2-azabicyclo[2.2.2]octane-6-carboxamide;

2-methoxy-N-{[3-phenyl-1-(pyridin-2-ylsulfonyl)piperidin-3-yl]methyl}benzamide;

4-isopropoxy-N-{[3-phenyl-1-(pyridin-2-ylsulfonyl)piperidin-3-yl]methyl}benzamide;

4-isopropoxy-N-({1-[(1-methyl-1H-imidazol-4-yl)sulfonyl]-3-phenylpiperidin-3-yl}methyl)benzamide;

5-isopropoxy-N{[3-phenyl-1-(propylsulfonyl)piperidin-3-yl]methyl}pyridine-2-carboxamide;

5-isopropoxy-N-{[3-phenyl-1-(pyridin-2-ylsulfonyl)piperidin-3-yl]methyl}pyridine-2-carboxamide;

5-isopropoxy-N-({1-[(1-methyl-1H-imidazol-4-yl)sulfonyl]-3-phenylpiperidin-3-yl}methyl)pyridine-2-carboxamide;

4-isopropoxy-N-{[3-methyl-1-(phenylsulfonyl)piperidin-3-yl]methyl}benzamide;

4-isopropoxy-N-{[3-methyl-1-(pyridin-2-ylsulfonyl)piperidin-3-yl]methyl}benzamide;

N-{[3-ethyl-1-(pyridin-2-ylsulfonyl)piperidin-3-yl]methyl}-4-isopropoxybenzamide;

N-({3-ethyl-1-[(1-methyl-1H-imidazol-4-yl)sulfonyl]piperidin-3-yl}methyl)-4-isopropoxybenzamide;

3-isobutyl-N-({1-[(1-methyl-1H-imidazol-4-yl)sulfonyl]-3-phenylpiperidin-3-yl}methyl)-1H-pyrazole-5-carboxamide;

3-ethyl-N-(5-isopropoxypyridin-2-yl)-1-[(1-methyl-1H-imidazol-4-yl)sulfonyl]piperidine-3-carboxamide;

3-ethyl-N-(5-isopropoxy-1H-pyrazol-3-yl)-1-[(1-methyl-1H-imidazol-4-yl)sulfonyl]piperidine-3-carboxamide; or (1R\*,4S\*,6R\*)-N-(5-isopropoxy-1H-pyrazol-3-yl)-2-[(1-methyl-1H-imidazol-4-yl)sulfonyl]-2-azabicyclo[2.2.2]octane-6-carboxamide.

Producing Methods of a Compound of Formula (I)

A compound according to the present invention can be produced by methods described in, for example, the Producing Method and Example Sections below. It should be noted, however, that producing methods of a compound according to the present invention are not limited to the examples below.

Producing Method 1

A compound of Formula (I) with Z=(II-1), namely a compound of Formula (I-1) can be prepared according to the following method.

Producing Method 1

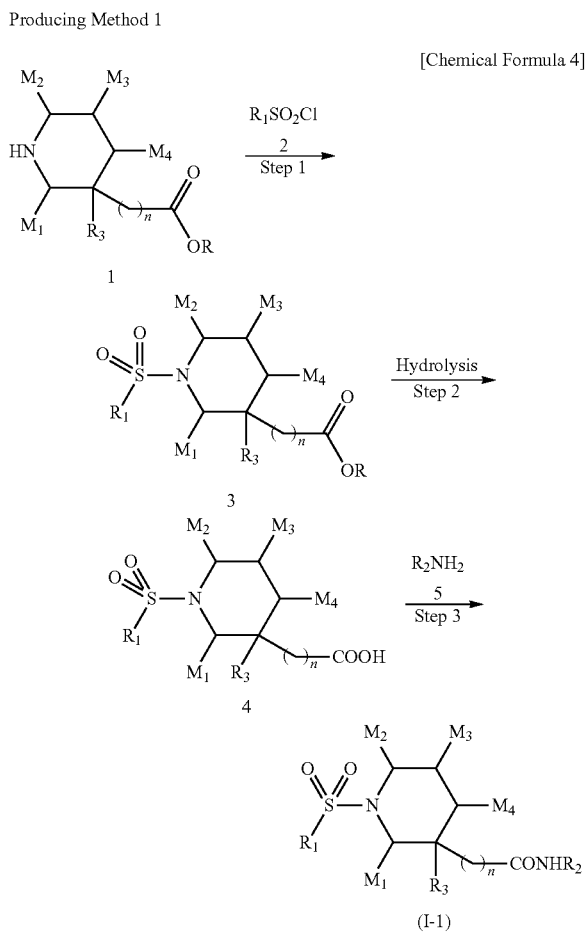

[Chemical Formula 4]

[The symbols in the Formula are as defined above.]

Step 1

Compound 1 is allowed to react with Compound 2 in an organic solvent in the presence of a base to obtain Compound 3.

It is recommended that Compound 2 be used, for example, in 1 to 5 moles, preferably 1 to 3 moles per mole of Compound 1.

Examples of the base include triethylamine, diisopropylethylamine, and pyridine. It is recommended that the base be used, for example, in 1 to 10 moles, preferably 1 to 3 moles per mole of Compound 1.

Examples of the organic solvent include methylene chloride, chloroform, toluene, tetrahydrofuran (hereinafter, "THF"), 1,4-dioxane, dimethyl sulfoxide (hereinafter, "DMSO"), ethyl acetate, and acetonitrile.

It is recommended that the reaction temperature be, for example, 0 to 60° C., preferably 0 to 30° C. The reaction generally completes in 1 to 24 hours.

The Compound 3 obtained as above can easily be isolated and purified using common separation means, for example, such as solvent extraction, recrystallization, column chromatography, and preparative thin-layer chromatography (this method can be applied to the following methods).

Examples of Compound 1 include ethyl 3-ethylpiperidine-3-carboxylate, ethyl piperidine-3-carboxylate, and methyl 2-azabicyclo[2.2.2]octane-6-carboxylate. Examples of Compound 2 include methanesulfonyl chloride, ethanesulfonyl chloride, propanesulfonyl chloride, butanesulfonyl chloride, and benzenesulfonyl chloride.

Step 2

Compound 3 is subjected to hydrolysis using a known method to obtain Compound 4.

Although the method is not particularly limited, hydrolysis can be performed in an organic solvent, for example, such as methanol and ethanol, in a temperature range of from room temperature to the boiling point of the solvent, using a sodium hydroxide solution, a potassium hydroxide solution, or the like.

Step 3

Compound 4 and Compound 5 are subjected to an amidation reaction to obtain a compound of Formula (I-1).

Amidation can be performed using known methods. For example, Compound 4 and Compound 5 may react with each other in the presence of a condensing agent, or the carboxylic acid moiety of Compound 4 may be activated to form a reactive derivative using a known method, and the derivative may undergo amidation with Compound 5. (For details of these methods, see *Pepuchido Gosei no Kiso to Jikken*, Nobuo Izumiya, et al., Maruzen Co., Ltd., 1983.)

The reaction using a condensing agent can be performed as follows, for example.

Compound 4 and Compound 5 are condensed in a reaction solvent using a condensing agent to obtain the compound of Formula (I-1).

The amount of Compound 5 used is, for example, 1 to 3 moles per mole of Compound 4.

Examples of the condensing agent include dicyclohexylcarbodiimide, 1-ethyl-3-(3-dimethylaminopropyl)-carbodiimide, and O-(7-azabenzotriazol-1-yl)-1,1,3,3-tetra-methyluroniumhexafluorophosphate (hereinafter, "HATU"). The amount used is, for example, 1 to 3 moles per mole of Compound 4.

To promote reaction, hydroxybenzotriazole (hereinafter, "HOBT") or the like may be added to the reaction system. The amount of HOBT used is, for example, 1 to 3 moles per mole of Compound 4.

Examples of the reaction solvent include THF, 1,4-dioxane, N,N-dimethylformamide (hereinafter, "DMF"), DMSO, dichloromethane, chloroform, pyridine, and a mixed solvent thereof.

The reaction temperature is, for example, 20 to 100° C. The recommended reaction temperature is preferably 20 to 50° C. The reaction generally completes in 1 to 24 hours.

Examples of Compound 5 include aniline, 2-methoxyaniline, 3-methoxyaniline, 4-methoxyaniline, and 3-cyclopropyl-1H-pyrazole-5-amine.

Producing Method 2

Producing Method 2 is an alternative synthesis method of the compound of Formula (I-1) using Compound 1 as the raw material.

Producing Method 2

[Chemical Formula 5]

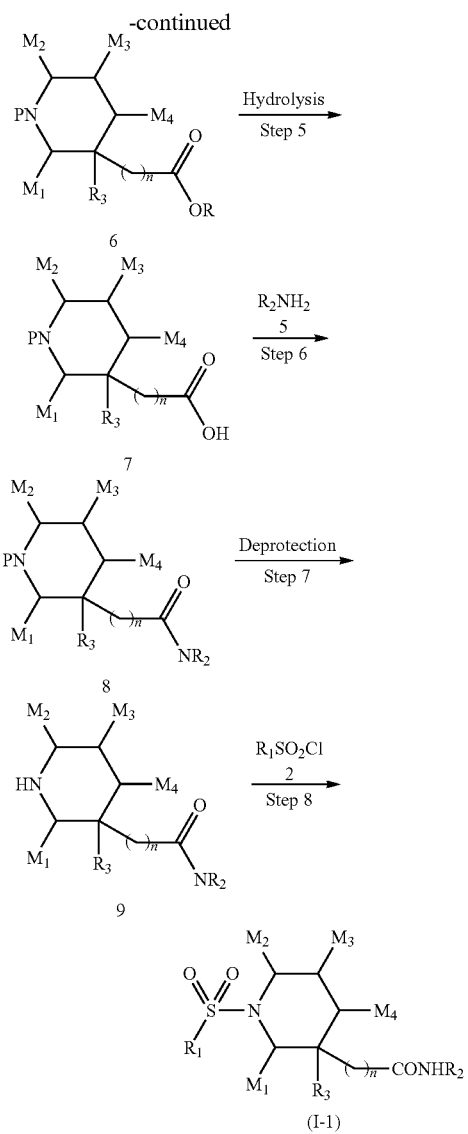

[In the Formula, P represents a protective group; the other symbols are as defined above.]

Step 4

A protective group is introduced into the amino group of Compound 1 to obtain Compound 6. The protective group can be introduced according to the method described in *Protective Groups in Organic Synthesis*, T. W. Greene, John Wiley & Sons, 1981, or using similar methods. Examples of the protective group include tert-butyl oxycarbonyl, benzyloxycarbonyl, and p-methoxybenzyloxycarbonyl.

Step 5

The ester of Compound 6 is hydrolyzed to obtain Compound 7. Although the method is not particularly limited, hydrolysis can be performed in an organic solvent, for example, such as methanol and ethanol, in a temperature range of from room temperature to the boiling point of the solvent, using a sodium hydroxide solution, a potassium hydroxide solution, or the like.

Steps 6 and 7

Compound 7 and Compound 5 are allowed to react according to Step 3 of Producing Method 1 to obtain Compound 8, followed by removing the protective group to obtain Compound 9.

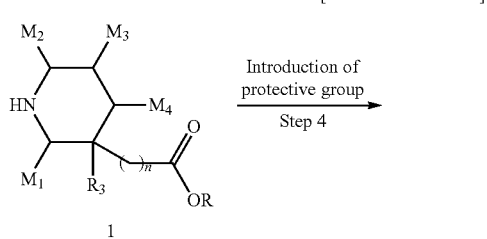

The protective group of Compound 9 can be removed using, for example, the method described in *Protective Groups in Organic Synthesis*.

Step 8

Compound 9 is condensed with Compound 2 according to Step 1 of Producing Method 1 to obtain the compound of Formula (I-1).

Producing Method 3

Producing Method 3 is a method for producing a compound of Formula (I) with Z=(II-2), specifically a compound of Formula (I-2).

Producing Method 3

[Chemical Formula 6]

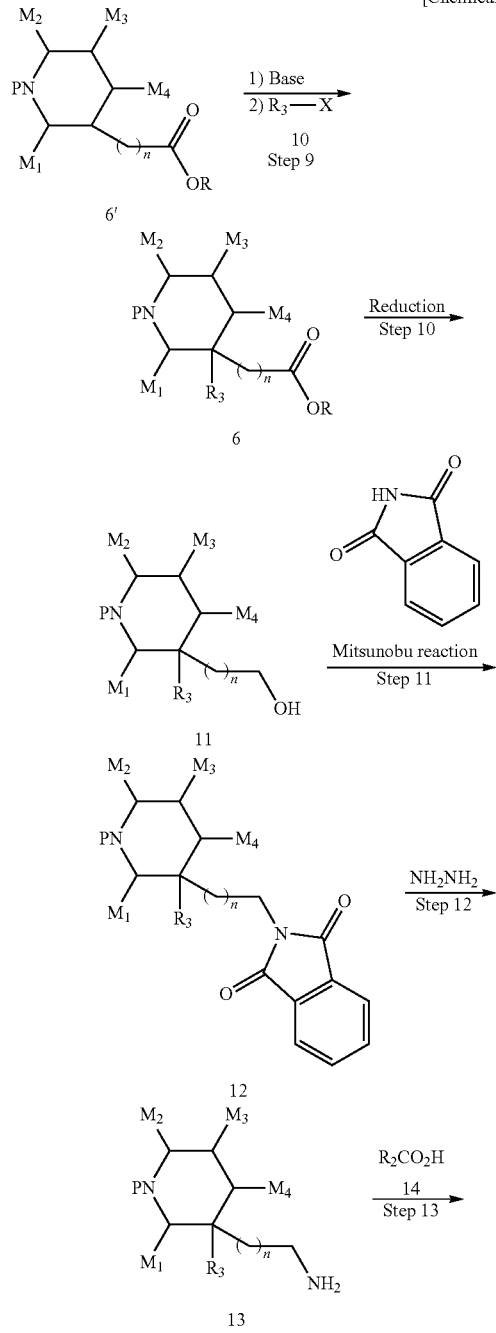

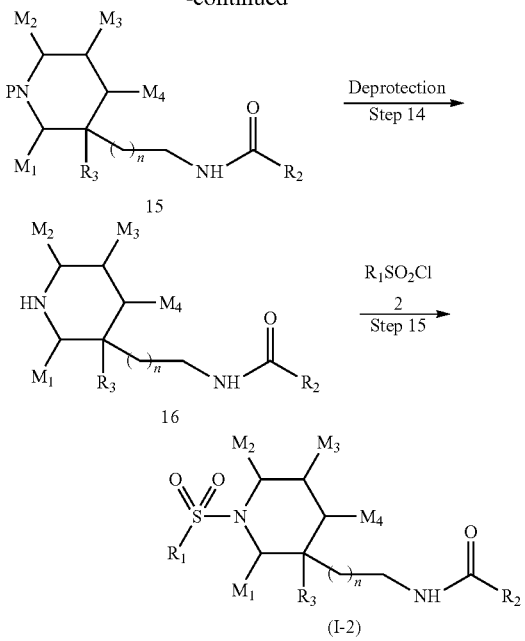

[The symbols in the Formula are as defined above]

Step 9

Compound 6' ($R^3$=H in Compound 6, and as such $R^3$ excludes hydrogen) is treated with a base in a reaction solvent, and adding Compound 10 to the reaction system to obtain Compound 6.

Examples of the base include lithium diisopropylamide (hereinafter, "LDA"). The amount of base used is, for example, 1 to 2 moles per mole of Compound 6'.

Examples of the reaction solvent include THF.

The process temperature is, for example, −78 to 20° C., and the reaction is generally performed for 1 to 2 hours. Compound 10 is then added to the reaction mixture to perform a substitution reaction.

The amount of Compound 10 used is, for example, 1 to 10 moles per mole of Compound 6'. The recommended amount is preferably 1 to 3 moles.

The reaction temperature is, for example, −78 to 20° C., and the reaction generally completes in 1 to 3 hours.

Examples of Compound 10 include methyl iodide, ethyl iodide, isopropyl bromide, and benzyl bromide.

Step 10

Compound 11 is obtained by the reduction of the ester moiety of Compound 6 using a reducing agent such as lithium aluminum hydride and sodium borohydride, using a known method.

Step 11

Compound 11 and phthalimide are condensed by the Mitsunobu reaction to obtain Compound 12.

Specifically, Compound 12 is obtained by the condensation of Compound 11 and phthalimide in the reaction solvent in the presence of azo compounds such as dialkyl azodicarboxylate or 1,1'-(azodicarbonyl)diamide, and organophosphorus compounds such as triarylphosphine or trialkylphosphine.

Examples of the azo compound include dimethyl azodicarboxylate, diethyl azodicarboxylate (hereinafter, "DEAD"), diisopropyl azodicarboxylate (hereinafter, "DIAD"), and 1,1'-(azodicarbonyl)dipiperidide (hereinafter, "DPPA"). Examples of the triarylphosphine include triphenylphosphine, and tritolylphosphine. Examples of the trialkylphosphine include triethylphosphine, and tributylphosphine. A combination of diisopropyl azodicarboxylate and triphenylphosphine, or a combination of 1,1'-(azodicarbonyl)dipiperidide and tributylphosphine is recommended.

The amount of phthalimide used is, for example, 1 to 10 moles per mole of Compound 11. The recommended amount is preferably 1 to 1.5 moles.

The amount of azo compound used is, for example, 1 to 3 moles per mole of Compound 11. The recommended amount is preferably 1 to 1.5 moles. The amount of organophosphorus compound used is, for example, 1 to 3 moles per mole of phthalimide. The recommended amount is preferably 1 to 1.5 moles.

Examples of the reaction solvent include: halocarbons such as methylene chloride, chloroform, dichloroethane, and carbon tetrachloride; aliphatic hydrocarbons such as n-heptane and n-hexane; aromatic hydrocarbons such as benzene, toluene, and xylene; ethers such as diethyl ether, THF, 1,4-dioxane, and ethylene glycol dimethyl ether; esters such as methyl acetate, and ethyl acetate; acetonitrile; N-methylpyrrolidone (hereinafter, "NMP"); DMF; DMSO; and a mixed solvent thereof.

The reaction temperature is, for example, 0° C. to 100° C. The recommended reaction temperature is preferably 0° C. to 50° C. The reaction generally completes in 2 to 24 hours.

Step 12

Compound 12 is subjected to a hydrazine treatment in the reaction solvent to obtain Compound 13.

The amount of hydrazine used is, for example, 1 to 10 moles per mole of Compound 12. The recommended amount is preferably 1 to 5 moles.

Examples of the reaction solvent include methanol and ethanol.

The reaction temperature is, for example, 0 to 60° C., preferably 0 to 30° C. The reaction generally completes in 1 to 24 hours.

Steps 13 to 15

The Compound 13 obtained as above is condensed with Compound 14 according to Step 3 to obtain Compound 15. The protective group of Compound 15 is removed according to Step 7 to obtain Compound 16, which is then allowed to react with Compound 2 according to Step 1 to obtain the compound of Formula (I-2).

Examples of Compound 14 include 2-methoxybenzoic acid, 3-methoxybenzoic acid, 4-methoxybenzoic acid, and 4-isopropoxybenzoic acid.

Producing Method 4

Producing Method 4 is a method for producing the compound of Formula (I-2) using Compound 3 as the raw material.

Producing Method 4

[Chemical Formula 7]

[The symbols in the Formula are as defined above.]

Step 16

Compound 3 is reduced using a reducing agent to obtain Compound 17. The reducing method is according to Step 10.

Steps 17 and 18

Compound 17 is allowed to react with phthalimide according to Step 11 to obtain Compound 18. After the hydrazine treatment of Compound 18 as in Step 12, Compound 19 is obtained.

Step 19

Compound 19 is condensed with Compound 14 according to Step 3 to obtain the compound of Formula (I-2).

Producing Method 5 is a method for producing the compound of Formula (I-2').

Producing Method 5

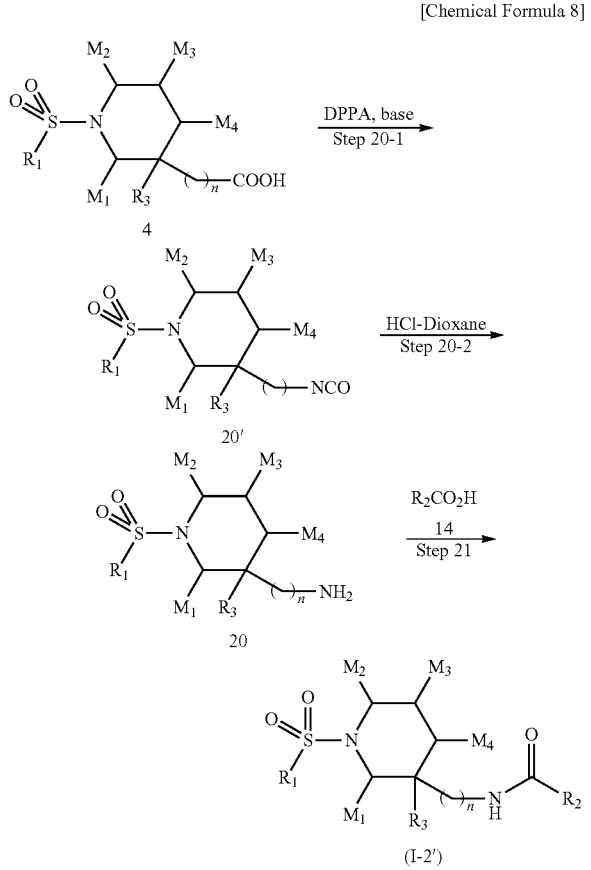

Producing Method 6

Producing Method 6 is a method for producing a compound of Formula (I) with Z=(II-3), namely a compound of Formula (I-3).

Producing Method 6

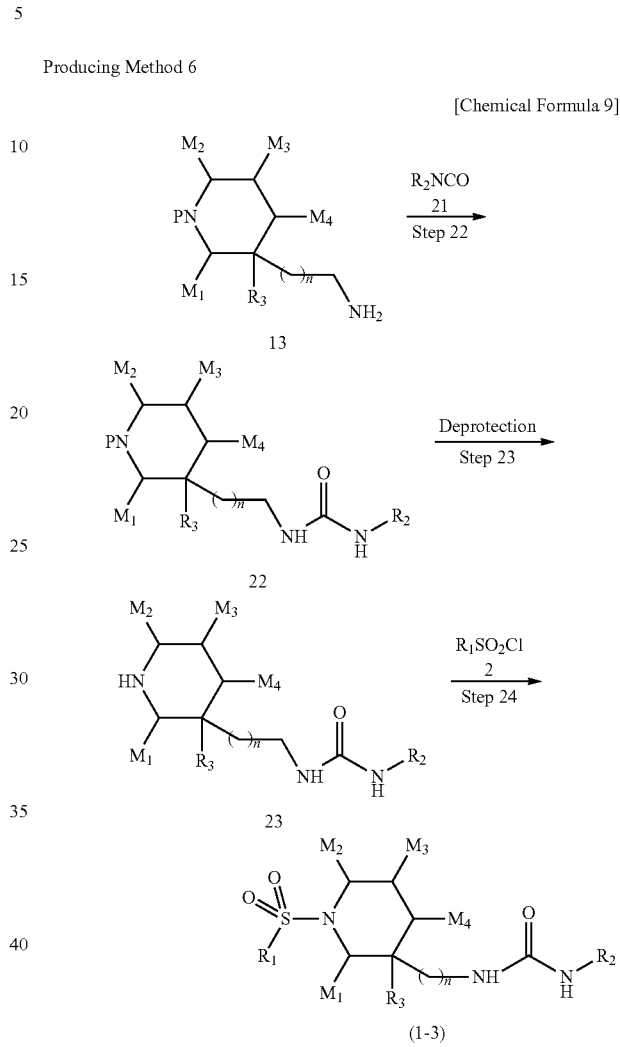

[The symbols in the Formula are as defined above.]

Step 20-1

Compound 20' is obtained by the Curtius rearrangement reaction of Compound 4.

Specifically, Compound 20' is obtained by the reaction of Compound 4 with diphenylphosphoryl azide (DPPA) in a reaction solvent in the presence of a base (see Shioiri, T.; Ninomiya, K.; Yamada, S, J. Am. Chem. Soc., 1972, Vol. 94, pp. 6203-6205).

Examples of the base include triethylamine, and diisopropylethylamine. The amount of base used is, for example, 1 to 4 moles per mole of Compound 4. The recommended amount is preferably 1 to 2 moles.

The amount of DPPA used is, for example, 1 to 4 moles per mole of Compound 4. The recommended amount is preferably 1 to 2 moles.

Examples of the reaction solvent include THF, 1,4-dioxane, and tert-butanol.

The reaction temperature is, for example, 20 to 100° C., preferably 20 to 80° C. The reaction generally completes in 1 to 24 hours.

Step 20-2

Compound 20' is treated with an acid using a 1,4-dioxane solution of excess hydrochloric acid to obtain Compound 20.

The reaction temperature is, for example, 20 to 120° C., preferably 20 to 80° C. The reaction generally completes in 1 to 24 hours.

Step 21

Compound 20 is condensed with Compound 14 according to Step 3 to obtain the compound of Formula (I-2').

[The symbols in the Formula are as defined above.]

Step 22

Compound 13 is reacted with Compound 21 in a reaction solvent in the presence of a base to obtain Compound 22.

Examples of Compound 21 include phenyl isocyanate, and 4-methoxyphenyl isocyanate. The amount used is, for example, 1 to 4 moles per mole of Compound 13. The recommended amount is preferably 1 to 2 moles.

Examples of the base include triethylamine, diisopropylethylamine, and pyridine. The amount of base used is, for example, 1 to 5 moles per mole of Compound 13. The recommended amount is preferably 1 to 3 moles.

Examples of the reaction solvent include pyridine, THF, 1,4-dioxane, methylene chloride, chloroform, and DMSO.

The reaction temperature is, for example, 0 to 100° C., preferably 0 to 50° C. The reaction generally completes in 1 to 24 hours.

Steps 23 and 24

The protective group of Compound 22 is deprotected according to Step 4 to obtain Compound 23. After condensation with Compound 2 according to Step 2, the compound of Formula (I-3) is obtained.

When the reactants in the reactions of the Producing Methods 1 to 6 include groups not involved in the reaction, such as amino, hydroxy, and carboxyl, the reaction may be performed after appropriately protecting the amino, hydroxy, or carboxyl with the protective group, which may be removed after the reaction.

Examples of the protective group for the amino include: aralkyls such as benzyl, p-methoxybenzyl, 3,4-dimethoxybenzyl, o-nitrobenzyl, p-nitrobenzyl, benzhydryl, and trityl; $C_{1-6}$ alkanoyls such as formyl, acetyl, propionyl, butyryl, and pivaloyl; benzoyls; arylalkanoyls such as phenylacetyl and phenoxyacetyl; $C_{1-6}$ alkoxycarbonyls such as methoxycarbonyl, ethoxycarbonyl, propyloxycarbonyl, and tert-butoxycarbonyl; aralkyloxycarbonyls such as benzyloxycarbonyl, p-nitrobenzyloxycarbonyl, and phenethyloxycarbonyl; and $C_{1-6}$ alkylsilyls such as trimethylsilyl, and tert-butyl dimethylsilyl. Particularly preferable examples include acetyl, pivaloyl, benzoyl, ethoxycarbonyl, and tert-butoxycarbonyl.

Examples of the protective group for the hydroxy include: substituted silyls such as trimethylsilyl, tert-butyl dimethylsilyl, and tert-butyl diphenylsilyl; lower alkoxymethyls such as methoxymethyl, and 2-methoxyethoxymethyl; tetrahydropyranyl; aralkyls such as benzyl, and p-methoxybenzyl; acyls such as formyl and acetyl; and benzoyls.

Examples of the protective group for the carboxyl include: $C_{1-6}$ alkyls such as methyl, ethyl, propyl, isopropyl, and tert-butyl; $C_{1-6}$ haloalkyls such as 2,2,2-trichloroethyl; $C_{1-6}$ alkenyls such as 2-propenyl; and aralkyls such as benzyl, p-methoxybenzyl, p-nitrobenzyl, benzhydryl, and trityl. Particularly preferable examples include methyl, ethyl, tert-butyl, 2-propenyl, benzyl, p-methoxybenzyl, and benzhydryl.

The protective group can be introduced and removed according to the method described in *Protective Groups in Organic Synthesis*, or using similar methods.

The compounds of Formulae (I-1), (I-2), and (I-3) thus obtained can be easily isolated and purified using common separation means, for example, such as solvent extraction, recrystallization, column chromatography, and preparative thin-layer chromatography.

The compound can be turned into a pharmaceutically acceptable salt using an ordinary method. The conversion from the salt to a free compound can also be performed according an ordinary method.

The usefulness of a compound according to the present invention as a medicament is demonstrated by the following pharmacological test examples.

Pharmacological Test Example 1

LCE Enzymatic Activity Inhibition Test

A test compound was dissolved in dimethylsulfoxide (DMSO) at 10 mM, and then, the resulting solution was further diluted with DMSO to prepare a 1000-fold stock solution having a concentration 1000 times higher than the concentration to be evaluated. An LCE enzymatic activity inhibition test was carried out by a modified method of Moon (J. Biol. Chem., Vol. 276, pp. 45358-45366, (2001)) et al. That is, the diluted test compound was added to a 96-well assay plate (Corning, 96-Well Assay Block) in an amount of 1.0 μL per well, and thereafter, 50 μL of a phosphate buffer solution (a 100 mM potassium phosphate buffer solution (pH 6.5)), 25 μL of a substrate solution (a 100 mM potassium phosphate buffer solution (pH 6.5), 4.0 μM rotenone, 80 μM fatty acid-free bovine serum albumin, 160 μM palmitoyl-CoA, 80 μM malonyl-CoA, 3.5 μM [$^{14}$C]-malonyl-CoA (1.92 GBq/mmol, manufactured by Amersham, Inc.)) was added to each well, and further, 25 μL of an enzyme solution (a 100 mM potassium phosphate buffer solution (pH 6.5), 100 μg/mL human LCE) was added thereto. Then, the upper part of the plate was hermetically closed with a seal member, and the plate was incubated at 37° C. for 90 minutes while gently shaking and stirring. Thereafter, to each well, 100 μL of 5 N HCl was added and the assay plate was stirred at room temperature for 5 minutes, whereby the enzymatic reaction was stopped and also acyl-CoA was hydrolyzed. Thereafter, the enzymatic reaction solution in each well was adsorbed to each well of a 96-well GF/C filter plate (PerkinElmer, Unifilter 96GF/C) through which water had been passed in advance, and then, each well was washed with water to remove unadsorbed malonyl-CoA and the GF/C filter plate was dried at 50° C. for 60 minutes. Thereafter, to each well, 30 μL of a scintillator (PerkinElmer, Microscinti 0) was added and the upper part of the plate was sealed, and the radioactivity of the fixed [$^{14}$C] was measured using a microplate scintillation counter (PerkinElmer, Top Count) from which the enzymatic activity was determined. The human LCE enzyme inhibitory activity of the test compound was calculated using the radioactivity obtained from a well to which DMSO containing no test compound is added as a control. When the activities of the compounds of the invention were examined using this assay, these compounds inhibited the activity of human LCE. The results are shown in Table 1.

TABLE 1

| Example Number | Name | $IC_{50}$ (nM) |
| --- | --- | --- |
| 26 | (1R*,4S*,6R*)-N-(4-Isopropoxyphenyl)-2-[(1-methyl-1H-imidazol-4-yl)sulfonyl]-2-azabicyclo[2.2.2]octane-6-carboxamide | 268 |
| 42 | (1R*,4S*,6R*)-2-(Butylsulfonyl)-N-(3-cyclopropyl-1H-pyrazol-5-yl)-2-azabicyclo[2.2.2]octane-6-carboxamide | 155 |
| 47 | (1R*,4S*,6R*)-N-(5-Isopropoxypyridin-2-yl)-2-(pyridin-2-ylsulfonyl)-2-azabicyclo[2.2.2]octane-6-carboxamide | 19 |
| 48 | (1R*,4S*,6R*)-N-(5-isopropoxypyridin-2-yl)-2-[(1-methyl-1H-imidazol-4-yl)sulfonyl]-2-azabicyclo[2.2.2]octane-6-carboxamide | 159 |
| 64 | 2-Methoxy-N-{[3-phenyl-1-(pyridin-2-ylsulfonyl)piperidin-3-yl]methyl}benzamide | 20 |
| 73 | 4-Isopropoxy-N-{[3-phenyl-1-(pyridin-2-ylsulfonyl)piperidin-3-yl]methyl}benzamide | 3.7 |
| 74 | 4-Isopropoxy-N-({1-[(1-methyl-1H-imidazol-4-yl)sulfonyl]-3-phenylpiperidin-3-yl}methyl)benzamide | 17.4 |
| 76 | 5-Isopropoxy-N-{[3-phenyl-1-(propylsulfonyl)piperidin-3-yl]methyl}pyridine-2-carboxamide | 44 |
| 78 | 5-Isopropoxy-N-{[3-phenyl-1-(pyridin-2-ylsulfonyl)piperidin-3-yl]methyl}pyridine-2-carboxamide | 14 |

TABLE 1-continued

| Example Number | Name | IC$_{50}$ (nM) |
|---|---|---|
| 79 | 5-Isopropoxy-N-({1-[(1-methyl-1H-imidazol-4-yl)sulfonyl]-3-phenylpiperidin-3-yl}methyl)pyridine-2-carboxamide | 49 |
| 81 | 4-Isopropoxy-N-{[3-methyl-1-(phenylsulfonyl)piperidin-3-yl]methyl}benzamide | 51 |
| 82 | 4-Isopropoxy-N-{[3-methyl-1-(pyridin-2-ylsulfonyl)piperidin-3-yl]methyl}benzamide | 60 |
| 85 | N-{[3-Ethyl-1-(pyridin-2-ylsulfonyl)piperidin-3-yl]methyl}-4-isopropoxybenzamide | 14 |
| 86 | N-((3-Ethyl-1-[(1-methyl-1H-imidazol-4-yl)sulfonyl]piperidin-3-yl}methyl)-4-isopropoxybenzamide | 284 |
| 98 | 3-Isobutyl-N-{1-[(1-methyl-1H-imidazol-4-yl)sulfonyl]-3-phenylpiperidin-3-yl}methyl)-1H-pyrazole-5-carboxamide | 12 |
| 103 | 3-Ethyl-N-(5-isopropoxypyridin-2-yl)-1-[(1-methyl-1H-imidazol-4-yl)sulfonyl]piperidine-3-carboxamide | 35 |
| 104 | 3-Ethyl-N-(5-isopropoxy-1H-pyrazol-3-yl)-1-[(1-methyl-1H-imidazol-4-yl)sulfonyl]piperidine-3-carboxamide | 38 |
| 105 | (1R*,4S*,6R*)-N-(5-Isopropoxy-1H-pyrazol-3-yl)-2-[(1-methyl-1H-imidazol-4-yl)sulfonyl]-2-azabicyclo[2.2.2]octane-6-carboxamide | 132 |

A compound according to the present invention can be orally or parenterally administered, and can be prepared into a suitable administration form to provide a preventive or remedy for diseases such as cardiovascular disease, including, for example, hypertension, angina, heart failure, myocardial infarction, stroke, claudication, diabetic nephropathy, diabetic retinopathy, failing vision, electrolyte abnormalities, and atherosclerosis; central neurologic disease, including, for example, bulimia, and diabetic neuropathy; metabolic disease, including, for example, metabolic syndrome, obesity, diabetes mellitus, insulin resistance, hyperlipidemia, hypercholesteremia, neutral fat hyperlipaemia, dyslipidemia, non-alcoholic fatty liver, abnormal hormone secretion, gout, and fatty liver; reproductive disease, including, for example, menstrual disturbance, and sexual dysfunction; digestive disease, including liver dysfunction, pancreatitis, cholecystitis, and gastroesophageal reflux; respiratory disease, including obesity-hypoventilation syndrome (Pickwickian syndrome), and sleep apnea; bacterial, fungal, or parasitic infectious disease; malignant neoplasm; and inflammatory disease, including arthritis, and skin ulcer.

In one aspect, the present invention provides a method of treatment or prevention of disease, illness, or conditions attributed to LCE abnormalities, wherein a therapeutically or prophylactically effective amount a compound of the present invention is administered to a subject in need thereof.

In another aspect, the present invention provides a method of treatment or prevention of metabolic syndrome, fatty liver, hyperlipidemia, dyslipidemia, non-alcoholic fatty liver, obesity, diabetes mellitus, bulimia, malignant neoplasm, or infectious disease, wherein a therapeutically or prophylactically effective amount a compound of the present invention is administered to a subject in need thereof.

In another aspect, the present invention provides a method of treatment or prevention of diabetes mellitus, wherein a therapeutically or prophylactically effective amount a compound of the present invention is administered to a subject in need thereof.

In another aspect, the present invention provides a method of treatment or prevention of obesity, wherein a therapeutically or prophylactically effective amount a compound of the present invention is administered to a subject in need thereof.

In another aspect, the present invention provides a method of treatment or prevention of an obesity-related disease selected from the group consisting of overeating, bulimia, hypertension, rise in plasma insulin level, insulin resistance, hyperlipidemia, endometrial cancer, breast cancer, prostate cancer, colon cancer, kidney cancer, osteoarthritis, obstructive sleep apnea syndrome, heart disease, abnormal cardiac rhythm, cardiac arrhythmia, myocardial infarction, congestive heart failure, coronary heart disease, sudden death, stroke, polycystic ovarian disease, craniopharingioma, metabolic syndrome, insulin resistance syndrome, sexual and reproductive dysfunction, infertility, hypogonadism, hirsutism, obesity-related gastroesophageal reflux, obesity-hypoventilation syndrome (Pickwickian syndrome), inflammation, systemic vasculitis, atherosclerosis, hypercholesteremia, hyperuricemia, lower back pain, inflammation, systemic vasculitis, atherosclerosis, hypercholesteremia, hyperuricemia, lower back pain, cholecystopathy, gout, constipation, irritable bowel syndrome, inflammatory bowel syndrome, hearthypertrophy, and left ventricle hypertrophy, wherein a therapeutically or prophylactically effective amount a compound of the present invention is administered to a subject in need thereof.

In another aspect, the present invention provides a method of treatment or prevention of hyperlipidemia or dyslipidemia, wherein a therapeutically or prophylactically effective amount a compound of the present invention is administered to a subject in need thereof.

In another aspect, the present invention provides a caloric intake method, wherein a therapeutically or prophylactically effective amount a compound of the present invention is administered to a subject in need thereof.

In another aspect, the present invention provides a method for reducing food intake, wherein a therapeutically or prophylactically effective amount a compound of the present invention is administered to a subject in need thereof.

In another aspect, the present invention provides a method for increasing satiety, wherein a therapeutically or prophylactically effective amount a compound of the present invention is administered to a subject in need thereof.

In another aspect, the present invention provides a method for reducing appetite, wherein a therapeutically or prophylactically effective amount a compound of the present invention is administered to a subject in need thereof.

The present invention also relates to a method of treatment or prevention of obesity, wherein a compound according to the present invention is administered in combination with a therapeutically or prophylactically effective amount of other drugs known to be useful for the treatment or prevention of the conditions to be treated or prevented.

The present invention also relates to a method of treatment or prevention of diabetes mellitus, wherein a compound according to the present invention is administered in combination with a therapeutically or prophylactically effective amount of other drugs known to be useful for the treatment or prevention of the conditions to be treated or prevented.

The present invention also relates to a method of treatment or prevention of hyperlipidemia or dyslipidemia, wherein a compound (I) according to the present invention or a pharmaceutically acceptable salt thereof is administered in combination with a therapeutically or prophylactically effective amount of other drugs known to be useful for the treatment or prevention of the conditions to be treated or prevented.

In another aspect, the present invention provides a pharmaceutical composition which contains a compound according to the present invention, and a pharmaceutically acceptable carrier.

In another aspect, the present invention relates to a compound of the present invention used as a medicament.

In another aspect, the present invention relates to use of a compound of the present invention for the production of medicaments useful for the treatment, prevention, or suppression of the LCE-associated disease.

In another aspect, the present invention relates to use of a compound of the present invention for the production of medicaments useful for the treatment or prevention of metabolic syndrome, hyperlipidemia, dyslipidemia, non-alcoholic fatty liver, obesity, diabetes mellitus, bulimia, malignant neoplasm, or infectious disease in a subject in need thereof.

In another aspect, the present invention relates to use of a compound of the present invention for the production of medicaments useful for the treatment or prevention of obesity in a subject in need thereof.

In another aspect, the present invention relates to use of a compound of the present invention for the production of medicaments useful for the treatment or prevention of diabetes mellitus in a subject in need thereof.

In another aspect, the present invention relates to use of a compound of the present invention for the production of medicaments useful for the treatment or prevention of hyperlipidemia or dyslipidemia in a subject in need thereof.

In another aspect, the present invention relates to use of a therapeutically effective amount of a compound of the present invention, and a therapeutically effective amount of a drug or a pharmaceutically acceptable salt thereof selected from the group consisting of insulin resistance improving agent, insulin analogue, sulfonylureas, α-glucosidase inhibitor, dipeptidyl peptidase 4 (DPP-4 or DP-IV) inhibitor, glucagon-like peptide 1 (GLP-1) agonist, HMG-CoA reductase inhibitor, serotonin-like substance, β3-adrenaline receptor agonist, neuropeptide Y1 antagonist, neuropeptide Y2 agonist, neuropeptide Y5 antagonist, pancreatic lipase inhibitor, cannabinoid CB1 receptor antagonist or inverse agonist, melanin concentrating hormone receptor agonist, melanocortin 4 receptor agonist, bombesin receptor subtype-3 agonist, ghrelin antagonist, PYY, $PYY_{3-36}$, and NK-1 antagonist, wherein the use is for the production of medicaments useful for the treatment, control, or prevention of obesity, diabetes mellitus, diabetes mellitus-related disease, or obesity-related disease in a subject in need thereof.

In another aspect, the present invention relates to simultaneous or separate use of a therapeutically effective amount of a compound of the present invention, and a therapeutically effective amount of a drug or a pharmaceutically acceptable salt thereof selected from the group consisting of insulin resistance improving agent, insulin analogue, sulfonylureas, α-glucosidase inhibitor, dipeptidyl peptidase 4 (DPP-4 or DP-IV) inhibitor, glucagon-like peptide 1 (GLP-1) agonist, HMG-CoA reductase inhibitor, serotonin-like substance, β3-adrenaline receptor agonist, neuropeptide Y1 antagonist, neuropeptide Y2 agonist, neuropeptide Y5 antagonist, pancreatic lipase inhibitor, cannabinoid CB1 receptor antagonist or inverse agonist, melanin concentrating hormone receptor agonist, melanocortin 4 receptor agonist, bombesin receptor subtype-3 agonist, ghrelin antagonist, PYY, $PYY_{3-36}$, and NK-1 antagonist, for the production of medicaments useful for the treatment or prevention of obesity, diabetes mellitus, diabetes mellitus-related disease, or obesity-related disease.

In another aspect, the present invention relates to a combined preparation product for simultaneous, separate, or successive use in obesity, diabetes mellitus, diabetes mellitus-related disease, or obesity-related disease, wherein the preparation includes a therapeutically effective amount of a compound of the present invention, and a therapeutically effective amount of a drug or a pharmaceutically acceptable salt thereof selected from the group consisting of insulin resistance improving agent, insulin analogue, sulfonylureas, α-glucosidase inhibitor, dipeptidyl peptidase 4 (DPP-4 or DP-IV) inhibitor, glucagon-like peptide 1 (GLP-1) agonist, HMG-CoA reductase inhibitor, serotonin-like substance, β3-adrenaline receptor agonist, neuropeptide Y1 antagonist, neuropeptide Y2 agonist, neuropeptide Y5 antagonist, pancreatic lipase inhibitor, cannabinoid CB1 receptor antagonist or inverse agonist, melanin concentrating hormone receptor agonist, melanocortin 4 receptor agonist, bombesin receptor subtype-3 agonist, ghrelin antagonist, PYY, $PYY_{3-36}$, and NK-1 antagonist.

In another aspect, the present invention relates to use of a therapeutically effective amount of a compound of the present invention, and a therapeutically effective amount of a drug or a pharmaceutically acceptable salt thereof selected from the group consisting of simvastatin, mevastatin, ezetimibe, atorvastatin, sitagliptin, metformin, sibutramine, orlistat, Qnexa (trade name), and phentermine, wherein the use is for the production of medicaments useful for the treatment, control, or prevention of obesity, diabetes mellitus, diabetes mellitus-related disease, or obesity-related disease in a subject in need thereof.

In clinical use of a compound of the present invention, the compound may be administered after being prepared into various preparations by addition of pharmaceutically acceptable additives, depending upon the administration form. In this case, a variety of additives commonly used in the field of pharmaceuticals can be used. Examples include gelatin, lactose, sucrose, titanium oxide, starch, microcrystalline cellulose, methylated cellulose, hydroxypropylmethyl cellulose, carboxymethyl cellulose, cornstarch, microcrystalline wax, white vaseline, magnesium aluminometasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinyl pyrrolidone, magnesium stearate, palmitoleic acid, light anhydrous silicic acid, talc, vegetable oil, benzyl alcohol, gum arabic, propylene glycol, polyalkylene glycol, cyclodextrin, and hydroxypropylcyclodextrin.

Examples of the dosage form prepared as a mixture with the additive include: solid preparations such as a tablet, a capsule formulation, a granule, a powder, and a suppository; and liquid preparations such as a syrup, an elixir, and an injection. These can be prepared according to methods commonly used in the field of pharmaceuticals. The liquid preparation may be prepared by being dissolved or suspended in water or other suitable media before use. Specifically, the injection may be prepared by being dissolved or suspended in physiological saline or glucose solution as required, and may further include buffer or preservative.

The compound of the invention is effective for plants and animals in need of treatment with the compound, including humans and other mammals. Preferred examples of mammals are humans, and they may be male or female. The mammals other than humans are, for example, companion animals such as dogs, cats, and the like. The compound of the invention is also effective for obesity or obesity-related diseases in such dogs, cats, and the like. Whether treatment with the compound of the invention is necessary can be readily determined by an ordinary physician, veterinarian, or clinician.

In clinical use of a compound according to the present invention for example, the dose and dosing frequency vary depending on such factors as the sex, age, and body weight of a patient, severity of symptoms, and the type and range of intended effect. Generally, in oral administration, the daily dose is preferably 0.01 to 100 mg/kg, more preferably 0.03 to 1 mg/kg per adults, as a single dose or divided doses. In the case of parenteral administration, the daily dose is preferably 0.001 to 10 mg/kg, more preferably 0.001 to 0.1 mg/kg, even more preferably 0.01 to 0.1 mg/kg, given as a single dose or divided doses.

A tablet for oral administration preferably contains 1.0 to 1,000 mg of active ingredient. Specifically, in order to allow for adjustment of the therapeutic dose according to the symptoms of the patient to be treated, tablets containing 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, or 1,000.0 mg of active ingredient are preferable. The compound may be given 1 to 4 times a day, preferably 1 or 2 times a day.

In the case where the compound according to the invention is applied to the treatment or prevention of obesity and/or diabetes and/or hyperlipidemia and/or dyslipidemia and/or non-alcoholic fatty liver or other diseases, when the daily dosage of the compound according to the invention is about 0.1 mg to about 100 mg per kg of body weight of animal, more preferably, when the application is performed by a single administration or a divided administration of two to six times per day, or it is performed with a sustained-release preparation, a sufficient result can be generally obtained. For most large mammals, the total daily dosage is from about 1.0 mg to about 1000 mg, preferably from about 1 mg to about 50 mg. In the case of an adult having a body weight of 70 kg, generally, the total daily dosage is presumably from about 7 mg to about 350 mg. The prescription of this dosage can be adjusted for obtaining a maximum therapeutic effect.

Ordinary internists, veterinarians, or clinicians would be able to readily decide and process the effective therapeutic dose of drug necessary for the treatment, prevention, inhibition, suppression, or arrest of disease progression.

The preparation may contain 1.0 to 100 weight %, preferably 1.0 to 60 weight % of a compound of the present invention with respect to the total of the drug. The preparation may further contain other therapeutically effective compounds.

A compound according to the present invention can be used in combination with other agents useful for the care of diseases such as cardiovascular disease, including hypertension, angina, heart failure, myocardial infarction, stroke, claudication, diabetic nephropathy, diabetic retinopathy, failing vision, electrolyte abnormalities, and atherosclerosis; central neurologic disease, including, for example, bulimia, and diabetic neuropathy; metabolic disease, including, for example, metabolic syndrome, obesity, diabetes mellitus, insulin resistance, hyperlipidemia, hypercholesteremia, neutral fat hyperlipaemia, dyslipidemia, non-alcoholic fatty liver, abnormal hormone secretion, gout, and fatty liver; reproductive disease, including, for example, menstrual disturbance, and sexual dysfunction; digestive disease, including liver dysfunction, pancreatitis, cholecystitis, and gastroesophageal reflux; respiratory disease, including obesity-hypoventilation syndrome (Pickwickian syndrome), and sleep apnea; bacterial, fungal, or parasitic infectious disease; malignant neoplasm; and inflammatory disease, including arthritis, and skin ulcer. The individual components of such combinations may be administered as a single or divided preparation, either simultaneously or at different times during care. That is, the present invention should be construed as being inclusive of all administrations taking place simultaneously or at different times, and "administration", as that term is used herein, should be construed as such. In principle, a combination of a compound of the present invention with other agents useful for the care of various diseases includes combinations with any pharmaceutical preparations useful for the care of the diseases exemplified above.

The combination is inclusive of combinations containing a composition of the present invention and one or more other active substances. There are many examples of a combination including a composition of the present invention and one or more active substances selected from the therapeutic drugs for the diseases exemplified above. For example, for the treatment, control, and prevention of metabolic syndrome, it is beneficial to combine a composition of the present invention with one or more active substances selected from a hyperlipidemia remedy, a lipid lowering drug, and an anti-diabetes mellitus drug. A composition including an anti-obesity drug or anti-hypertension drug in addition to the anti-diabetes mellitus drug and/or hyperlipidemia remedy or lipid lowering drug is particularly beneficial because it provides synergy in the treatment, control, or prevention of metabolic syndrome.

Examples of the drugs that can be combined with a drug of the present invention include: ACAT inhibitor, α blocker, aldose reductase inhibitor, α amylase inhibitor, angiotensin converting enzyme inhibitor, angiotensin receptor antagonist, anion-exchange resin, appetite inhibitor, antioxidant, anti-platelet agent, β blocker, biguanide drug, calcium antagonist, CB1 receptor inverse agonist/antagonist, CETP inhibitor, cholesterol absorption inhibitor, DGAT inhibitor, DP-IV inhibitor, diuretic, eicosapentaenoic acid, endothelin antagonist, FLAP inhibitor, FXR modulator, ghrelin antagonist, GLP-1 agonist, GLP-1 secreting agent, glucagon antagonist, glucokinase activator, glucocorticoid receptor ligand, a glycosidase inhibitor, GPAT inhibitor, histamine H3 receptor ligand, HMG-CoA reductase inhibitor, HSD inhibitor, insulin and its analogues, kinase inhibitor (such as VEGF inhibitor and PDGF inhibitor), leptin, lipase inhibitor, 5-LO inhibitor, LXR ligand, melanocortin agonist, MCH antagonist, MTTP inhibitor, orexin antagonist, opioid antagonist, neuropeptide Y antagonist, nicotinic acid agonist, PPAR ligand, PTP-1B inhibitor, SCD-1 inhibitor, serotonin transporter inhibitor, SGLT inhibitor, SUR ligand, thyroid hormone agonist, UCP activator, and VPAC receptor agonist.

Advantage of the Invention

A compound according to the present invention has an excellent LCE inhibiting effect, and is therefore useful as a remedy for a variety of diseases involving LCE, for example, such as cardiovascular disease, neurologic disease, metabolic disease, reproductive disease, digestive disease, neoplasm, and infection. A compound according to the present invention is also useful as a herbicide.

BEST MODE FOR CARRYING OUT THE INVENTION

The present invention is described below in more detail based on production examples and examples. It should be noted, however, that the invention is in no way limited by the following descriptions.

EXAMPLES

In thin-layer chromatography, a Silica gel$_{60}$F$_{254}$ (Merck) was used as the plate, and the detection was made using a UV detector. As the column silica gel, Wakogel™ C-300 or C-200 (Wako Pure Chemical Industries, Ltd.), and FLASH+cartridge (Biotage) or Chromatorex (Fuji Silysia Chemical) were used. MS spectra were measured using ZQ 2000 (Waters). In the measurement of NMR spectra, dimethyl sulfoxide was used as the internal reference when using a deuterated dimethyl sulfoxide solution, and measurements were made using a JNM-AL 400 (JEOL), Mercury 400 (400 MHz; Varian), or Inova 400 (400 MHz; Varian) spectrometer. All $\delta$ values are given in ppm.

The meaning of the abbreviations used in the NMR measurement is as follows.
S: Singlet
d: Doublet
dd: Double doublet
t: Triplet
dt: Double triplet
q: Quartet
m: Multiplet
br: Broad
J: Coupling constant
Hz: Hertz
DMSO-d$_6$: Deuterated dimethyl sulfoxide In the following, (1R*,4S*,6R*) means a 1:1 mixture of (1R,4S,6R) and (1S,4R,6S), and (1R*,2R*,5R*) means a 1:1 mixture of (1R,2R,5R) and (1S,2S,5S). (1R,4S,6R) or (1S,4R,6S) means one of the enantiomers (1R,4S,6R) and (1S,4R,6S).

Reference Example 1

Synthesis of 1-(Butyl sulfonyl)-N-(4-isopropoxyphenyl)piperidine-3-carboxamide (1) Synthesis of 1-(Butylsulfonyl)piperidine-3-carboxylic Acid 1N-sodium hydroxide aqueous solution (4.1 mL) was added to nipecotic acid (500 mg, 3.87 mmol), and, under ice-cooling, butanesulfonylchloride (0.98 mL, 7.74 mmol) was added dropwise. The mixture was raised to room temperature, and stirred for 15 hours. The reaction mixture was then extracted with chloroform. The organic layer was collected, dried over magnesium sulfate, and concentrated under reduced pressure. The resulting residue was then purified using silica gel column chromatography to obtain the target (354 mg, 37%).

(2) Synthesis of Title Compound 1-(3-dimethylaminopropyl)-3-ethylcarbodiimide hydrochloride (57.5 mg, 0.3 mmol) was added to a pyridine (5 mL) solution of the compound (50 mg, 0.2 mmol) synthesized in (1) and 4-isopropoxyaniline (0.061 mg, 0.4 mmol), and the mixture was stirred at room temperature for 3 hours. The reaction mixture was concentrated under reduced pressure, and, after addition of ethyl acetate, washed once with 1N-sodium hydroxide solution, and once with saturated brine. The organic layer was dried over magnesium sulfate, and concentrated under reduced pressure. The resulting residue was then purified using silica gel column chromatography to obtain the title compound (33 mg, 43%).

$^1$H-NMR (400 MHz, CDCl$_3$, $\delta$): 0.95 (3H, t, J=7.3 Hz), 1.31 (6H, d, J=5.9 Hz), 1.40-1.51 (2H, m), 1.65-2.02 (6H, m), 2.54-2.63 (1H, m), 2.90-2.98 (2H, m), 2.99-3.08 (1H, m), 3.21-3.33 (1H, m), 3.53-3.64 (1H, m), 3.72-3.79 (1H, m), 4.44-4.54 (1H, m), 6.81-6.87 (2H, m), 7.39-7.45 (2H, m), 7.63 (1H, br s).

ESI-MS (m/e): 383.1 [M+H]$^+$

Reference Example 2

Synthesis of N-(4-Isopropoxyphenyl)-1-(phenylsulfonyl)piperidine-3-carboxamide

The title compound was synthesized as in Reference Example 1, using benzenesulfonyl chloride as the raw material.

1H-NMR (400 MHz, CDCl3, $\delta$): 1.31 (6H, d, J=5.9 Hz), 1.68-1.91 (4H, m), 2.58-2.71 (2H, m), 2.83-2.93 (1H, m), 3.41-3.51 (1H, m), 3.56-3.66 (1H, m), 4.45-4.55 (1H, m), 6.82-6.87 (2H, m), 7.41-7.46 (2H, m), 7.53-7.58 (2H, m), 7.60-7.65 (1H, m), 7.69 (1H, br s), 7.75-7.80 (2H, m).

ESI-MS (m/e): 403.2 [M+H]$^+$

Reference Example 3

Synthesis of 2-Methoxy-N-{[1-(phenylsulfonyl)piperidin-3-yl]methyl}benzamide

The title compound was synthesized as in Example 13, using the title compound of Production Example 7 and benzenesulfonyl chloride as the raw material.

1H-NMR (400 MHz, CDCl3, $\delta$): 1.11-1.23 (1H, m), 1.58-1.69 (1H, m), 1.70-1.84 (2H, m), 1.96-2.10 (1H, m), 2.45-2.53 (1H, m), 2.59-2.67 (1H, m), 3.31-3.43 (2H, m), 3.46-3.54 (2H, m), 4.02 (3H, s), 6.97-7.03 (1H, m), 7.05-7.12 (1H, m), 7.42-7.63 (4H, m), 7.72-7.77 (2H, m), 7.96-8.05 (1H, m), 8.16-8.22 (1H, m).

ESI-MS (m/e): 389.0 [M+H]$^+$

Example 1

Synthesis of (1R*,4S*,6R*)-2-(Butyl sulfonyl)-N-(4-isopropoxyphenyl)-2-azabicyclo[2.2.2]octane-6-carboxamide The title compound was synthesized as in Reference Example 1(2), using the title compound of Production Example 1 and 4-isopropoxyaniline as the raw material.

$^1$H-NMR (400 MHz, CDCl3, $\delta$): 0.96 (3H, t, J=7.3 Hz), 1.31 (6H, d, J=6.3 Hz), 1.40-1.53 (2H, m), 1.58-1.88 (6H, m), 1.93-2.04 (1H, m), 2.07-2.16 (1H, m), 2.27-2.39 (1H, m), 2.89-3.13 (3H, m), 3.22-3.31 (1H, m), 3.51-3.62 (1H, m), 3.92-3.99 (1H, m), 4.44-4.56 (1H, m), 6.81-6.87 (2H, m), 7.36-7.43 (2H, m), 7.48 (1H, br s).

ESI-MS (m/e): 409.2 [M+H]$^+$

Example 2

Synthesis of (1R*,4S*,6R*)-2-(Butyl sulfonyl)-N-phenyl-2-azabicyclo[2.2.2]octane-6-carboxamide The title compound was synthesized as in Reference Example 1(2), using the title compound of Production Example 1 and aniline as the raw material.

1H-NMR (400 MHz, CDCl3, δ): 0.88-1.01 (3H, m), 1.40-1.52 (2H, m), 1.55-1.66 (1H, m), 1.74-1.89 (4H, m), 1.93-2.15 (3H, m), 2.28-2.37 (1H, m), 2.90-3.17 (3H, m), 3.22-3.30 (1H, m), 3.53-3.61 (1H, m), 3.94-4.01 (1H, m), 7.06-7.14 (1H, m), 7.28-7.36 (2H, m), 7.51-7.57 (2H, m), 7.82 (1H, br s).

ESI-MS (m/e): 351.2 [M+H]+

Example 3

Synthesis of (1R*,4S*,6R*)-2-(Butyl sulfonyl)-N-(4-methoxyphenyl)-2-azabicyclo[2.2.2]octane-6-carboxamide The title compound was synthesized as in Reference Example 1(2), using the title compound of Production Example 1 and 4-methoxyaniline as the raw material.

1H-NMR (400 MHz, CDCl3, δ): 0.96 (3H, t, J=7.3 Hz), 1.38-1.52 (2H, m), 1.56-1.67 (1H, m), 1.72-2.03 (6H, m), 2.07-2.16 (1H, m), 2.27-2.36 (1H, m), 2.92-3.13 (3H, m), 3.23-3.31 (1H, m), 3.51-3.59 (1H, m), 3.79 (3H, s), 3.93-3.98 (1H, m), 6.81-6.89 (2H, m), 7.39-7.47 (2H, m), 7.66 (1H, br s).

ESI-MS (m/e): 381.1 [M+H]+

Example 4

Synthesis of (1R*,4S*,6R*)-2-(Butyl sulfonyl)-N-(4-fluorophenyl)-2-azabicyclo[2.2.2]octane-6-carboxamide The title compound was synthesized as in Reference Example 1(2), using the title compound of Production Example 1 and 4-fluoroaniline as the raw material.

1H-NMR (400 MHz, CDCl3, δ): 0.96 (3H, t, J=7.3 Hz), 1.38-1.52 (2H, m), 1.55-1.68 (1H, m), 1.73-1.90 (4H, m), 1.92-2.15 (3H, m), 2.27-2.37 (1H, m), 2.87-3.16 (3H, m), 3.21-3.30 (1H, m), 3.50-3.59 (1H, m), 3.89-4.00 (1H, m), 6.95-7.06 (2H, m), 7.45-7.54 (2H, m), 7.89 (1H, br s).

ESI-MS (m/e): 369.1 [M+H]+

Example 5

Synthesis of (1R*,4S*,6R*)-2-(Butyl sulfonyl)-N-[4-(trifluoromethyl)phenyl]-2-azabicyclo[2.2.2]octane-6-carboxamide The title compound was synthesized as in Reference Example 1(2), using the title compound of Production Example 1 and 4-trifluoromethylaniline as the raw material.

1H-NMR (400 MHz, CDCl3, δ): 0.96 (3H, t, J=7.3 Hz), 1.40-1.52 (2H, m), 1.58-2.00 (7H, m), 2.11-2.17 (1H, m), 2.27-2.37 (1H, m), 2.92-3.08 (2H, m), 3.11-3.18 (1H, m), 3.22-3.30 (1H, m), 3.55-3.64 (1H, m), 3.94-4.00 (1H, m), 7.53-7.61 (2H, m), 7.65-7.73 (2H, m), 8.09 (1H, br s).

ESI-MS (m/e): 419.2 [M+H]+

Example 6

Synthesis of (1R*,4S*,6R*)-2-(Butyl sulfonyl)-N-(4-methylphenyl)-2-azabicyclo[2.2.2]octane-6-carboxamide The title compound was synthesized as in Reference Example 1(2), using the title compound of Production Example 1 and 4-methylaniline as the raw material.

1H-NMR (400 MHz, CDCl3, δ): 0.96 (3H, t, J=7.3 Hz), 1.41-1.53 (2H, m), 1.75-1.88 (6H, m), 1.92-2.02 (1H, m), 2.09-2.15 (1H, m), 2.28-2.36 (4H, m), 2.91-3.12 (3H, m), 3.24-3.29 (1H, m), 3.54-3.60 (1H, m), 3.93-3.97 (1H, m), 7.09-7.15 (2H, m), 7.38-7.43 (2H, m), 7.54 (1H, br s).

ESI-MS (m/e): 365.3 [M+H]+

Example 7

Synthesis of (1R*,4S*,6R*)-2-(Butyl sulfonyl)-N-(4-isopropylphenyl)-2-azabicyclo[2.2.2]octane-6-carboxamide The title compound was synthesized as in Reference Example 1(2), using the title compound of Production Example 1 and 4-isopropylaniline as the raw material.

1H-NMR (400 MHz, CDCl3, δ): 0.96 (3H, t, J=7.3 Hz), 1.23 (6H, d, J=6.8 Hz), 1.40-1.52 (2H, m), 1.75-1.89 (5H, m), 1.93-2.02 (1H, m), 2.08-2.15 (1H, m), 2.25-2.40 (1H, m), 2.77-3.13 (4H, m), 3.22-3.32 (1H, m), 3.52-3.61 (1H, m), 3.91-3.99 (1H, m), 7.13-7.20 (2H, m), 7.40-7.48 (2H, m), 7.56 (1H, br s).

ESI-MS (m/e): 393.3 [M+H]+

Example 8

Synthesis of (1R*,4S*,6R*)-N-[4-(Benzyloxy)phenyl]-2-(butyl sulfonyl)-2-azabicyclo[2.2.2]octane-6-carboxamide The title compound was synthesized as in Reference Example 1(2), using the title compound of Production Example 1 and 4-benzyloxyaniline as the raw material.

1H-NMR (400 MHz, CDCl3, δ): 0.96 (3H, t, J=7.3 Hz), 1.41-1.50 (2H, m), 1.74-1.88 (6H, m), 1.93-2.01 (1H, m), 2.08-2.15 (1H, m), 2.26-2.37 (1H, m), 2.91-3.04 (2H, m), 3.05-3.11 (1H, m), 3.24-3.30 (1H, m), 3.54-3.60 (1H, m), 3.93-3.97 (1H, m), 5.05 (2H, s), 6.90-6.95 (2H, m), 7.30-7.46 (7H, m), 7.54 (1H, br s).

ESI-MS (m/e): 457.2 [M+H]+

Example 9

Synthesis of (1R*,4S*,6R*)-N-(4-Benzylphenyl)-2-(butyl sulfonyl)-2-azabicyclo[2.2.2]octane-6-carboxamide The title compound was synthesized as in Reference Example 1(2), using the title compound of Production Example 1 and 4-benzylaniline as the raw material.

1H-NMR (400 MHz, CDCl3, δ): 0.96 (3H, t, J=7.2 Hz), 1.40-1.50 (2H, m), 1.55-2.02 (8H, m), 2.09-2.14 (1H, m), 2.26-2.35 (1H, m), 2.90-3.13 (3H, m), 3.23-3.30 (1H, m), 3.54-3.61 (1H, m), 3.94 (2H, s), 7.10-7.22 (6H, m), 7.41-7.48 (2H, m), 7.63 (1H, br s).

ESI-MS (m/e): 441.2 [M+H]+

Example 10

Synthesis of (1R*,4S*,6R*)-2-(Butyl sulfonyl)-N-(4-phenoxyphenyl)-2-azabicyclo[2.2.2]octane-6-carboxamide The title compound was synthesized as in Reference Example 1(2), using the title compound of Production Example 1 and 4-phenoxyaniline as the raw material.

1H-NMR (400 MHz, CDCl3, δ): 0.97 (3H, t, J=7.4 Hz), 1.21-1.29 (1H, m), 1.40-1.51 (2H, m), 1.59-1.89 (5H, m), 1.92-2.04 (1H, m), 2.09-2.16 (1H, m), 2.25-2.38 (1H, m), 2.90-3.15 (3H, m), 3.22-3.32 (1H, m), 3.55-3.61 (1H, m), 3.94-3.99 (1H, m), 6.94-7.02 (4H, m), 7.05-7.11 (1H, m), 7.30-7.35 (2H, m), 7.47-7.54 (2H, m), 7.72 (1H, br s).

ESI-MS (m/e): 443.2 [M+H]$^+$

Example 11

Synthesis of (1R*,4S*,6R*)-2-(Butyl sulfonyl)-N-[4-(trifluoromethoxy)phenyl]-2-azabicyclo[2.2.2]octane-6-carboxamide The title compound was synthesized as in Reference Example 1(2), using the title compound of Production Example 1 and 4-trifluoromethoxyaniline as the raw material.

1H-NMR (400 MHz, CDCl3, δ): 0.96 (3H, t, J=7.3 Hz), 1.38-1.52 (2H, m), 1.57-1.69 (1H, m), 1.73-1.88 (5H, m), 1.91-1.99 (1H, m), 2.09-2.17 (1H, m), 2.28-2.37 (1H, m), 2.90-3.15 (3H, m), 3.23-3.31 (1H, m), 3.56-3.61 (1H, m), 3.93-3.97 (1H, m), 7.14-7.20 (2H, m), 7.55-7.61 (2H, m), 7.95 (1H, br s).

ESI-MS (m/e): 435.2 [M+H]$^+$

Example 12

Synthesis of (1R*,4S*,6R*)-2-(Butyl sulfonyl)-N-(2-methoxyphenyl)-2-azabicyclo[2.2.2]octane-6-carboxamide The title compound was synthesized as in Reference Example 1(2), using the title compound of Production Example 1 and 2-methoxyaniline as the raw material.

1H-NMR (400 MHz, CDCl3, δ): 0.97 (3H, t, J=7.3 Hz), 1.42-1.51 (2H, m), 1.55-1.65 (1H, m), 1.75-1.91 (5H, m), 1.97-2.07 (1H, m), 2.09-2.15 (1H, m), 2.21-2.34 (1H, m), 2.87-3.05 (2H, m), 3.11-3.20 (1H, m), 3.26-3.35 (1H, m), 3.51-3.59 (1H, m), 3.89 (3H, s), 3.97-4.05 (1H, m), 6.86-6.90 (1H, m), 6.92-6.98 (1H, m), 7.02-7.10 (1H, m), 7.86 (1H, br s), 8.26-8.35 (1H, m).

ESI-MS (m/e): 381.2 [M+H]$^+$

Example 13

Synthesis of (1R*,4S*,6R*)-2-[(2,5-Difluorophenyl)sulfonyl]-N-(4-isopropoxyphenyl)-2-azabicyclo[2.2.2]octane-6-carboxamide Triethylamine (0.051 mL, 0.368 mmol) and 2,5-difluorobenzenesulfonyl chloride (0.0162 mL, 0.12 mmol) were added to a chloroform (1 mL) solution of the title compound (30 mg, 0.092 mmol) of Production Example 2, and the mixture was stirred at room temperature for 19 hours. The reaction mixture was then washed once with a saturated sodium hydrogen carbonate aqueous solution, dried over magnesium sulfate, and concentrated under reduced pressure. The resulting residue was then purified using silica gel column chromatography to obtain the title compound (27 mg, 63%).

1H-NMR (400 MHz, CDCl3, δ): 1.32 (6H, d, J=5.9 Hz), 1.46-1.56 (1H, m), 1.61-1.70 (1H, m), 1.73-1.91 (3H, m), 2.09-2.14 (1H, m), 2.26-2.35 (1H, m), 2.95-3.02 (1H, m), 3.36-3.42 (1H, m), 3.44-3.50 (1H, m), 4.12-4.17 (1H, m), 4.45-4.55 (1H, m), 6.81-6.88 (2H, m), 7.18-7.31 (2H, m), 7.36-7.43 (3H, m), 7.61-7.67 (1H, m).

ESI-MS (m/e): 465.2 [M+H]$^+$

Example 14

Synthesis of (1R*,4S*,6R*)-N-(4-Isopropoxyphenyl)-2-(methylsulfonyl)-2-azabicyclo[2.2.2]octane-6-carboxamide The title compound was synthesized as in Example 13, using the title compound of Production Example 2 and methanesulfonyl chloride as the raw material.

1H-NMR (400 MHz, CDCl3, δ): 1.31 (6H, d, J=5.9 Hz), 1.55-1.66 (1H, m), 1.77-1.90 (3H, m), 1.93-2.03 (1H, m), 2.10-2.16 (1H, m), 2.29-2.38 (1H, m), 2.91 (3H, s), 3.02-3.10 (1H, m), 3.27-3.32 (1H, m), 3.48-3.54 (1H, m), 3.99-4.03 (1H, m), 4.44-4.54 (1H, m), 6.81-6.87 (2H, m), 7.37-7.43 (2H, m), 7.55 (1H, br s).

ESI-MS (m/e): 367.2 [M+H]$^+$

Example 15

Synthesis of (1R*,4S*,6R*)-2-(Ethylsulfonyl)-N-(4-isopropoxyphenyl)-2-azabicyclo[2.2.2]octane-6-carboxamide The title compound was synthesized as in Example 13, using the title compound of Production Example 2 and ethanesulfonyl chloride as the raw material.

1H-NMR (400 MHz, CDCl3, δ): 1.31 (6H, d, J=5.9 Hz), 1.37 (3H, t, J=7.3 Hz), 1.55-1.66 (1H, m), 1.75-1.89 (3H, m), 1.94-2.05 (1H, m), 2.08-2.14 (1H, m), 2.27-2.36 (1H, m), 2.94-3.11 (3H, m), 3.24-3.30 (1H, m), 3.54-3.60 (1H, m), 3.92-3.97 (1H, m), 4.44-4.55 (1H, m), 6.80-6.88 (2H, m), 7.38-7.45 (2H, m), 7.56 (1H, br s).

ESI-MS (m/e): 381.2 [M+H]$^+$

Example 16

Synthesis of (1R*,4S*,6R*)-N-(4-isopropoxyphenyl)-2-(phenylsulfonyl)-2-azabicyclo[2.2.2]octane-6-carboxamide The title compound was synthesized as in Example 13, using the title compound of Production Example 2 and benzenesulfonyl chloride as the raw material.

1H-NMR (400 MHz, CDCl3, δ): 1.28-1.38 (7H, m), 1.42-1.52 (1H, m), 1.62-1.82 (3H, m), 2.02-2.08 (1H, m), 2.17-2.27 (1H, m), 2.82-2.91 (1H, m), 3.23-3.28 (1H, m), 3.44-3.50 (1H, m), 4.03-4.08 (1H, m), 4.46-4.53 (1H, m), 6.82-6.88 (2H, m), 7.34-7.42 (3H, m), 7.52-7.57 (2H, m), 7.59-7.64 (1H, m), 7.86-7.92 (2H, m).

ESI-MS (m/e): 429.2 [M+H]$^+$

Example 17

Synthesis of (1R*,4S*,6R*)-N-(4-Isopropoxyphenyl)-2-[(4-methoxyphenyl)sulfonyl]-2-azabicyclo[2.2.2]octane-6-carboxamide The title compound was synthesized as in Example 13, using the title compound of Production Example 2 and 4-methoxybenzenesulfonyl chloride as the raw material.

1H-NMR (400 MHz, CDCl3, δ): 1.25-1.40 (7H, m), 1.43-1.53 (1H, m), 1.63-1.82 (3H, m), 1.99-2.06 (1H, m), 2.17-2.27 (1H, m), 2.84-2.93 (1H, m), 3.17-3.27 (1H, m), 3.39-3.47 (1H, m), 3.88 (3H, s), 3.99-4.05 (1H, m), 4.44-4.55 (0H, m), 6.81-6.88 (2H, m), 6.97-7.03 (2H, m), 7.36-7.42 (3H, m), 7.76-7.85 (2H, m).

ESI-MS (m/e): 459.2 [M+H]$^+$

Example 18

Synthesis of (1R*,4S*,6R*)-N-(4-Isopropoxyphenyl)-2-{[4-(trifluoromethyl)phenyl]sulfonyl}-2-azabicyclo[2.2.2]octane-6-carboxamide The title compound was synthesized as in Example 13, using the title compound of Production Example 2 and 4-trifluoromethylbenzenesulfonyl chloride as the raw material.

1H-NMR (400 MHz, CDCl3, δ): 1.24-1.37 (7H, m), 1.38-1.49 (1H, m), 1.63-1.88 (3H, m), 2.04-2.11 (1H, m), 2.20-2.29 (1H, m), 2.93-3.01 (1H, m), 3.19-3.24 (1H, m), 3.49-3.55 (1H, m), 4.08-4.16 (1H, m), 4.45-4.56 (1H, m), 6.82-6.90 (2H, m), 7.35-7.44 (3H, m), 7.76-7.84 (2H, m), 7.96-8.03 (2H, m).

ESI-MS (m/e): 497.2 [M+H]$^+$

Example 19

Synthesis of (1R*,4S*,6R*)-2-[(4-tert-Butyl phenyl)sulfonyl]-N-(4-isopropoxyphenyl)-2-azabicyclo[2.2.2]octane-6-carboxamide The title compound was synthesized as in Example 13, using the title compound of Production Example 2 and 4-tert-butylbenzenesulfonyl chloride as the raw material.

1H-NMR (400 MHz, CDCl3, δ): 1.31 (6H, d, J=5.9 Hz), 1.34 (9H, s), 1.44-1.55 (1H, m), 1.62-1.83 (3H, m), 1.94-2.05 (2H, m), 2.17-2.27 (1H, m), 2.86-2.94 (1H, m), 3.22-3.28 (1H, m), 3.42-3.48 (1H, m), 4.05-4.09 (1H, m), 4.44-4.54 (1H, m), 6.78-6.86 (2H, m), 7.36-7.42 (2H, m), 7.51-7.56 (3H, m), 7.76-7.83 (2H, m).

ESI-MS (m/e): 485.2 [M+H]$^+$

Example 20

Synthesis of (1R*,4S*,6R*)-2-[(3-Fluorophenyl)sulfonyl]-N-(4-isopropoxyphenyl)-2-azabicyclo[2.2.2]octane-6-carboxamide The title compound was synthesized as in Example 13, using the title compound of Production Example 2 and 3-fluorobenzenesulfonyl chloride as the raw material.

1H-NMR (400 MHz, CDCl3, δ): 1.26-1.39 (7H, m), 1.41-1.52 (1H, m), 1.63-1.85 (3H, m), 2.03-2.10 (1H, m), 2.20-2.29 (1H, m), 2.87-2.97 (1H, m), 3.21-3.28 (1H, m), 3.45-3.53 (1H, m), 4.04-4.10 (1H, m), 4.45-4.55 (1H, m), 6.82-6.89 (2H, m), 7.28-7.34 (1H, m), 7.36-7.43 (3H, m), 7.50-7.60 (2H, m), 7.64-7.70 (1H, m).

ESI-MS (m/e): 447.1 [M+H]$^+$

Example 21

Synthesis of (1R*,4S*,6R*)-2-[(4-Fluorophenyl)sulfonyl]-N-(4-isopropoxyphenyl)-2-azabicyclo[2.2.2]octane-6-carboxamide The title compound was synthesized as in Example 13, using the title compound of Production Example 2 and 4-fluorobenzenesulfonyl chloride as the raw material.

1H-NMR (400 MHz, CDCl3, δ): 1.23-1.38 (7H, m), 1.39-1.49 (1H, m), 1.63-1.85 (3H, m), 2.02-2.09 (1H, m), 2.19-2.28 (1H, m), 2.90-2.99 (1H, m), 3.17-3.24 (1H, m), 3.44-3.51 (1H, m), 4.03-4.10 (1H, m), 4.44-4.57 (1H, m), 6.82-6.88 (2H, m), 7.18-7.24 (2H, m), 7.37-7.45 (3H, m), 7.85-7.92 (2H, m).

ESI-MS (m/e): 447.1 [M+H]$^+$

Example 22

Synthesis of (1R*,4S*,6R*)-2-[(2-Fluorophenyl)sulfonyl]-N-(4-isopropoxyphenyl)-2-azabicyclo[2.2.2]octane-6-carboxamide The title compound was synthesized as in Example 13, using the title compound of Production Example 2 and 2-fluorobenzenesulfonyl chloride as the raw material.

1H-NMR (400 MHz, CDCl3, δ): 1.32 (6H, d, J=6.3 Hz), 1.46-1.56 (1H, m), 1.62-1.88 (4H, m), 2.05-2.12 (1H, m), 2.24-2.34 (1H, m), 2.92-3.01 (1H, m), 3.36-3.47 (2H, m), 4.12-4.16 (1H, m), 4.44-4.55 (1H, m), 6.80-6.90 (2H, m), 7.21-7.32 (2H, m), 7.36-7.44 (3H, m), 7.53-7.62 (1H, m), 7.89-7.97 (1H, m).

ESI-MS (m/e): 447.1 [M+H]$^+$

Example 23

Synthesis of (1R*,4S*,6R*)-N-(4-Isopropoxyphenyl)-2-[(3-methoxyphenyl)sulfonyl]-2-azabicyclo[2.2.2]octane-6-carboxamide The title compound was synthesized as in Example 13, using the title compound of Production Example 2 and 3-methoxybenzenesulfonyl chloride as the raw material.

1H-NMR (400 MHz, CDCl3, δ): 1.26-1.43 (7H, m), 1.46-1.60 (1H, m), 1.65-1.84 (3H, m), 2.01-2.08 (1H, m), 2.17-2.26 (1H, m), 2.75-2.83 (1H, m), 3.26-3.33 (1H, m), 3.41-3.48 (1H, m), 3.87 (3H, s), 4.02-4.07 (1H, m), 4.44-4.55 (1H, m), 6.82-6.88 (2H, m), 7.11-7.17 (1H, m), 7.30-7.34 (1H, m), 7.37-7.42 (3H, m), 7.44-7.49 (2H, m).

ESI-MS (m/e): 459.2 [M+H]$^+$

Example 24

Synthesis of (1R*,4S*,6R*)-N-(4-Isopropoxyphenyl)-2-(pyridin-3-ylsulfonyl)-2-azabicyclo[2.2.2]octane-6-carboxamide The title compound was synthesized as in Example 13, using the title compound of Production Example 2 and 3-pyridinesulfonyl chloride as the raw material.

1H-NMR (400 MHz, CDCl3, δ): 1.26-1.39 (7H, m), 1.41-1.51 (1H, m), 1.66-1.90 (3H, m), 2.04-2.11 (1H, m), 2.21-2.28 (1H, m), 2.89-2.97 (1H, m), 3.20-3.27 (1H, m), 3.47-

3.52 (1H, m), 4.09-4.16 (1H, m), 4.44-4.55 (1H, m), 6.80-6.88 (2H, m), 7.37-7.43 (2H, m), 7.45-7.53 (2H, m), 8.12-8.18 (1H, m), 8.80-8.87 (1H, m), 9.07-9.12 (1H, m).
ESI-MS (m/e): 430.1 [M+H]$^+$

Example 25

Synthesis of (1R*,4S*,6R*)-2-[(2,5-Dichloro-3-thienyl)sulfonyl]-N-(4-isopropoxyphenyl)-2-azabicyclo[2.2.2]octane-6-carboxamide The title compound was synthesized as in Example 13, using the title compound of Production Example 2 and 2,5-dichlorothiophene-3-sulfonyl chloride as the raw material.
1H-NMR (400 MHz, CDCl3, δ): 1.32 (6H, d, J=6.3 Hz), 1.49-1.85 (3H, m), 1.87-1.97 (1H, m), 2.09-2.14 (1H, m), 2.23-2.32 (1H, m), 2.91-3.01 (1H, m), 3.36-3.42 (1H, m), 3.48-3.54 (1H, m), 4.06-4.11 (1H, m), 4.45-4.55 (1H, m), 6.82-6.89 (2H, m), 7.13 (1H, s), 7.36-7.42 (2H, m).
ESI-MS (m/e): 503.2 [M+H]$^+$ Example 26

Synthesis of (1R*,4S*,6R*)-N-(4-Isopropoxyphenyl)-2-[(1-methyl-1H-imidazol-4-yl)sulfonyl]-2-azabicyclo[2.2.2]octane-6-carboxamide The title compound was synthesized as in Example 13, using the title compound of Production Example 2 and 1-methylimidazole-4-sulfonyl chloride as the raw material.
1H-NMR (400 MHz, CDCl3, δ): 1.32 (6H, d, J=6.3 Hz), 1.41-1.52 (1H, m), 1.56-1.66 (1H, m), 1.70-1.98 (3H, m), 2.00-2.05 (1H, m), 2.15-2.24 (1H, m), 2.94-3.02 (2H, m), 3.43-3.48 (1H, m), 3.80 (3H, s), 4.28-4.31 (1H, m), 4.46-4.54 (1H, m), 6.82-6.88 (2H, m), 7.46-7.52 (3H, m), 7.59-7.63 (1H, m), 8.62 (1H, br s).
ESI-MS (m/e): 433.3 [M+H]$^+$ Example 27

Synthesis of (1R*,4S*,6R*)-2-[(1,2-Dimethyl-1H-imidazol-4-yl)sulfonyl]-N-(4-isopropoxyphenyl)-2-azabicyclo[2.2.2]octane-6-carboxamide The title compound was synthesized as in Example 13, using the title compound of Production Example 2 and 1,2-dimethylimidazole-4-sulfonyl chloride as the raw material.
1H-NMR (400 MHz, CDCl3, δ): 1.32 (6H, d, J=6.3 Hz), 1.41-1.51 (1H, m), 1.57-1.67 (1H, m), 1.70-1.98 (3H, m), 2.00-2.05 (1H, m), 2.16-2.24 (1H, m), 2.41 (3H, s), 2.92-3.03 (2H, m), 3.40-3.47 (1H, m), 3.66 (3H, s), 4.26-4.31 (1H, m), 4.45-4.55 (1H, m), 6.82-6.88 (2H, m), 7.41 (1H, s), 7.48-7.54 (2H, m), 8.83 (1H, br s).
ESI-MS (m/e): 447.3 [M+H]$^+$ Example 28

Synthesis of (1R*,4S*,6R*)-2-{[2-(Acetylamino)-4-methyl-1,3-thiazol-5-yl]sulfonyl}-N-(4-isopropoxyphenyl)-2-azabicyclo[2.2.2]octane-6-carboxamide The title compound was synthesized as in Example 13, using the title compound of Production Example 2 and 2-acetamide-4-methyl-5-thiazolesulfonyl chloride as the raw material.

1H-NMR (400 MHz, CDCl3, δ): 1.32 (6H, d, J=5.9 Hz), 1.46-1.57 (1H, m), 1.64-1.95 (4H, m), 2.06-2.14 (1H, m), 2.21-2.31 (4H, m), 2.58 (3H, s), 2.89-2.97 (1H, m), 3.35-3.46 (2H, m), 4.04-4.10 (1H, m), 4.45-4.55 (1H, m), 6.82-6.87 (2H, m), 7.35 (1H, br s), 7.39-7.45 (2H, m).
ESI-MS (m/e): 507.3 [M+H]$^+$

Example 29

Synthesis of (1R*,4S*,6R*)-N-(4-Isopropoxyphenyl)-2-(2-thienylsulfonyl)-2-azabicyclo[2.2.2]octane-6-carboxamide The title compound was synthesized as in Example 13, using the title compound of Production Example 2 and thiophene-2-sulfonyl chloride as the raw material.
1H-NMR (400 MHz, CDCl3, δ): 1.32 (6H, d, J=6.3 Hz), 1.39-1.47 (1H, m), 1.51-1.84 (4H, m), 2.05-2.11 (1H, m), 2.19-2.27 (1H, m), 2.75-2.83 (1H, m), 3.34-3.48 (2H, m), 4.04-4.09 (1H, m), 4.45-4.56 (1H, m), 6.82-6.88 (2H, m), 7.13-7.16 (1H, m), 7.20 (1H, br s), 7.35-7.42 (2H, m), 7.59-7.65 (2H, m).
ESI-MS (m/e): 435.3 [M+H]$^+$ Example 30

Synthesis of (1R*,4S*,6R*)-N-(4-Isopropoxyphenyl)-2-(3-thienylsulfonyl)-2-azabicyclo[2.2.2]octane-6-carboxamide Triethylamine (0.065 mL, 0.42 mmol) and 20% palladium hydroxide-carbon catalyst (8 mg) were added to a methanol (2 mL) solution of the compound (35 mg, 0.0695 mmol) synthesized in Example 25, and the mixture was stirred for 5 hours in a hydrogen (4 atm) atmosphere. The reaction mixture was then celite filtered, and the filtrate was concentrated. The resulting residue was then purified using silica gel column chromatography to obtain the target (9.9 mg, 33%).
1H-NMR (400 MHz, CDCl3, δ): 1.25-1.42 (7H, m), 1.46-1.58 (1H, m), 1.66-1.85 (3H, m), 2.04-2.10 (1H, m), 2.19-2.27 (1H, m), 2.83-2.91 (1H, m), 3.25-3.32 (1H, m), 3.42-3.49 (1H, m), 4.04-4.09 (1H, m), 4.44-4.55 (1H, m), 6.82-6.88 (2H, m), 7.29 (1H, br s), 7.35-7.43 (3H, m), 7.44-7.48 (1H, m), 7.96-7.99 (1H, m)
ESI-MS (m/e): 435.1 [M+H]$^+$ Example 31

Synthesis of (1R*,4S*,6R*)-N-(4-Isopropoxyphenyl)-2-(propylsulfonyl)-2-azabicyclo[2.2.2]octane-6-carboxamide The title compound was synthesized as in Example 13, using the title compound of Production Example 2 and 1-propanesulfonyl chloride as the raw material.
1H-NMR (400 MHz, CDCl3, δ): 1.07 (3H, t, J=7.4 Hz), 1.31 (6H, d, J=6.1 Hz), 1.52-1.66 (1H, m), 1.75-1.91 (5H, m), 1.94-2.04 (1H, m), 2.08-2.14 (1H, m), 2.27-2.36 (1H, m), 2.88-3.02 (2H, m), 3.04-3.11 (1H, m), 3.24-3.30 (1H, m), 3.53-3.60 (1H, m), 3.92-3.98 (1H, m), 4.45-4.55 (1H, m), 6.80-6.87 (2H, m), 7.37-7.43 (2H, m), 7.53 (1H, br s).
ESI-MS (m/e): 395.1 [M+H]$^+$

Example 32

Synthesis of (1R*,4S*,6R*)-N-(4-Isopropoxyphenyl)-2-(isopropylsulfonyl)-2-azabicyclo[2.2.2]octane-6-carboxamide The title compound was synthesized as in Example 13, using the title compound of Production Example 2 and isopropylsulfonyl chloride as the raw material.
1H-NMR (400 MHz, CDCl3, δ): 1.31 (6H, d, J=6.1 Hz), 1.35-1.41 (6H, m), 1.57-1.66 (1H, m), 1.77-1.91 (3H, m), 1.94-2.04 (1H, m), 2.07-2.13 (1H, m), 2.25-2.35 (1H, m), 3.05-3.12 (1H, m), 3.14-3.22 (1H, m), 3.23-3.29 (1H, m), 3.64-3.71 (1H, m), 3.86-3.92 (1H, m), 4.45-4.53 (1H, m), 6.80-6.87 (2H, m), 7.37-7.46 (3H, m).
ESI-MS (m/e): 395.2 [M+H]+

Example 33

Synthesis of (1R*,4S*,6R*)-2-(Cyclopropylsulfonyl)-N-(4-isopropoxyphenyl)-2-azabicyclo[2.2.2]octane-6-carboxamide The title compound was synthesized as in Example 13, using the title compound of Production Example 2 and cyclopropylsulfonyl chloride as the raw material.
1H-NMR (400 MHz, CDCl3, δ): 0.92-1.07 (2H, m), 1.12-1.27 (2H, m), 1.56-1.68 (1H, m), 1.76-2.01 (4H, m), 2.06-2.14 (1H, m), 2.27-2.44 (2H, m), 3.05-3.13 (1H, m), 3.35-3.42 (1H, m), 3.48-3.54 (1H, m), 3.94-4.01 (1H, m), 4.43-4.56 (1H, m), 6.79-6.88 (2H, m), 7.38-7.45 (2H, m), 7.57 (1H, br s).
ESI-MS (m/e): 393.2 [M+H]+

Example 34

Optical resolution of (1R*,4S*,6R*)-N-(4-Isopropoxyphenyl)-2-[(1-methyl-1H-imidazol-4-yl)sulfonyl]-2-azabicyclo[2.2.2]octane-6-carboxamide The compound (60 mg, 0.138 mmol) synthesized in Example 26 was optically resolved using normal-phase chiral HPLC (CHIRALPAK AD 2 cm ⌀×25 cmL (Daicel Chemical Industries, Ltd.); mobile phase: hexane:isopropyl alcohol=60:40; flow rate: 10 ml/min; isogradient), and (1R, 4S,6R)-N-(4-isopropoxyphenyl)-2-[(1-methyl-1H-imidazol-4-yl)sulfonyl]-2-azabicyclo[2.2.2]octane-6-carboxamide (retention time: 14.2 min; 26.6 mg), and (1S, 4R,6S)-N-(4-isopropoxyphenyl)-2-[(1-methyl-1H-imidazol-4-yl)sulfonyl]-2-azabicyclo[2.2.2]octane-6-carboxamide (retention time: 30.7 min; 29.4 mg) were obtained.

Example 35

Synthesis of (1R*,2R*,5R*)-8-(Butyl sulfonyl)-N-(4-isopropoxyphenyl)-8-azabicyclo[3.2.1]octane-2-carboxamide The title compound was synthesized as in Example 13, using the title compound of Production Example 3 and 1-butanesulfonyl chloride as the raw material.
1H-NMR (400 MHz, CDCl3, δ): 0.96 (3H, t, J=7.3 Hz), 1.31 (6H, d, J=6.1 Hz), 1.40-1.52 (2H, m), 1.60-1.70 (1H, m), 1.72-1.85 (5H, m), 1.87-2.14 (4H, m), 2.20-2.31 (1H, m), 2.77-2.87 (1H, m), 2.93-3.01 (2H, m), 4.13-4.20 (1H, m), 4.31-4.39 (1H, m), 4.45-4.55 (1H, m), 6.80-6.88 (2H, m), 7.35-7.43 (3H, m).
ESI-MS (m/e): 409.1 [M+H]+

Example 36

Synthesis of (1R*,2R*,5R*)-N-(4-Isopropoxyphenyl)-8-(phenylsulfonyl)-8-azabicyclo[3.2.1]octane-2-carboxamide The title compound was synthesized as in Example 13, using the title compound of Production Example 3 and benzenesulfonyl chloride as the raw material.
1H-NMR (400 MHz, CDCl3, δ): 1.23-1.55 (8H, m), 1.58-1.68 (1H, m), 1.73-2.09 (5H, m), 2.81-2.90 (1H, m), 4.21-4.29 (1H, m), 4.38-4.44 (1H, m), 4.46-4.54 (1H, m), 6.78-6.87 (2H, m), 7.37-7.45 (2H, m), 7.46-7.53 (2H, m), 7.56-7.62 (2H, m), 7.84-7.91 (2H, m).
ESI-MS (m/e): 429.1 [M+H]+

Example 37

Synthesis of (1R*,2R*,5R*)-N-(4-Isopropoxyphenyl)-8-[(1-methyl-1H-imidazol-4-yl)sulfonyl]-8-azabicyclo[3.2.1]octane-2-carboxamide The title compound was synthesized as in Example 13, using the title compound of Production Example 3 and 1-methylimidazole-4-sulfonyl chloride as the raw material.
1H-NMR (400 MHz, CDCl3, δ): 1.31 (6H, d, J=6.1 Hz), 1.50-1.64 (2H, m), 1.69-1.89 (3H, m), 1.94-2.12 (2H, m), 2.23-2.37 (1H, m), 2.84-2.97 (1H, m), 3.75 (3H, s), 4.26-4.35 (1H, m), 4.41-4.54 (2H, m), 6.78-6.86 (2H, m), 7.38-7.46 (3H, m), 7.50 (1H, s), 7.87 (1H, s).
ESI-MS (m/e): 433.1 [M+H]+

Example 38

Synthesis of (1R*,4S*,6R*)-N-(4-Isopropoxyphenyl)-2-(pyridin-2-ylsulfonyl)-2-azabicyclo[2.2.2]octane-6-carboxamide The title compound was synthesized as in Example 13, using the title compound of Production Example 2 and pyridine-2-sulfonyl chloride as the raw material.
1H-NMR (400 MHz, CDCl3, δ): 1.32 (6H, d, J=5.9 Hz), 1.47-1.64 (2H, m), 1.69-1.85 (3H, m), 2.01-2.08 (1H, m), 2.24-2.33 (1H, m), 3.03-3.12 (1H, m), 3.25-3.32 (1H, m), 3.46-3.53 (1H, m), 4.28-4.32 (1H, m), 4.46-4.54 (1H, m), 6.82-6.89 (2H, m), 7.38-7.47 (2H, m), 7.52-7.57 (1H, m), 7.73 (1H, br s), 7.91-7.99 (1H, m), 8.02-8.07 (1H, m), 8.70-8.78 (1H, m).
ESI-MS (m/e): 430.0 [M+H]+

Example 39

Synthesis of (1R*,2R*,5R*)-N-(4-Isopropoxyphenyl)-8-(pyridin-2-ylsulfonyl)-8-azabicyclo[3.2.1]octane-2-carboxamide The title compound was synthesized as in Example 13, using the title compound of Production Example 3 and pyridine-2-sulfonyl chloride as the raw material.
1H-NMR (400 MHz, CDCl3, δ): 1.31 (6H, dd, J=5.9, 2.4 Hz), 1.43-1.81 (5H, m), 1.85-1.96 (1H, m), 1.99-2.13 (2H, m), 2.82-2.98 (1H, m), 4.34-4.39 (1H, m), 4.44-4.57 (2H, m), 6.80-6.89 (2H, m), 7.36-7.42 (2H, m), 7.46-7.54 (2H, m), 7.86-7.94 (1H, m), 7.98-8.04 (1H, m), 8.66-8.74 (1H, m).
ESI-MS (m/e): 430.2 [M+H]$^+$ Example 40

Synthesis of (1R*,2R*,5R*)-N-(4-Isopropoxyphenyl)-8-(pyridin-3-ylsulfonyl)-8-azabicyclo[3.2.1]octane-2-carboxamide The title compound was synthesized as in Example 13, using the title compound of Production Example 3 and pyridine-3-sulfonyl chloride as the raw material.
1H-NMR (400 MHz, CDCl3, δ): 1.31 (6H, d, J=5.9 Hz), 1.34-1.54 (1H, m), 1.56-1.69 (2H, m), 1.75-1.84 (1H, m), 1.88-2.06 (3H, m), 2.10-2.18 (1H, m), 2.81-2.87 (1H, m), 4.23-4.30 (1H, m), 4.40-4.56 (2H, m), 6.79-6.88 (2H, m), 7.36-7.56 (4H, m), 8.12-8.20 (1H, m), 8.79-8.85 (1H, m), 9.07-9.12 (1H, m).
ESI-MS (m/e): 430.2 [M+H]$^+$ Example 41

Synthesis of (1R*,4S*,6R*)-2-(Butyl sulfonyl)-N-(3-methoxypyridin-2-yl)-2-azabicyclo[2.2.2]octane-6-carboxamide The title compound was synthesized as in Reference Example 1(2), using the title compound of Production Example 1 and 2-amino-3-methoxypyridine as the raw material.
1H-NMR (400 MHz, CDCl3, δ): 0.97 (3H, t, J=7.3 Hz), 1.41-1.53 (2H, m), 1.58-1.68 (1H, m), 1.75-1.90 (6H, m), 1.95-2.07 (1H, m), 2.08-2.14 (1H, m), 2.33-2.42 (1H, m), 2.96-3.12 (2H, m), 3.34-3.41 (1H, m), 3.44-3.51 (1H, m), 3.89 (3H, s), 4.07-4.16 (1H, m), 6.97-7.07 (1H, m), 7.10-7.16 (1H, m), 7.92-8.09 (2H, m).
ESI-MS (m/e): 382.4 [M+H]$^+$ Example 42

Synthesis of (1R*,4S*,6R*)-2-(Butyl sulfonyl)-N-(3-cyclopropyl-1H-pyrazol-5-yl)-2-azabicyclo[2.2.2]octane-6-carboxamide The title compound was synthesized as in Reference Example 1(2), using the title compound of Production Example 1 and 5-cyclopropyl-1H-pyrazole-3-amine as the raw material.
1H-NMR (400 MHz, CDCl3, δ): 0.76-0.83 (2H, m), 0.93-1.01 (5H, m), 1.42-1.53 (2H, m), 1.57-1.66 (1H, m), 1.69-1.99 (6H, m), 2.03-2.14 (2H, m), 2.26-2.36 (1H, m), 2.90-3.11 (3H, m), 3.23-3.29 (1H, m), 3.53-3.59 (1H, m), 4.02-4.06 (1H, m), 6.37 (1H, s), 11.46 (1H, br s).
ESI-MS (m/e): 381.4 [M+H]$^+$ Example 43

Synthesis of (1R*,4S*,6R*)-N-(3-methoxypyridin-2-yl)-2-(phenylsulfonyl)-2-azabicyclo[2.2.2]octane-6-carboxamide The title compound was synthesized as in Example 13, using the title compound of Production Example 19 and benzenesulfonyl chloride as the raw material.
1H-NMR (400 MHz, CDCl3, δ): 1.19-1.43 (1H, m), 1.48-1.61 (1H, m), 1.66-1.94 (4H, m), 2.00-2.10 (1H, m), 2.16-2.27 (1H, m), 3.27-3.44 (2H, m), 3.92 (3H, s), 4.20-4.28 (1H, m), 6.99-7.07 (1H, m), 7.13-7.19 (1H, m), 7.47-7.63 (3H, m), 7.85-7.96 (3H, m), 8.01-8.05 (1H, m).
ESI-MS (m/e): 402.2 [M+H]+

Example 44

Synthesis of (1R*,4S*,6R*)-N-(5-Isopropoxypyridin-2-yl)-2-(phenylsulfonyl)-2-azabicyclo[2.2.2]octane-6-carboxamide Diisopropylethylamine (0.071 mL, 0.41 mmol) and HATU (42.7 mg, 0.11 mmol) were added to a DMF (1 mL) solution of the title compound (30 mg, 0.1 mmol) of Production Example 4 and the title compound (21.1 mg, 0.11 mmol) of Production Example 20, and the mixture was stirred at room temperature for 14 hours. The reaction mixture was diluted with ethyl acetate, and washed twice with a saturated sodium hydrogen carbonate aqueous solution. The organic layer was dried over magnesium sulfate, and concentrated under reduced pressure. The resulting residue was then purified using silica gel column chromatography to obtain the title compound (18.7 mg, 43%).
1H-NMR (400 MHz, CDCl3, δ): 1.31-1.44 (7H, m), 1.49-1.60 (1H, m), 1.62-1.80 (3H, m), 2.01-2.09 (1H, m), 2.13-2.23 (1H, m), 2.77-2.85 (1H, m), 3.29-3.35 (1H, m), 3.38-3.45 (1H, m), 4.05-4.17 (1H, m), 4.47-4.57 (1H, m), 7.20-7.25 (1H, m), 7.53-7.64 (3H, m), 7.86-7.98 (3H, m), 8.00-8.10 (2H, m).
ESI-MS (m/e): 430.2 [M+H]$^+$ Example 45

Synthesis of (1R*,4S*,6R*)-N-(3-Isopropoxyphenyl)-2-(phenylsulfonyl)-2-azabicyclo[2.2.2]octane-6-carboxamide The title compound was synthesized as in Example 44, using the title compound of Production Example 4 and 3-isopropoxyaniline as the raw material.
1H-NMR (400 MHz, CDCl3, δ): 1.33 (6H, d, J=6.1 Hz), 1.41-1.50 (1H, m), 1.63-1.96 (4H, m), 2.02-2.09 (1H, m), 2.17-2.28 (1H, m), 2.86-2.95 (1H, m), 3.22-3.29 (1H, m), 3.44-3.52 (1H, m), 4.02-4.09 (1H, m), 4.51-4.60 (1H, m), 6.60-6.68 (1H, m), 6.92-7.01 (1H, m), 7.15-7.22 (1H, m), 7.50-7.67 (4H, m), 7.83-7.93 (2H, m).
ESI-MS (m/e): 429.2 [M+H]$^+$ Example 46

Synthesis of (1R*,4S*,6R*)-N-(3-Methoxypyridin-2-yl)-2-(pyridin-2-ylsulfonyl)-2-azabicyclo[2.2.2]octane-6-carboxamide The title compound was synthesized as in Example 13, using the title compound of Production Example 19 and pyridine-2-sulfonyl chloride as the raw material.
1H-NMR (400 MHz, CDCl3, δ): 1.44-1.55 (1H, m), 1.63-1.82 (4H, m), 1.86-1.95 (1H, m), 2.01-2.08 (1H, m), 2.24-2.36 (1H, m), 3.34-3.41 (1H, m), 3.49-3.56 (1H, m), 3.90 (3H, s), 4.36-4.41 (1H, m), 6.98-7.06 (1H, m), 7.11-7.17 (1H, m), 7.47-7.54 (1H, m), 7.89-7.96 (1H, m), 7.99-8.05 (2H, m), 8.13 (1H, br s), 8.70-8.80 (1H, m).
ESI-MS (m/e): 403.2 [M+H]$^+$

Example 47

Synthesis of (1R*,4S*,6R*)-N-(5-Isopropoxypyridin-2-yl)-2-(pyridin-2-ylsulfonyl)-2-azabicyclo[2.2.2]octane-6-carboxamide The title compound was synthesized as in Example 44, using the title compound of Production Example 5 and the title compound of Production Example 20 as the raw material.
1H-NMR (400 MHz, CDCl3, δ): 1.34 (6H, d, J=6.1 Hz), 1.52-1.96 (5H, m), 2.02-2.10 (1H, m), 2.16-2.29 (1H, m), 3.05-3.15 (1H, m), 3.26-3.34 (1H, m), 3.52-3.60 (1H, m), 4.32-4.38 (1H, m), 4.47-4.57 (1H, m), 7.21-7.26 (1H, m), 7.50-7.58 (1H, m), 7.90-7.99 (2H, m), 8.01-8.11 (2H, m), 8.33 (1H, br s), 8.82-8.88 (1H, m).
ESI-MS (m/e): 431.3 [M+H]$^+$

Example 48

Synthesis of (1R*,4S*,6R*)-N-(5-isopropoxypyridin-2-yl)-2-[(1-methyl-1H-imidazol-4-yl)sulfonyl]-2-azabicyclo[2.2.2]octane-6-carboxamide The title compound was synthesized as in Reference Example 1(2), using the title compound of Production Example 6 and the title compound of Production Example 20 as the raw material.
1H-NMR (400 MHz, CDCl3, δ): 1.33 (6H, d, J=6.3 Hz), 1.51-1.65 (2H, m), 1.69-1.85 (2H, m), 1.89-2.09 (2H, m), 2.13-2.22 (1H, m), 3.02-3.14 (2H, m), 3.43-3.51 (1H, m), 3.79 (3H, s), 4.28-4.33 (1H, m), 4.45-4.55 (1H, m), 7.20-7.25 (1H, m), 7.47-7.50 (1H, m), 7.64-7.68 (1H, m), 7.92-7.98 (1H, m), 8.02-8.09 (1H, m), 9.02 (1H, br s).
ESI-MS (m/e): 434.3 [M+H]$^+$

Example 49

Synthesis of (1R*,4S*,6R*)-N-(3-Cyclopropyl-1H-pyrazol-5-yl)-2-(pyridin-2-ylsulfonyl)-2-azabicyclo[2.2.2]octane-6-carboxamide The title compound was synthesized as in Reference Example 1(2), using the title compound of Production Example 5 and 5-cyclopropyl-1H-pyrazole-3-amine as the raw material.
1H-NMR (400 MHz, CDCl3, δ): 0.72-0.79 (2H, m), 0.84-0.95 (2H, m), 1.36-1.52 (2H, m), 1.56-1.65 (1H, m), 1.74-1.90 (3H, m), 2.00-2.08 (1H, m), 2.30-2.40 (1H, m), 3.20-3.30 (1H, m), 3.44-3.54 (2H, m), 4.26-4.33 (1H, m), 6.37 (1H, s), 7.49-7.57 (1H, m), 7.90-7.96 (1H, m), 7.99-8.04 (1H, m), 8.66-8.75 (1H, m), 11.51 (1H, br s).
ESI-MS (m/e): 402.3 [M+H]$^+$

Example 50

Optical resolution of (1R*,4S*,6R*)-N-(5-Isopropoxypyridin-2-yl)-2-[(1-methyl-1H-imidazol-4-yl)sulfonyl]-2-azabicyclo[2.2.2]octane-6-carboxamide The compound (561 mg, 1.29 mmol) synthesized in Example 48 was optically resolved using normal-phase chiral HPLC (CHIRALPAK OD 2 cm ø×25 cmL (Daicel Chemical Industries, Ltd.); mobile phase: hexane:ethanol=70:30; flow rate: 10 ml/min; isogradient), and (1R,4S,6R)-N-(5-isopropoxypyridin-2-yl)-2-[(1-methyl-1H-imidazol-4-yl)sulfonyl]-2-azabicyclo[2.2.2]octane-6-carboxamide (retention time: 22 min; 109 mg), and (1S,4R,6S)-N-(5-isopropoxypyridin-2-yl)-2-[(1-methyl-1H-imidazol-4-yl)sulfonyl]-2-azabicyclo[2.2.2]octane-6-carboxamide (retention time: 48.5 min; 115 mg) were obtained.

Example 51

Synthesis of (1R*,4S*,6R*)-N-(4-Isopropoxyphenyl)-2-[(5-methyl-1,3,4-thiadiazol-2-yl)sulfonyl]-2-azabicyclo[2.2.2]octane-6-carboxamide The title compound was synthesized as in Example 13, using the title compound of Production Example 2 and 5-methyl-1,3,4-thiadiazole-2-sulfonyl chloride as the raw material.
1H-NMR (400 MHz, CDCl3, δ): 1.31 (6H, d, J=6.1 Hz), 1.55-1.76 (2H, m), 1.78-1.97 (3H, m), 2.11-2.16 (1H, m), 2.23-2.31 (1H, m), 2.88 (3H, s), 3.06-3.14 (1H, m), 3.33-3.40 (1H, m), 3.57-3.65 (1H, m), 4.26-4.34 (1H, m), 4.44-4.56 (1H, m), 6.82-6.88 (2H, m), 7.42-7.47 (2H, m), 7.77 (1H, br s).
ESI-MS (m/e): 451.2 [M+H]$^+$

Example 52

Synthesis of (1R*,4S*,6R*)-N-(2-Isopropoxyphenyl)-2-(phenylsulfonyl)-2-azabicyclo[2.2.2]octane-6-carboxamide The title compound was synthesized as in Example 44, using the title compound of Production Example 4 and 2-isopropoxyaniline as the raw material.
1H-NMR (400 MHz, CDCl3, δ): 1.44 (6H, d, J=5.9 Hz), 1.54-1.83 (4H, m), 2.02-2.08 (1H, m), 2.14-2.22 (1H, m), 2.80-2.88 (1H, m), 3.30-3.46 (2H, m), 4.07-4.15 (1H, m), 4.55-4.68 (1H, m), 6.87-6.96 (2H, m), 6.99-7.07 (1H, m), 7.50-7.63 (3H, m), 7.83 (1H, br s), 7.86-7.94 (2H, m), 8.23-8.32 (1H, m).
ESI-MS (m/e): 429.3 [M+H]$^+$

Example 53

Synthesis of (1R*,4S*,6R*)-N-(5-tert-Butyl-1,3,4-thiadiazol-2-yl)-2-(phenylsulfonyl)-2-azabicyclo[2.2.2]octane-6-carboxamide The title compound was synthesized as in Example 44, using the title compound of Production Example 4 and 5-tert-butyl-1,3,4-thiadiazole-2-amine as the raw material.
1H-NMR (400 MHz, CDCl3, δ): 1.48 (9H, s), 1.55-1.69 (2H, m), 1.83-2.00 (3H, m), 2.03-2.10 (1H, m), 2.20-2.31 (1H, m), 3.32-3.42 (2H, m), 3.46-3.53 (1H, m), 4.15-4.19 (1H, m), 7.44-7.58 (3H, m), 7.83-7.89 (2H, m).
ESI-MS (m/e): 435.3 [M+H]$^+$

Example 54

Synthesis of (1R*,4S*,6R*)-N-(3-Isopropyl-1,2,4-thiadiazol-5-yl)-2-(phenylsulfonyl)-2-azabicyclo[2.2.2]octane-6-carboxamide The title compound was synthesized as in Example 44, using the title compound of Production Example 4 and 3-isopropyl-1,2,4-thiadiazole-5-amine as the raw material.
1H-NMR (400 MHz, CDCl3, δ): 1.29-1.44 (7H, m), 1.47-1.71 (2H, m), 1.78-1.87 (1H, m), 2.06-2.13 (1H, m), 2.18-

2.28 (1H, m), 3.09-3.22 (2H, m), 3.25-3.31 (1H, m), 3.47-3.53 (1H, m), 4.12-4.18 (1H, m), 7.51-7.57 (2H, m), 7.58-7.64 (1H, m), 7.87-7.92 (2H, m).
ESI-MS (m/e): 421.3 [M+H]$^+$

Example 55

Synthesis of (1R*,4S*,6R*)-2-(Phenylsulfonyl)-N-[5-(trifluoromethyl)-1,3,4-thiadiazol-2-yl]-2-azabicyclo[2.2.2]octane-6-carboxamide The title compound was synthesized as in Example 44, using the title compound of Production Example 4 and 5-(trifluoromethyl)-1,3,4-thiadiazole-2-amine as the raw material.
1H-NMR (400 MHz, CDCl3, δ): 1.32-1.45 (1H, m), 1.51-1.77 (3H, m), 1.97-2.16 (3H, m), 3.27-3.38 (2H, m), 3.45-3.52 (1H, m), 4.18-4.28 (1H, m), 7.46-7.60 (3H, m), 7.84-7.90 (2H, m).
ESI-MS (m/e): 447.2 [M+H]$^+$ Example 56

Synthesis of (1R*,4S*,6R*)-N-(6-Isopropoxypyridin-3-yl)-2-(pyridin-2-ylsulfonyl)-2-azabicyclo[2.2.2]octane-6-carboxamide The title compound was synthesized as in Reference Example 1(2), using the title compound of Production Example 5 and 6-isopropoxypyridine-3-amine as the raw material.
1H-NMR (400 MHz, CDCl3, δ): 1.33 (6H, d, J=6.3 Hz), 1.46-1.55 (1H, m), 1.57-1.66 (1H, m), 1.69-1.85 (2H, m), 2.02-2.08 (1H, m), 2.19-2.22 (1H, m), 2.23-2.30 (1H, m), 3.05-3.18 (1H, m), 3.25-3.35 (1H, m), 3.45-3.56 (1H, m), 4.27-4.34 (1H, m), 5.19-5.30 (1H, m), 6.62-6.69 (1H, m), 7.51-7.56 (1H, m), 7.80 (1H, br s), 7.84-7.89 (1H, m), 7.92-7.98 (1H, m), 8.02-8.06 (1H, m), 8.16-8.22 (1H, m), 8.68-8.77 (1H, m).
ESI-MS (m/e): 431.3 [M+H]$^+$ Example 57

Synthesis of (1R*,4S*,6R*)-N-(6-Isopropoxypyridin-3-yl)-2-[(1-methyl-1H-imidazol-4-yl)sulfonyl]-2-azabicyclo[2.2.2]octane-6-carboxamide The title compound was synthesized as in Reference Example 1(2), using the title compound of Production Example 6 and 6-isopropoxypyridine-3-amine as the raw material.
1H-NMR (400 MHz, CDCl3, δ): 1.33 (6H, d, J=6.3 Hz), 1.45-1.52 (1H, m), 1.55-1.67 (1H, m), 1.72-1.83 (2H, m), 1.90-2.07 (2H, m), 2.14-2.22 (1H, m), 2.93-3.08 (2H, m), 3.37-3.50 (1H, m), 3.80 (3H, s), 4.27-4.33 (1H, m), 5.16-5.29 (1H, m), 6.63-6.68 (1H, m), 7.49-7.52 (1H, m), 7.58-7.61 (1H, m), 7.89-7.96 (1H, m), 8.20-8.28 (1H, m), 8.73 (1H, br s).
ESI-MS (m/e): 434.3 [M+H]$^+$ Example 58

Synthesis of N-{[1-(Ethylsulfonyl)-3-phenylpiperidin-3-yl]methyl}-2-methoxybenzamide The title compound was synthesized as in Example 13, using the title compound of Production Example 8 and ethanesulfonyl chloride as the raw material.
1H-NMR (400 MHz, CDCl3, δ): 1.35 (3H, t, J=7.3 Hz), 1.56-1.64 (1H, m), 1.77-1.87 (2H, m), 2.11-2.20 (1H, m), 2.88-2.99 (2H, m), 3.08-3.16 (1H, m), 3.25-3.30 (1H, m), 3.37-3.45 (1H, m), 3.56 (3H, s), 3.73-3.84 (2H, m), 3.92-3.99 (1H, m), 6.82-6.87 (1H, m), 6.99-7.06 (1H, m), 7.27-7.33 (1H, m), 7.36-7.46 (3H, m), 7.49-7.59 (3H, m), 8.10-8.15 (1H, m).
ESI-MS (m/e): 417.0 [M+H]$^+$ Example 59

Synthesis of 2-Methoxy-N-{[3-phenyl-1-(propylsulfonyl)piperidin-3-yl]methyl}benzamide The title compound was synthesized as in Example 13, using the title compound of Production Example 8 and 1-propanesulfonyl chloride as the raw material.
1H-NMR (400 MHz, CDCl3, δ): 1.03 (3H, t, J=7.6 Hz), 1.54-1.65 (1H, m), 1.76-1.89 (4H, m), 2.11-2.21 (1H, m), 2.77-2.93 (2H, m), 3.03-3.12 (1H, m), 3.18-3.25 (1H, m), 3.37-3.46 (1H, m), 3.56 (3H, s), 3.70-3.86 (2H, m), 3.94-4.01 (1H, m), 6.81-6.87 (1H, m), 7.00-7.05 (1H, m), 7.27-7.33 (1H, m), 7.36-7.46 (3H, m), 7.50-7.58 (3H, m), 8.10-8.15 (1H, m).
ESI-MS (m/e): 431.0 [M+H]$^+$ Example 60

Synthesis of 2-Methoxy-N-{[1-(methylsulfonyl)-3-phenylpiperidin-3-yl]methyl}benzamide The title compound was synthesized as in Example 13, using the title compound of Production Example 8 and methanesulfonyl chloride as the raw material.
1H-NMR (400 MHz, CDCl3, δ): 1.54-1.64 (1H, m), 1.73-1.86 (2H, m), 2.15-2.24 (1H, m), 2.76 (3H, s), 2.92-3.03 (1H, m), 3.08-3.15 (1H, m), 3.40-3.47 (1H, m), 3.56 (3H, s), 3.66-3.73 (1H, m), 3.82-3.89 (1H, m), 3.98-4.04 (1H, m), 6.82-6.87 (1H, m), 6.99-7.06 (1H, m), 7.28-7.33 (1H, m), 7.36-7.46 (3H, m), 7.50-7.59 (3H, m), 8.10-8.15 (1H, m).
ESI-MS (m/e): 403.2 [M+H]$^+$ Example 61

Synthesis of N-{[1-(Butyl sulfonyl)-3-phenylpiperidin-3-yl]methyl}-2-methoxybenzamide The title compound was synthesized as in Example 13, using the title compound of Production Example 8 and 1-butanesulfonyl chloride as the raw material.
1H-NMR (400 MHz, CDCl3, δ): 0.93 (3H, t, J=7.3 Hz), 1.36-1.48 (2H, m), 1.55-1.64 (1H, m), 1.72-1.85 (4H, m), 2.12-2.21 (1H, m), 2.80-2.94 (2H, m), 3.04-3.13 (1H, m), 3.19-3.25 (1H, m), 3.37-3.46 (1H, m), 3.56 (3H, s), 3.71-3.85 (2H, m), 3.95-4.02 (1H, m), 6.82-6.87 (1H, m), 6.99-7.06 (1H, m), 7.27-7.33 (3H, m), 7.36-7.46 (3H, m), 7.49-7.59 (3H, m), 8.09-8.16 (1H, m).
ESI-MS (m/e): 445.1 [M+H]$^+$ Example 62

Synthesis of 2-Methoxy-N-{[3-phenyl-1-(phenylsulfonyl)piperidin-3-yl]methyl}benzamide The title compound was synthesized as in Example 13, using the title compound of Production Example 8 and benzenesulfonyl chloride as the raw material.

1H-NMR (400 MHz, CDCl3, δ): 1.50-1.65 (2H, m), 1.69-1.81 (1H, m), 2.01-2.12 (1H, m), 2.57-2.69 (1H, m), 2.75-2.84 (1H, m), 3.25-3.37 (1H, m), 3.59 (3H, s), 3.64-3.78 (2H, m), 3.86-3.99 (1H, m), 6.83-6.89 (1H, m), 7.00-7.07 (1H, m), 7.28-7.34 (1H, m), 7.37-7.47 (3H, m), 7.48-7.63 (6H, m), 7.73-7.78 (2H, m), 8.12-8.16 (1H, m).
ESI-MS (m/e): 465.0 [M+H]$^+$

Example 63

Synthesis of 2-Methoxy-N-({1-[(2-methylphenyl)sulfonyl]-3-phenylpiperidin-3-yl}methyl)benzamide The title compound was synthesized as in Example 13, using the title compound of Production Example 8 and 2-methylbenzenesulfonyl chloride as the raw material.
1H-NMR (400 MHz, CDCl3, δ): 1.55-1.67 (2H, m), 1.72-1.87 (2H, m), 2.04-2.15 (1H, m), 2.52-2.56 (3H, m), 2.93-3.02 (1H, m), 3.09-3.15 (1H, m), 3.29-3.36 (1H, m), 3.55-3.58 (3H, m), 3.70-3.92 (2H, m), 6.82-6.89 (1H, m), 7.01-7.07 (1H, m), 7.23-7.52 (9H, m), 7.54-7.66 (1H, m), 7.85-7.91 (1H, m), 8.11-8.18 (1H, m).
ESI-MS (m/e): 479.1 [M+H]$^+$ Example 64

Synthesis of 2-Methoxy-N-{[3-phenyl-1-(pyridin-2-ylsulfonyl)piperidin-3-yl]methyl}benzamide The title compound was synthesized as in Example 13, using the title compound of Production Example 8 and pyridine-2-sulfonyl chloride as the raw material.
1H-NMR (400 MHz, CDCl3, δ): 1.53-1.66 (1H, m), 1.68-1.85 (2H, m), 2.09-2.17 (1H, m), 3.03-3.14 (1H, m), 3.18-3.25 (1H, m), 3.47-3.56 (1H, m), 3.59 (3H, s), 3.63-3.71 (1H, m), 3.77-3.87 (1H, m), 4.05-4.14 (1H, m), 6.82-6.88 (1H, m), 6.98-7.06 (1H, m), 7.28-7.33 (1H, m), 7.36-7.51 (4H, m), 7.52-7.60 (3H, m), 7.87-7.95 (2H, m), 8.09-8.14 (1H, m), 8.70-8.73 (1H, m).
ESI-MS (m/e): 466.0 [M+H]$^+$ Example 65

Synthesis of 2-Methoxy-N-({1-[(1-methyl-1H-imidazol-4-yl)sulfonyl]-3-phenylpiperidin-3-yl}methyl)benzamide The title compound was synthesized as in Example 13, using the title compound of Production Example 8 and 1-methyl-1H-imidazole-4-sulfonyl chloride as the raw material.
1H-NMR (400 MHz, CDCl3, δ): 1.50-1.60 (1H, m), 1.63-1.81 (2H, m), 2.08-2.16 (1H, m), 2.90-3.02 (2H, m), 3.46-3.55 (1H, m), 3.58 (3H, s), 3.66-3.81 (5H, m), 3.97-4.06 (1H, m), 6.83-6.88 (1H, m), 6.99-7.05 (1H, m), 7.28-7.32 (1H, m), 7.35-7.45 (4H, m), 7.46-7.51 (1H, m), 7.52-7.61 (3H, m), 8.08-8.15 (1H, m).
ESI-MS (m/e): 469.2 [M+H]$^+$ Example 66

Synthesis of N-({1-[(2-Chlorophenyl)sulfonyl]-3-phenylpiperidin-3-yl}methyl)-2-methoxybenzamide The title compound was synthesized as in Example 13, using the title compound of Production Example 8 and 2-chlorobenzenesulfonyl chloride as the raw material.
1H-NMR (400 MHz, CDCl3, δ): 1.62-1.72 (1H, m), 1.76-1.94 (2H, m), 2.02-2.12 (1H, m), 3.08-3.18 (1H, m), 3.28-3.39 (2H, m), 3.52-3.62 (4H, m), 3.80-3.96 (2H, m), 6.82-6.88 (1H, m), 6.99-7.06 (1H, m), 7.27-7.32 (1H, m), 7.34-7.42 (4H, m), 7.43-7.48 (3H, m), 7.49-7.57 (2H, m), 7.99-8.04 (1H, m), 8.10-8.16 (1H, m).
ESI-MS (m/e): 499.0 [M+H]$^+$ Example 67

Synthesis of N-({1-[(3-Chlorophenyl)sulfonyl]-3-phenylpiperidin-3-yl}methyl)-2-methoxybenzamide The title compound was synthesized as in Example 13, using the title compound of Production Example 8 and 3-chlorobenzenesulfonyl chloride as the raw material.
1H-NMR (400 MHz, CDCl3, δ): 1.54-1.69 (2H, m), 1.75-1.85 (1H, m), 2.05-2.15 (1H, m), 2.63-2.77 (1H, m), 2.80-2.90 (1H, m), 3.24-3.35 (1H, m), 3.59 (3H, s), 3.64-3.72 (1H, m), 3.73-3.82 (1H, m), 3.84-3.94 (1H, m), 6.83-6.90 (1H, m), 7.01-7.08 (1H, m), 7.28-7.35 (1H, m), 7.36-7.60 (8H, m), 7.61-7.66 (1H, m), 7.72-7.76 (1H, m), 8.12-8.19 (1H, m).
ESI-MS (m/e): 499.0 [M+H]$^+$ Example 68

Synthesis of N-({1-[(4-Chlorophenyl)sulfonyl]-3-phenylpiperidin-3-yl}methyl)-2-methoxybenzamide The title compound was synthesized as in Example 13, using the title compound of Production Example 8 and 4-chlorobenzenesulfonyl chloride as the raw material.
1H-NMR (400 MHz, CDCl3, δ): 1.49-1.67 (2H, m), 1.72-1.82 (1H, m), 2.04-2.15 (1H, m), 2.57-2.69 (1H, m), 2.75-2.86 (1H, m), 3.25-3.35 (1H, m), 3.58 (3H, s), 3.66-3.76 (2H, m), 3.86-3.95 (1H, m), 6.82-6.90 (1H, m), 7.01-7.08 (1H, m), 7.29-7.35 (1H, m), 7.37-7.58 (8H, m), 7.65-7.72 (2H, m), 8.11-8.17 (1H, m).
ESI-MS (m/e): 499.0 [M+H]$^+$ Example 69

Synthesis of 2-Methoxy-N-({1-[3-methoxyphenyl)sulfonyl]-3-phenylpiperidin-3-yl}methyl)benzamide The title compound was synthesized as in Example 13, using the title compound of Production Example 8 and 3-methoxybenzenesulfonyl chloride as the raw material.
1H-NMR (400 MHz, CDCl3, δ): 1.49-1.67 (2H, m), 1.71-1.79 (1H, m), 2.04-2.14 (1H, m), 2.57-2.67 (1H, m), 2.74-2.83 (1H, m), 3.28-3.39 (1H, m), 3.59 (3H, s), 3.67-3.75 (2H, m), 3.85 (3H, s), 3.91-3.98 (1H, m), 6.84-6.89 (1H, m), 7.00-7.06 (1H, m), 7.09-7.14 (1H, m), 7.22-7.25 (1H, m), 7.29-7.35 (2H, m), 7.37-7.47 (4H, m), 7.50-7.59 (3H, m), 8.10-8.15 (1H, m).
ESI-MS (m/e): 495.0 [M+H]$^+$ Example 70

Synthesis of 2-Methoxy-N-({1-[4-methoxyphenyl)sulfonyl]-3-phenylpiperidin-3-yl}methyl)benzamide The title compound was synthesized as in Example 13, using the title compound of Production Example 8 and 4-methoxybenzenesulfonyl chloride as the raw material.
1H-NMR (400 MHz, CDCl3, δ): 1.48-1.65 (2H, m), 1.68-1.81 (1H, m), 2.01-2.13 (1H, m), 2.54-2.65 (1H, m), 2.71-

2.81 (1H, m), 3.26-3.36 (1H, m), 3.59 (3H, s), 3.66-3.77 (2H, m), 3.87 (3H, s), 3.89-3.97 (1H, m), 6.83-6.89 (1H, m), 6.96-7.08 (3H, m), 7.28-7.34 (1H, m), 7.37-7.47 (3H, m), 7.48-7.53 (1H, m), 7.54-7.59 (2H, m), 7.66-7.72 (2H, m), 8.10-8.16 (1H, m).

ESI-MS (m/e): 495.1 [M+H]$^+$

Example 71

Synthesis of 4-Isopropoxy-N-{[3-phenyl-1-(propylsulfonyl)piperidin-3-yl]methyl}benzamide The title compound was synthesized as in Example 13, using the title compound of Production Example 9 and 1-propanesulfonyl chloride as the raw material.

1H-NMR (400 MHz, CDCl3, δ): 1.04 (3H, t, J=7.6 Hz), 1.33 (6H, d, J=6.3 Hz), 1.62-1.70 (1H, m), 1.77-1.94 (4H, m), 2.06-2.16 (1H, m), 2.81-2.94 (2H, m), 3.20-3.33 (2H, m), 3.40-3.47 (1H, m), 3.62-3.70 (1H, m), 3.73-3.84 (2H, m), 4.51-4.63 (1H, m), 5.77-5.85 (1H, m), 6.79-6.85 (2H, m), 7.25-7.32 (1H, m), 7.38-7.54 (6H, m).

ESI-MS (m/e): 459.1 [M+H]$^+$

Example 72

Synthesis of 4-Isopropoxy-N-{[3-phenyl-1-(phenylsulfonyl)piperidin-3-yl]methyl}benzamide The title compound was synthesized as in Example 13, using the title compound of Production Example 9 and benzenesulfonyl chloride as the raw material.

1H-NMR (400 MHz, CDCl3, δ): 1.34 (6H, d, J=5.9 Hz), 1.64-1.72 (1H, m), 1.78-1.88 (1H, m), 1.98-2.08 (1H, m), 2.77-2.88 (1H, m), 2.96-3.06 (1H, m), 3.12-3.22 (1H, m), 3.55-3.63 (1H, m), 3.66-3.82 (2H, m), 4.52-4.64 (1H, m), 5.66-5.74 (1H, m), 6.80-6.87 (2H, m), 7.28-7.34 (1H, m), 7.40-7.64 (10H, m), 7.75-7.80 (2H, m).

ESI-MS (m/e): 493.0 [M+H]$^+$

Example 73

Synthesis of 4-Isopropoxy-N-{[3-phenyl-1-(pyridin-2-ylsulfonyl)piperidin-3-yl]methyl}benzamide The title compound was synthesized as in Example 13, using the title compound of Production Example 9 and pyridine-2-sulfonyl chloride as the raw material.

1H-NMR (400 MHz, CDCl3, δ): 1.33 (6H, d, J=5.9 Hz), 1.58-1.71 (1H, m), 1.78-1.94 (2H, m), 2.02-2.12 (1H, m), 3.23-3.41 (2H, m), 3.44-3.51 (1H, m), 3.53-3.60 (1H, m), 3.80-3.94 (2H, m), 4.51-4.64 (1H, m), 5.73-5.89 (1H, m), 6.80-6.85 (2H, m), 7.24-7.32 (1H, m), 7.37-7.45 (2H, m), 7.47-7.56 (5H, m), 7.89-7.99 (2H, m), 8.67-8.75 (1H, m).

ESI-MS (m/e): 494.1 [M+H]$^+$

Example 74

Synthesis of 4-Isopropoxy-N-({1-[(1-methyl-1H-imidazol-4-yl)sulfonyl]-3-phenylpiperidin-3-yl}methyl)benzamide The title compound was synthesized as in Example 13, using the title compound of Production Example 9 and 1-methyl-1H-imidazole-4-sulfonyl chloride as the raw material.

1H-NMR (400 MHz, CDCl3, δ): 1.33 (6H, d, J=5.9 Hz), 1.55-1.69 (1H, m), 1.71-1.90 (2H, m), 2.02-2.10 (1H, m), 3.10-3.18 (1H, m), 3.21-3.27 (1H, m), 3.31-3.38 (1H, m), 3.55-3.63 (1H, m), 3.72-3.83 (4H, m), 4.53-4.62 (1H, m), 5.75-5.84 (1H, m), 6.79-6.86 (2H, m), 7.26-7.31 (1H, m), 7.38-7.45 (3H, m), 7.47-7.54 (5H, m).

ESI-MS (m/e): 497.0 [M+H]$^+$

Example 75

N-(2-Methoxyphenyl)-N'-{[3-phenyl-1-(phenylsulfonyl)piperidin-3-yl]methyl}urea

The title compound was synthesized as in Example 13, using the title compound of Production Example 18 and benzenesulfonyl chloride as the raw material.

1H-NMR (400 MHz, CDCl3, δ): 1.70-1.82 (1H, m), 1.98-2.06 (1H, m), 2.63-2.74 (1H, m), 2.79-2.87 (1H, m), 3.19-3.33 (1H, m), 3.40-3.48 (1H, m), 3.50-3.59 (1H, m), 3.78-3.88 (4H, m), 4.27-4.36 (1H, m), 6.52-6.60 (1H, m), 6.80-6.90 (2H, m), 6.94-7.03 (1H, m), 7.24-7.31 (1H, m), 7.36-7.43 (2H, m), 7.45-7.49 (2H, m), 7.51-7.64 (3H, m), 7.73-7.82 (3H, m).

ESI-MS (m/e): 480.0 [M+H]$^+$

Example 76

Synthesis of 5-Isopropoxy-N-{[3-phenyl-1-(propylsulfonyl)piperidin-3-yl]methyl}pyridine-2-carboxamide The title compound was synthesized as in Example 13, using the title compound of Production Example 10 and 1-propanesulfonyl chloride as the raw material.

1H-NMR (400 MHz, CDCl3, δ): 1.02 (3H, t, J=7.3 Hz), 1.36 (6H, d, J=5.9 Hz), 1.56-1.69 (1H, m), 1.76-1.90 (4H, m), 2.13-2.22 (1H, m), 2.73-2.92 (2H, m), 3.06-3.18 (1H, m), 3.24-3.40 (2H, m), 3.60-3.68 (1H, m), 3.71-3.79 (1H, m), 3.84-3.95 (1H, m), 4.55-4.70 (1H, m), 7.18-7.24 (1H, m), 7.27-7.32 (1H, m), 7.36-7.43 (2H, m), 7.44-7.50 (2H, m), 7.57-7.65 (1H, m), 8.02-8.08 (2H, m).

ESI-MS (m/e): 460.0 [M+H]$^+$

Example 77

Synthesis of 5-Isopropoxy-N-{[3-phenyl-1-(phenylsulfonyl)piperidin-3-yl]methyl}pyridine-2-carboxamide The title compound was synthesized as in Example 13, using the title compound of Production Example 10 and benzenesulfonyl chloride as the raw material.

1H-NMR (400 MHz, CDCl3, δ): 1.36 (6H, d, J=6.3 Hz), 1.53-1.70 (2H, m), 1.76-1.86 (1H, m), 2.01-2.11 (1H, m), 2.65-2.79 (1H, m), 2.88-2.97 (1H, m), 3.12-3.26 (1H, m), 3.47-3.59 (1H, m), 3.69-3.83 (2H, m), 4.56-4.67 (1H, m), 7.20-7.24 (1H, m), 7.27-7.33 (1H, m), 7.38-7.45 (2H, m), 7.46-7.63 (6H, m), 7.74-7.79 (2H, m), 8.02-8.09 (2H, m).

ESI-MS (m/e): 494.0 [M+H]$^+$

Example 78

Synthesis of 5-Isopropoxy-N-{[3-phenyl-1-(pyridin-2-ylsulfonyl)piperidin-3-yl]methyl}pyridine-2-carboxamide The title compound was synthesized as in Example 13, using the title compound of Production Example 10 and pyridine-2-sulfonyl chloride as the raw material.

1H-NMR (400 MHz, CDCl3, δ): 1.36 (6H, d, J=6.3 Hz), 1.56-1.92 (3H, m), 2.06-2.16 (1H, m), 3.06-3.22 (1H, m), 3.27-3.46 (2H, m), 3.49-3.58 (1H, m), 3.80-3.88 (1H, m), 3.92-4.02 (1H, m), 4.57-4.68 (1H, m), 7.15-7.23 (1H, m), 7.25-7.32 (1H, m), 7.37-7.43 (2H, m), 7.46-7.53 (3H, m), 7.56-7.65 (1H, m), 7.87-7.96 (2H, m), 8.01-8.08 (2H, m), 8.68-8.73 (1H, m).
ESI-MS (m/e): 495.0 [M+H]$^+$

Example 79

Synthesis of 5-Isopropoxy-N-({1-[(1-methyl-1H-imidazol-4-yl)sulfonyl]-3-phenylpiperidin-3-yl}methyl)pyridine-2-carboxamide The title compound was synthesized as in Example 13, using the title compound of Production Example 10 and 1-methyl-1H-imidazole-4-sulfonyl chloride as the raw material.
1H-NMR (400 MHz, CDCl3, δ): 1.36 (6H, d, J=6.3 Hz), 1.53-1.65 (1H, m), 1.68-1.86 (2H, m), 2.06-2.15 (1H, m), 2.97-3.07 (1H, m), 3.09-3.17 (1H, m), 3.34-3.42 (1H, m), 3.50-3.59 (1H, m), 3.76 (3H, s), 3.77-3.92 (2H, m), 4.56-4.67 (1H, m), 7.16-7.22 (1H, m), 7.25-7.31 (1H, m), 7.36-7.43 (3H, m), 7.47-7.52 (3H, m), 7.56-7.63 (1H, m), 8.00-8.06 (2H, m).
ESI-MS (m/e): 498.0 [M+H]$^+$ Example 80

Synthesis of 4-Isopropoxy-N-{[3-methyl-1-(propylsulfonyl)piperidin-3-yl]methyl}benzamide The title compound was synthesized as in Example 13, using the title compound of Production Example 11 and 1-propanesulfonyl chloride as the raw material.
1H-NMR (400 MHz, CDCl3, δ): 0.88 (3H, t, J=7.3 Hz), 1.33 (6H, d, J=6.3 Hz), 1.35-1.46 (2H, m), 1.50-1.61 (1H, m), 1.63-1.84 (4H, m), 1.86-2.07 (3H, m), 2.15-2.26 (1H, m), 2.89-3.07 (2H, m), 3.13-3.26 (2H, m), 4.46-4.56 (1H, m), 7.19-7.25 (1H, m), 7.93-7.99 (1H, m), 8.03-8.09 (1H, m), 8.36-8.44 (1H, m).
ESI-MS (m/e): 397.3 [M+H]$^+$ Example 81

Synthesis of 4-Isopropoxy-N-{[3-methyl-1-(phenylsulfonyl)piperidin-3-yl]methyl}benzamide The title compound was synthesized as in Example 13, using the title compound of Production Example 11 and benzenesulfonyl chloride as the raw material.
1H-NMR (400 MHz, CDCl3, δ): 1.20-1.31 (1H, m), 1.36 (6H, d, J=6.3 Hz), 1.54-1.61 (1H, m), 1.64-1.71 (1H, m), 1.85-1.98 (1H, m), 2.22-2.30 (1H, m), 2.57-2.67 (1H, m), 3.32-3.40 (2H, m), 3.52-3.61 (1H, m), 3.69-3.77 (1H, m), 4.57-4.68 (1H, m), 6.62-6.70 (1H, m), 6.90-6.96 (2H, m), 7.51-7.64 (3H, m), 7.75-7.86 (4H, m).
ESI-MS (m/e): 431.2 [M+H]$^+$ Example 82

Synthesis of 4-Isopropoxy-N-{[3-methyl-1-(pyridin-2-ylsulfonyl)piperidin-3-yl]methyl}benzamide The title compound was synthesized as in Example 13, using the title compound of Production Example 11 and pyridine-2-sulfonyl chloride as the raw material.

1H-NMR (400 MHz, CDCl3, δ): 0.95 (3H, s), 1.35 (6H, d, J=5.9 Hz), 1.58-1.72 (1H, m), 1.81-1.97 (1H, m), 2.56-2.64 (1H, m), 2.89-2.98 (1H, m), 3.31-3.40 (1H, m), 3.59-3.66 (1H, m), 3.71-3.81 (2H, m), 4.54-4.66 (1H, m), 6.76-6.85 (1H, m), 6.87-6.94 (2H, m), 7.46-7.53 (1H, m), 7.80-7.85 (2H, m), 7.88-7.98 (2H, m), 8.66-8.72 (1H, m).
ESI-MS (m/e): 432.2 [M+H]$^+$

Example 83

Synthesis of 4-Isopropoxy-N-({3-methyl-1-[(1-methyl-1H-imidazol-4-yl)sulfonyl]piperidin-3-yl}methyl)benzamide The title compound was synthesized as in Example 13, using the title compound of Production Example 11 and 1-methyl-1H-imidazole-4-sulfonyl chloride as the raw material.
1H-NMR (400 MHz, CDCl3, δ): 1.23-1.37 (7H, m), 1.53-1.68 (2H, m), 1.81-1.93 (1H, m), 2.46-2.56 (1H, m), 2.77-2.88 (1H, m), 3.28-3.37 (1H, m), 3.51-3.58 (1H, m), 3.60-3.79 (5H, m), 4.54-4.66 (1H, m), 6.75-6.84 (1H, m), 6.87-6.92 (2H, m), 7.41-7.50 (2H, m), 7.79-7.86 (2H, m).
ESI-MS (m/e): 435.2 [M+H]$^+$ Example 84

Synthesis of N-{[3-Ethyl-1-(propylsulfonyl)piperidin-3-yl]methyl}-4-isopropoxybenzamide The title compound was synthesized as in Example 13, using the title compound of Production Example 12 and 1-propanesulfonyl chloride as the raw material.
1H-NMR (400 MHz, CDCl3, δ): 1.34 (7H, d, J=6.3 Hz), 1.39-1.64 (3H, m), 1.76-1.88 (1H, m), 1.92-2.07 (2H, m), 2.10-2.17 (1H, m), 2.19-2.37 (2H, m), 3.52-3.66 (1H, m), 4.55-4.66 (1H, m), 5.65 (1H, s), 7.55-7.61 (1H, m), 7.94-8.02 (1H, m), 8.08-8.14 (1H, m), 8.41 (1H, br s), 8.74-8.80 (1H, m).
ESI-MS (m/e): 411.3 [M+H]$^+$ Example 85

Synthesis of N-{[3-Ethyl-1-(pyridin-2-ylsulfonyl)piperidin-3-yl]methyl}-4-isopropoxybenzamide The title compound was synthesized as in Example 13, using the title compound of Production Example 12 and pyridine-2-sulfonyl chloride as the raw material.
1H-NMR (400 MHz, CDCl3, δ): 0.95 (3H, t, J=7.3 Hz), 1.08-1.20 (1H, m), 1.27-1.47 (7H, m), 1.63-1.73 (1H, m), 1.82-1.96 (1H, m), 2.56-2.65 (1H, m), 2.85-2.97 (1H, m), 3.26-3.35 (1H, m), 3.59-3.67 (1H, m), 3.75-3.93 (2H, m), 4.54-4.68 (1H, m), 6.79-6.86 (1H, m), 6.88-6.93 (2H, m), 7.45-7.53 (1H, m), 7.80-7.88 (2H, m), 7.89-8.00 (2H, m), 8.67-8.73 (1H, m).
ESI-MS (m/e): 446.2 [M+H]$^+$ Example 86

Synthesis of N-({3-Ethyl-1-[(1-methyl-1H-imidazol-4-yl)sulfonyl]piperidin-3-yl}methyl)-4-isopropoxybenzamide The title compound was synthesized as in Example 13, using the title compound of Production Example 12 and 1-methyl-1H-imidazole-4-sulfonyl chloride as the raw material.

1H-NMR (400 MHz, CDCl3, δ): 0.94 (3H, t, J=7.3 Hz), 1.09-1.21 (1H, m), 1.30-1.37 (6H, m), 1.38-1.46 (1H, m), 1.54-1.71 (1H, m), 1.79-1.94 (1H, m), 2.45-2.54 (1H, m), 2.74-2.84 (1H, m), 3.24-3.33 (1H, m), 3.53-3.60 (1H, m), 3.67-3.77 (4H, m), 3.80-3.89 (1H, m), 4.54-4.65 (1H, m), 6.76-6.84 (1H, m), 6.87-6.92 (2H, m), 7.43-7.49 (2H, m), 7.80-7.87 (2H, m).
ESI-MS (m/e): 449.2 [M+H]$^+$

Example 87

Synthesis of 4-Isopropoxy-N-{[3-isopropyl-1-(propylsulfonyl)piperidin-3-yl]methyl}benzamide The title compound was synthesized as in Example 13, using the title compound of Production Example 13 and 1-propanesulfonyl chloride as the raw material.
1H-NMR (400 MHz, CDCl3, δ): 0.90 (3H, d, J=7.3 Hz), 1.00 (3H, d, J=6.8 Hz), 1.08 (3H, t, J=7.3 Hz), 1.26-1.44 (7H, m), 1.55-1.73 (2H, m), 1.81-1.96 (2H, m), 2.66-2.81 (2H, m), 2.89-2.98 (2H, m), 3.22-3.32 (1H, m), 3.56-3.66 (1H, m), 3.77-3.86 (1H, m), 3.97-4.08 (1H, m), 4.55-4.65 (1H, m), 6.87-6.92 (2H, m), 6.94-7.01 (1H, m), 7.78-7.85 (2H, m).
ESI-MS (m/e): 425.2 [M+H]$^+$ Example 88

Synthesis of 4-Isopropoxy-N-{[3-isopropyl-1-(pyridin-2-ylsulfonyl)piperidin-3-yl]methyl}benzamide The title compound was synthesized as in Example 13, using the title compound of Production Example 13 and pyridine-2-sulfonyl chloride as the raw material.
1H-NMR (400 MHz, CDCl3, δ): 0.86 (3H, d, J=6.8 Hz), 0.99 (3H, d, J=6.8 Hz), 1.29-1.41 (7H, m), 1.53-1.73 (5H, m), 1.86-2.00 (1H, m), 2.67-2.74 (1H, m), 2.76-2.86 (1H, m), 3.29-3.38 (1H, m), 3.73-3.80 (1H, m), 3.86-3.94 (1H, m), 4.00-4.11 (1H, m), 4.55-4.65 (1H, m), 6.88-6.93 (2H, m), 6.96-7.03 (1H, m), 7.49-7.54 (1H, m), 7.85-7.90 (2H, m), 7.91-8.00 (2H, m), 8.67-8.75 (1H, m).
ESI-MS (m/e): 460.2 [M+H]$^+$ Example 89

Synthesis of 4-Isopropoxy-N-({3-isopropyl-1-[(1-methyl-1H-imidazol-4-yl)sulfonyl]piperidin-3-yl}methyl)benzamide The title compound was synthesized as in Example 13, using the title compound of Production Example 13 and 1-methyl-1H-imidazole-4-sulfonyl chloride as the raw material.
1H-NMR (400 MHz, CDCl3, δ): 0.86 (3H, d, J=6.8 Hz), 0.98 (3H, d, J=6.8 Hz), 1.25-1.38 (7H, m), 1.49-1.58 (1H, m), 1.61-1.72 (2H, m), 1.85-1.99 (1H, m), 2.54-2.61 (1H, m), 2.63-2.72 (1H, m), 3.25-3.37 (1H, m), 3.66-3.86 (5H, m), 3.95-4.07 (1H, m), 4.54-4.65 (1H, m), 6.85-6.99 (3H, m), 7.44-7.51 (2H, m), 7.83-7.90 (2H, m).
ESI-MS (m/e): 463.3 [M+H]$^+$ Example 90

Synthesis of N-{[3-Benzyl-1-(propylsulfonyl)piperidin-3-yl]methyl}-4-isopropoxybenzamide The title compound was synthesized as in Example 13, using the title compound of Production Example 14 and 1-propanesulfonyl chloride as the raw material.
1H-NMR (400 MHz, CDCl3, δ): 1.06 (3H, t, J=7.6 Hz), 1.36 (6H, d, J=5.9 Hz), 1.41-1.54 (2H, m), 1.63-1.73 (1H, m), 1.78-1.92 (3H, m), 2.52-2.63 (1H, m), 2.72-2.97 (5H, m), 3.34-3.51 (2H, m), 3.52-3.60 (1H, m), 3.78-3.87 (1H, m), 4.55-4.67 (1H, m), 6.57-6.68 (1H, m), 6.85-6.92 (2H, m), 7.23-7.36 (5H, m), 7.65-7.71 (2H, m).
ESI-MS (m/e): 473.2 [M+H]$^+$ Example 91

Synthesis of N-{[3-benzyl-1-(pyridin-2-ylsulfonyl)piperidin-3-yl]methyl}-4-isopropoxybenzamide The title compound was synthesized as in Example 13, using the title compound of Production Example 14 and pyridine-2-sulfonyl chloride as the raw material.
1H-NMR (400 MHz, CDCl3, δ): 1.35 (7H, d, J=6.3 Hz), 1.38-1.52 (2H, m), 1.65-1.74 (1H, m), 1.79-1.92 (1H, m), 2.52-2.60 (1H, m), 2.78-2.88 (2H, m), 2.90-3.00 (1H, m), 3.33-3.41 (1H, m), 3.56-3.69 (2H, m), 3.85-3.94 (1H, m), 4.55-4.67 (1H, m), 6.58-6.70 (1H, m), 6.85-6.93 (2H, m), 7.20-7.34 (5H, m), 7.46-7.54 (1H, m), 7.69-7.76 (2H, m), 7.88-8.00 (2H, m), 8.64-8.72 (1H, m).
ESI-MS (m/e): 508.2 [M+H]$^+$ Example 92

Synthesis of N-({3-Benzyl-1-[(1-methyl-1H-imidazol-4-yl)sulfonyl]piperidin-3-yl}methyl)-4-isopropoxybenzamide The title compound was synthesized as in Example 13, using the title compound of Production Example 14 and 1-methyl-1H-imidazole-4-sulfonyl chloride as the raw material.
1H-NMR (400 MHz, CDCl3, δ): 1.31-1.38 (7H, m), 1.40-1.49 (1H, m), 1.65-1.89 (2H, m), 2.50-2.57 (1H, m), 2.71-2.79 (1H, m), 2.82-2.94 (2H, m), 3.30-3.37 (1H, m), 3.44-3.56 (2H, m), 3.75 (3H, s), 3.79-3.88 (1H, m), 4.57-4.66 (1H, m), 6.51-6.61 (1H, m), 6.84-6.91 (2H, m), 7.21-7.27 (1H, m), 7.28-7.35 (4H, m), 7.41-7.49 (2H, m), 7.67-7.73 (2H, m).
ESI-MS (m/e): 511.2 [M+H]$^+$ Example 93

Synthesis of 3-Methyl-N-({1-[(1-methyl-1H-imidazol-4-yl)sulfonyl]-3-phenylpiperidin-3-yl}methyl)-1H-pyrazole-5-carboxamide Diisopropylethylamine (0.02 mL, 0.112 mmol) and HATU (37 mg, 0.097 mmol) were added to a DMF (1 mL) solution of the title compound (25 mg, 0.075 mmol) of Production Example 15 and 3-methyl-1H-pyrazole-5-carboxylic acid (10 mg, 0.079 mmol), and the mixture was stirred at room temperature for 24 hours. The reaction mixture was diluted with ethyl acetate, and washed twice with distilled water, and once with saturated brine. The organic layer was dried over magnesium sulfate, and concentrated under reduced pressure. The resulting residue was then purified using silica gel column chromatography to obtain the title compound (12 mg, 36%).
1H-NMR (CD3OD) δ: 1.51-1.63 (1H, m), 1.69-1.88 (2H, m), 2.07-2.19 (1H, m), 2.31 (3H, s), 2.89-2.96 (1H, m), 3.01-3.08 (1H, m), 3.49-3.56 (1H, m), 3.68-3.74 (1H, m), 3.78-3.85 (4H, m), 6.42 (1H, s), 7.25-7.31 (1H, m), 7.37-7.44 (2H, m), 7.52-7.57 (2H, m), 7.72-7.75 (1H, m), 7.77-7.80 (1H, m).
ESI-MS (m/e): 443.2 [M+H]$^+$

Example 94

Synthesis of 3-Ethyl-N-({1-[(1-methyl-1H-imidazol-4-yl)sulfonyl]-3-phenylpiperidin-3-yl}methyl)-1H-pyrazole-5-carboxamide The title compound was synthesized as in Example 93, using the title compound of Production Example 15 and 3-ethyl-1H-pyrazole-5-carboxylic acid as the raw material.

1H-NMR (CD3OD) δ: 1.28 (3H, t, J=7.6 Hz), 1.50-1.63 (1H, m), 1.68-1.87 (2H, m), 2.07-2.18 (1H, m), 2.70 (2H, q, J=7.6 Hz), 2.86-2.97 (1H, m), 3.00-3.08 (1H, m), 3.48-3.57 (1H, m), 3.68-3.74 (1H, m), 3.77-3.86 (4H, m), 6.45 (1H, s), 7.25-7.31 (1H, m), 7.37-7.43 (2H, m), 7.52-7.57 (2H, m), 7.73-7.75 (1H, m), 7.77-7.79 (1H, m).

ESI-MS (m/e): 457.2 [M+H]$^+$

Example 95

Synthesis of 3-Isopropyl-N-({1-[(1-methyl-1H-imidazol-4-yl)sulfonyl]-3-phenylpiperidin-3-yl}methyl)-1H-pyrazole-5-carboxamide The title compound was synthesized as in Example 93, using the title compound of Production Example 15 and 3-isopropyl-1H-pyrazole-5-carboxylic acid as the raw material.

1H-NMR (400 MHz, CDCl3, δ): 1.26 (6H, dd, J=7.0, 2.0 Hz), 1.50-1.62 (1H, m), 1.66-1.85 (2H, m), 2.02-2.14 (1H, m), 2.93-3.05 (2H, m), 3.08-3.16 (1H, m), 3.32-3.40 (1H, m), 3.50-3.59 (1H, m), 3.62-3.70 (1H, m), 3.75 (3H, s), 3.79-3.86 (1H, m), 6.49 (1H, s), 6.62-6.71 (1H, m), 7.21-7.28 (1H, m), 7.34-7.40 (2H, m), 7.45-7.53 (3H, m).

ESI-MS (m/e): 471.2 [M+H]$^+$

Example 96

Synthesis of 3-Cyclopropyl-N-({1-[(1-methyl-1H-imidazol-4-yl)sulfonyl]-3-phenylpiperidin-3-yl}methyl)-1H-pyrazole-5-carboxamide The title compound was synthesized as in Example 93, using the title compound of Production Example 15 and 3-cyclopropyl-1H-pyrazole-5-carboxylic acid as the raw material.

1H-NMR (400 MHz, CDCl3, δ): 0.66-0.72 (2H, m), 0.92-0.99 (2H, m), 1.51-1.63 (1H, m), 1.66-1.90 (3H, m), 2.02-2.13 (1H, m), 2.95-3.04 (1H, m), 3.10-3.18 (1H, m), 3.31-3.39 (1H, m), 3.50-3.58 (1H, m), 3.62-3.70 (1H, m), 3.75 (3H, s), 3.77-3.84 (1H, m), 6.31 (1H, s), 6.61-6.70 (1H, m), 7.21-7.29 (1H, m), 7.33-7.40 (2H, m), 7.41-7.52 (4H, m).

ESI-MS (m/e): 469.2 [M+H]$^+$

Example 97

Synthesis of N-({1-[(1-Methyl-1H-imidazol-4-yl)sulfonyl]-3-phenylpiperidin-3-yl}methyl)-3-(trifluoromethyl)-1H-pyrazole-5-carboxamide The title compound was synthesized as in Example 93, using the title compound of Production Example 15 and 3-trifluoromethyl-1H-pyrazole-5-carboxylic acid as the raw material.

1H-NMR (400 MHz, CDCl3, δ): 1.59-1.73 (1H, m), 1.82-1.98 (3H, m), 3.05-3.17 (1H, m), 3.29-3.39 (1H, m), 3.46-3.54 (1H, m), 3.59-3.69 (2H, m), 3.76 (3H, s), 3.85-3.94 (1H, m), 6.59-6.66 (1H, m), 6.73-6.80 (1H, m), 7.21-7.30 (1H, m), 7.32-7.38 (2H, m), 7.39-7.44 (2H, m), 7.46-7.49 (1H, m), 7.51-7.54 (1H, m).

ESI-MS (m/e): 497.1 [M+H]$^+$

Example 98

Synthesis of 3-Isobutyl-N-({1-[(1-methyl-1H-imidazol-4-yl)sulfonyl]-3-phenylpiperidin-3-yl}methyl)-1H-pyrazole-5-carboxamide The title compound was synthesized as in Example 93, using the title compound of Production Example 15 and 3-isobutyl-1H-pyrazole-5-carboxylic acid as the raw material.

1H-NMR (400 MHz, CDCl3, δ): 0.91 (6H, d, J=6.7 Hz), 1.51-1.63 (1H, m), 1.65-1.83 (2H, m), 1.85-1.94 (1H, m), 2.05-2.13 (1H, m), 2.51 (2H, d, J=7.0 Hz), 2.93-3.03 (1H, m), 3.08-3.15 (1H, m), 3.33-3.40 (1H, m), 3.51-3.58 (1H, m), 3.60-3.69 (1H, m), 3.75 (3H, s), 3.80-3.86 (1H, m).

ESI-MS (m/e): 485.2 [M+H]$^+$

Example 99

Synthesis of N-({1-[(1-Methyl-1H-imidazol-4-yl)sulfonyl]-3-phenylpiperidin-3-yl}methyl)-3-phenyl-1H-pyrazole-5-carboxamide The title compound was synthesized as in Example 93, using the title compound of Production Example 15 and 3-phenyl-1H-pyrazole-5-carboxylic acid as the raw material.

1H-NMR (DMSO-d6) δ: 1.36-1.46 (1H, m), 1.60-1.76 (2H, m), 2.09-2.20 (1H, m), 2.67-2.83 (1H, m), 2.91-3.01 (1H, m), 3.43-3.51 (1H, m), 3.54-3.63 (1H, m), 3.75 (3H, s), 3.79-3.85 (1H, m), 7.07 (1H, s), 7.20-7.56 (10H, m), 7.77-7.82 (1H, m), 7.83-7.86 (1H, m).

ESI-MS (m/e): 505.2 [M+H]$^+$

Example 100

Synthesis of 3-(2-Furyl)-N-({1-[(1-methyl-1H-imidazol-4-yl)sulfonyl]-3-phenylpiperidin-3-yl}methyl)-1H-pyrazole-5-carboxamide The title compound was synthesized as in Example 93, using the title compound of Production Example 15 and 3-(2-furyl)-1H-pyrazole-5-carboxylic acid as the raw material.

1H-NMR (CD3OD) δ: 1.50-1.64 (1H, m), 1.69-1.87 (2H, m), 2.09-2.21 (1H, m), 2.86-2.97 (1H, m), 3.01-3.10 (1H, m), 3.48-3.58 (1H, m), 3.70-3.76 (1H, m), 3.79-3.88 (4H, m), 6.51-6.60 (1H, m), 6.72-6.80 (1H, m), 6.84-6.92 (1H, m), 7.25-7.32 (1H, m), 7.37-7.45 (2H, m), 7.53-7.59 (2H, m), 7.62 (1H, s), 7.72-7.81 (2H, m).

ESI-MS (m/e): 495.2 [M+H]$^+$

Example 101

Synthesis of 3-tert-Butyl-N-({1-[(1-methyl-1H-imidazol-4-yl)sulfonyl]-3-phenylpiperidin-3-yl}methyl)-1H-pyrazole-5-carboxamide The title compound was synthesized as in Example 93, using the title compound of Production Example 15 and 3-tert-butyl-1H-pyrazole-5-carboxylic acid as the raw material.

1H-NMR (400 MHz, CDCl3, δ): 1.30 (9H, s), 1.51-1.86 (3H, m), 2.02-2.12 (1H, m), 2.98-3.08 (1H, m), 3.10-3.18 (1H, m), 3.31-3.40 (1H, m), 3.49-3.57 (1H, m), 3.70-3.87 (5H, m), 6.48-6.52 (1H, m), 6.56-6.64 (1H, m), 7.21-7.28 (1H, m), 7.33-7.40 (2H, m), 7.42-7.45 (1H, m), 7.46-7.51 (3H, m).
ESI-MS (m/e): 485.2 [M+H]$^+$

Example 102

Synthesis of N-({1-[(1-Methyl-1H-imidazol-4-yl)sulfonyl]-3-phenylpiperidin-3-yl}methyl)-3-propyl-1H-pyrazole-5-carboxamide The title compound was synthesized as in Example 93, using the title compound of Production Example 15 and 3-propyl-1H-pyrazole-5-carboxylic acid as the raw material.
1H-NMR (400 MHz, CDCl3, δ): 0.95 (3H, t, J=7.3 Hz), 1.47-1.84 (5H, m), 2.04-2.14 (1H, m), 2.62 (2H, t, J=7.3 Hz), 2.90-3.00 (1H, m), 3.06-3.16 (1H, m), 3.31-3.42 (1H, m), 3.52-3.62 (2H, m), 3.76 (3H, s), 3.79-3.88 (1H, m), 6.49 (1H, s), 6.71-6.82 (1H, m), 7.20-7.28 (1H, m), 7.33-7.39 (2H, m), 7.41-7.53 (4H, m).
ESI-MS (m/e): 471.2 [M+H]$^+$ Example 103

Synthesis of 3-Ethyl-N-(5-isopropoxypyridin-2-yl)-1-[(1-methyl-1H-imidazol-4-yl)sulfonyl]piperidine-3-carboxamide The title compound was synthesized as in Example 44, using the title compound of Production Example 16 and the title compound of Production Example 20 as the raw material.
1H-NMR (400 MHz, CDCl3, δ): 0.89 (3H, t, J=7.6 Hz), 1.33 (6H, d, J=5.9 Hz), 1.50-1.63 (1H, m), 1.68-1.88 (4H, m), 2.14-2.23 (1H, m), 2.84-2.90 (1H, m), 2.94-3.03 (1H, m), 3.56-3.64 (1H, m), 3.77 (3H, s), 3.80-3.87 (1H, m), 4.45-4.55 (1H, m), 7.20-7.25 (1H, m), 7.48-7.52 (2H, m), 7.98-8.01 (1H, m), 8.11-8.15 (1H, m), 8.51 (1H, br s).
ESI-MS (m/e): 436.2 [M+H]$^+$ Example 104

Synthesis of 3-Ethyl-N-(5-isopropoxy-1H-pyrazol-3-yl)-1-[(1-methyl-1H-imidazol-4-yl)sulfonyl]piperidine-3-carboxamide (1) Synthesis of 3-Ethyl-N-(5-isopropoxy-1-{[2-(trimethylsilyl)ethoxy]methyl}-1H-pyrazol-3-yl)-1-[(1-methyl-1H-imidazol-4-yl)sulfonyl]piperidine-3-carboxamide The title compound was synthesized as in Example 44, using the title compound of Production Example 16 and the title compound of Production Example 21 as the raw material.

(2) Synthesis of Title Compound

The compound (83 mg, 0.15 mmol) synthesized in (1), TFA (0.9 mL), and distilled water (0.1 mL) were stirred at room temperature for 2 hours. The reaction mixture was diluted with a saturated sodium hydrogen carbonate aqueous solution, and extracted with ethyl acetate. The organic layer was collected, and washed once with saturated brine. The organic layer was then dried over magnesium sulfate, and concentrated under reduced pressure. The resulting residue was then purified using silica gel column chromatography to obtain the title compound (32 mg, 50%).
1H-NMR (400 MHz, CDCl3, δ): 0.86 (3H, t, J=7.6 Hz), 1.18-1.44 (8H, m), 1.56-1.77 (2H, m), 1.81-1.92 (1H, m), 2.22-2.33 (1H, m), 2.61-2.77 (2H, m), 3.70-3.83 (4H, m), 3.99-4.08 (1H, m), 4.65-4.75 (1H, m), 5.51 (1H, s), 7.47-7.56 (2H, m), 9.14 (1H, br s).
ESI-MS (m/e): 425.2 [M+H]$^+$ Example 105

Synthesis of (1R*,4S*,6R*)-N-(5-Isopropoxy-1H-pyrazol-3-yl)-2-[(1-methyl-1H-imidazol-4-yl)sulfonyl]-2-azabicyclo[2.2.2]octane-6-carboxamide The title compound was synthesized as in Example 104, using the title compound of Production Example 6 and the title compound of Production Example 21 as the raw material.
1H-NMR (400 MHz, CDCl3, δ): 1.34 (6H, d, J=6.3 Hz), 1.41-1.52 (1H, m), 1.54-1.64 (1H, m), 1.70-1.89 (3H, m), 1.99-2.07 (1H, m), 2.18-2.27 (1H, m), 3.06-3.17 (2H, m), 3.41-3.49 (1H, m), 3.78 (3H, s), 4.22-4.27 (1H, m), 4.55-4.66 (1H, m), 5.69 (1H, br s), 7.44-7.50 (1H, m), 7.56-7.60 (1H, m), 10.45 (1H, br s).
ESI-MS (m/e): 423.2 [M+H]$^+$ Example 106

Synthesis of 3-Isopropyl-N-{1-[(1-methyl-1H-imidazol-4-yl)sulfonyl]-3-phenylpiperidin-3-yl}-1H-pyrazole-5-carboxamide The title compound was synthesized as in Example 93, using the title compound of Production Example 17 and 3-isopropyl-1H-pyrazole-5-carboxylic acid as the raw material.
1H-NMR (400 MHz, CDCl3, δ): 1.27 (6H, d, J=7.3 Hz), 1.71-1.82 (1H, m), 1.87-2.02 (2H, m), 2.67-2.81 (2H, m), 2.93-3.07 (2H, m), 3.73 (3H, s), 3.84-3.96 (2H, m), 7.20-7.27 (2H, m), 7.29-7.35 (2H, m), 7.41-7.44 (1H, m), 7.46-7.53 (3H, m), 7.68-7.74 (1H, m).
ESI-MS (m/e): 457.2 [M+H]$^+$ Example 107

Synthesis of 3-Cyclopropyl-N-{1-[(1-methyl-1H-imidazol-4-yl)sulfonyl]-3-phenylpiperidin-3-yl}-1H-pyrazole-5-carboxamide The title compound was synthesized as in Example 93, using the title compound of Production Example 17 and 3-cyclopropyl-1H-pyrazole-5-carboxylic acid as the raw material.
1H-NMR (400 MHz, CDCl3, δ): 0.69-0.75 (2H, m), 0.92-0.99 (2H, m), 1.69-1.79 (1H, m), 1.83-2.02 (3H, m), 2.67-2.82 (2H, m), 2.96-3.06 (1H, m), 3.73 (3H, s), 3.84-3.96 (2H, m), 6.37 (1H, s), 7.20-7.26 (1H, m), 7.29-7.35 (2H, m), 7.42-7.51 (4H, m), 7.67 (1H, br s).
ESI-MS (m/e): 455.2 [M+H]$^+$ Example 108

Synthesis of 4-Isopropoxy-N-{1-[(1-methyl-1H-imidazol-4-yl)sulfonyl]-3-phenylpiperidin-3-yl}benzamide The title compound was synthesized as in Example 93, using the title compound of Production Example 17 and 4-isopropoxybenzoic acid as the raw material.

1H-NMR (400 MHz, CDCl3, δ): 1.36 (6H, d, J=5.4 Hz), 1.73-2.06 (3H, m), 2.66-2.74 (1H, m), 2.76-2.84 (2H, m), 3.07-3.16 (1H, m), 3.71 (3H, s), 3.85-4.00 (2H, m), 4.55-4.69 (1H, m), 6.89-6.95 (2H, m), 7.20-7.28 (1H, m), 7.30-7.50 (7H, m), 7.83-7.90 (2H, m).

ESI-MS (m/e): 483.2 [M+H]$^+$

Production Example 1

Synthesis of (1R*,4S*,6R*)-2-(Butyl sulfonyl)-2-azabicyclo[2.2.2]octane-6-carboxylic Acid (1) Synthesis of Methyl(1R*,4S*,6R*)-2-(butyl sulfonyl)-2-azabicyclo[2.2.2]octane-6-carboxylate Triethylamine (0.51 mL, 3.7 mmol) and 1-butanesulfonyl chloride (0.233 mL, 1.84 mmol) were added to a chloroform (5 mL) solution of methyl 2-azabicyclo[2.2.2]octane-6-carboxylate hydroiodide (298 mg, 0.989 mmol) synthesized according to the method described in literature (Chem. Pharm. Bull. 53 (1) 81-85 (2005)), and the mixture was stirred at room temperature for 13 hours. The reaction mixture was washed once with distilled water, and once with a saturated sodium hydrogen carbonate aqueous solution. The organic layer was dried over magnesium sulfate, and concentrated under reduced pressure. The resulting residue was then purified using silica gel column chromatography to obtain the target (157 mg, 55%).

(2) Synthesis of Title Compound

A 5N-sodium hydroxide aqueous solution (1.5 mL) was added to a methanol (5 mL) solution of the compound (145 mg, 0.5 mmol) obtained in (1), and the mixture was stirred at room temperature for 17 hours. The reaction mixture was ice-cooled, neutralized with 5N-hydrochloric acid aqueous solution, and extracted with chloroform. The organic layer was collected, dried over magnesium sulfate, and concentrated under reduced pressure to obtain the title compound (134 mg, 97%).

Production Example 2

Synthesis of (1R*,4S*,6R*)-N-(4-Isopropoxyphenyl)-2-azabicyclo[2.2.2]octane-6-carboxamide Hydrochloride (1) Synthesis of 2-tert-Butyl 6-methyl(1R*,4S*,6R*)-2-azabicyclo[2.2.2]octane-2,6-dicarboxylate Triethylamine (4.4 mL, 31.8 mmol), di-tert-butyl dicarbonate (3.47 g, 15.9 mmol), and N,N-dimethyl-4-aminopyridine (97 mg, 0.79 mmol) were added to a chloroform (30 mL) solution of methyl 2-azabicyclo[2.2.2]octane-6-carboxylate hydroiodide (2.36 g, 7.94 mmol) synthesized according to the method described in literature (Chem. Pharm. Bull. 53 (1) 81-85 (2005)), and the mixture was stirred at room temperature for 24 hours. After washing the reaction mixture twice with a saturated sodium hydrogen carbonate aqueous solution, the organic layer was dried over magnesium sulfate, and concentrated under reduced pressure. The resulting residue was then purified using silica gel column chromatography to obtain the target (2.05 g, 96%).

(2) Synthesis of (1R*,4S*,6R*)-2-(tert-Butoxycarbonyl)-2-azabicyclo[2.2.2]octane-6-carboxylic Acid The target was obtained as in Production Example 1(2), using the compound obtained in (1).

(3) Synthesis of tert-Butyl (1R*,4S*,6R*)-6-{[(4-isopropoxyphenyl)amino]carbonyl}-2-azabicyclo[2.2.2]octane-2-carboxylate 4-Isopropoxyaniline (1.49 g, 9.87 mmol), and 1-ethyl-3-(3-dimethylaminopropyl)carbodiimide hydrochloride (hereinafter, "WSC"; 1.89 g, 9.87 mmol) were added to a pyridine (20 mL) solution of the compound (1.68 g, 6.58 mmol) synthesized in (2), and the mixture was stirred at room temperature for 14 hours. The reaction mixture was concentrated under reduced pressure, and, after addition of ethyl acetate, washed once with distilled water, once with 1 N-hydrochloric acid aqueous solution, and once with 1N-sodium hydroxide aqueous solution. The organic layer was dried over magnesium sulfate, and concentrated under reduced pressure. The resulting residue was then purified using silica gel column chromatography to obtain the target (1.26 g, 49%).

(4) Synthesis of Title Compound

A 4 N-hydrochloric acid-ethyl acetate solution (8.1 mL) was added to a chloroform (10 mL) solution of the compound (1.26 g, 3.24 mmol) synthesized in (3), and the mixture was stirred at room temperature for 13 hours. The reaction mixture was then concentrated under reduced pressure to obtain the title compound (1.15 g, 100%).

Production Example 3

Synthesis of (1R*,2R*,5R*)-N-(4-Isopropoxyphenyl)-8-azabicyclo[3.2.1]octane-2-carboxamide Hydrochloride (1) Synthesis of (1R*,2R*,5R*)-8-(tert-Butoxycarbonyl)-8-azabicyclo[3.2.1]octane-2-carboxylic Acid The target was obtained as in Production Example 1(2), using 8-tert-butyl 2-methyl(1R*,2R*,5R*)-8-azabicyclo[3.2.1]octane-2,8-dicarboxylate synthesized according to the method described in literature (Tetrahedron Letteres, Vol. 38, No. 18, 3247-3248, 1997).

(2) Synthesis of tert-Butyl (1R*,2R*,5R*)-2-{[(4-isopropoxyphenyl)amino]carbonyl}-8-azabicyclo[3.2.1]octane-8-carboxylate The title compound was synthesized as in Production Example 2(3), using the compound synthesized in (1) and 4-isopropoxyaniline.

(3) Synthesis of Title Compound

The title compound was obtained as in Production Example 2(4), using the compound synthesized in (2).

Production Example 4

Synthesis of (1R*,4S*,6R*)-2-(Phenylsulfonyl)-2-azabicyclo[2.2.2]octane-6-carboxylic Acid The title compound was synthesized as in Production Example 1, using methyl 2-azabicyclo[2.2.2]octane-6-carboxylate hydroiodide and benzenesulfonyl chloride as the raw material.

Production Example 5

Synthesis of (1R*,4S*,6R*)-2-(pyridin-2-ylsulfonyl)-2-azabicyclo[2.2.2]octane-6-carboxylic Acid The title compound was synthesized as in Production Example 1, using methyl 2-azabicyclo[2.2.2]octane-6-carboxylate hydroiodide and pyridine-2-sulfonyl chloride as the raw material.

Production Example 6

Synthesis of (1R*,4S*,6R*)-2-[(1-Methyl-1H-imidazol-4-yl)sulfonyl]-2-azabicyclo[2.2.2]octane-6-carboxylic Acid The title compound was synthesized as in Production Example 1, using methyl 2-azabicyclo[2.2.2]octane-6-carboxylate hydroiodide and 1-methyl-1H-imidazole-4-sulfonyl chloride as the raw material.

Production Example 7

Synthesis of 2-Methoxy-N-(piperidin-3-ylmethyl)benzamide Hydrochloride (1) Synthesis of tert-Butyl 3-[(1,3-dioxo-1,3-dihydro-2H-isoindol-2-yl)methyl]piperidine-1-carboxylate Diisopropyl azodicarboxylate (1.17 mL, 6.04 mmol) was added to a THF (15 mL) solution of tert-butyl 3-(hydroxymethyl)piperidine-1-carboxylate (1 g, 4.64 mmol), phthalimide (888 mg, 6.04 mmol), and triphenylphosphine (1.58 g, 6.04 mmol), and the mixture was stirred at room temperature for 24 hours. The reaction mixture was concentrated under reduced pressure, and the resulting residue was purified using silica gel column chromatography to obtain the target (1.45 g, 90%).

(2) Synthesis of tert-Butyl 3-(aminomethyl)piperidine-1-carboxylate

Hydrazine monohydrate (1 mL, 20.58 mmol) was added to an ethanol (20 mL) solution of the compound (1.45 g, 4.21 mmol) synthesized in (1), and the mixture was stirred at room temperature for 24 hours. The reaction solution was filtered, and the filtrate was concentrated under reduced pressure. The residue was re-suspended in ethanol, and allowed to stand under ice-cooled conditions. After filtration, the filtrate was concentrated under reduced pressure to obtain the target (823 mg, 91%).

(3) Synthesis of tert-Butyl 3-{[(2-methoxybenzoyl)amino]methyl}piperidine-1-carboxylate HATU (293 mg, 0.77 mmol) was added to a DMF (3 mL) solution of the compound (150 mg, 0.7 mmol) synthesized in (2), 2-methoxybenzoic acid (117 mg, 0.77 mmol), and diisopropylethylamine (0.27 mL, 1.54 mmol), and the mixture was stirred at room temperature for 24 hours. After adding ethyl acetate, the reaction mixture was washed twice with distilled water, and once with saturated brine. The organic layer was dried over magnesium sulfate, and concentrated under reduced pressure. The resulting residue was then purified using silica gel column chromatography to obtain the target (244 mg, 100%).

(4) Synthesis of Title Compound

The title compound was obtained as in Production Example 2(4), using the compound obtained in (3).

Production Example 8

Synthesis of 2-Methoxy-N-[(3-phenylpiperidin-3-yl)methyl]benzamide Hydrochloride (1) Synthesis of tert-Butyl 3-(aminomethyl)-3-phenylpiperidine-1-carboxylate The target was synthesized as in Production Example 7(1)(2), using the raw material tert-butyl 3-(hydroxymethyl)-3-phenylpiperidine-1-carboxylate synthesized according the method described in literature (WO9410165).

(2) Synthesis of Title Compound

The title compound was synthesized as in Production Example 7(3)(4), using the synthesized compound of (1) as the raw material.

Production Example 9

Synthesis of 4-Isopropoxy-N-[(3-phenylpiperidin-3-yl)methyl]benzamide Hydrochloride The title compound was synthesized as in Production Example 7, using the raw material tert-butyl 3-(hydroxymethyl)-3-phenylpiperidine-1-carboxylate and 4-isopropoxybenzoic acid synthesized according to the method described in literature (WO9410165).

Production Example 10

Synthesis of 5-Isopropoxy-N-[(3-phenylpiperidin-3-yl)methyl]pyridine-2-carboxamide Hydrochloride The title compound was synthesized as in Production Example 7, using the raw material tert-butyl 3-(hydroxymethyl)-3-phenylpiperidine-1-carboxylate and 5-isopropoxypyridine-2-carboxylic acid synthesized according to the methods described in literatures WO9410165 and JP2000344666A, respectively.

Production Example 11

Synthesis of 4-Isopropoxy-N-[(3-methylpiperidin-3-yl)methyl]benzamide Hydrochloride (1) Synthesis of 1-tert-Butyl 3-ethyl 3-methylpiperidine-1,3-dicarboxylate A THF (5 mL) solution of 1-tert-butyl 3-ethylpiperidine-1,3-dicarboxylate (1 g, 3.89 mmol) was added dropwise to a THF (15 mL) solution of lithium diisopropylamide (5.83 mmol) in a nitrogen atmosphere at −78 degrees over 5 minutes. The mixture was raised to room temperature, and stirred for 50 minutes. The temperature of the reaction mixture was lowered to −78 degrees again, and methyl iodide (1.21 mL, 19.43 mmol) was added dropwise at −78 degrees over 5 minutes. The reaction mixture was then raised to room temperature, and stirred for 5 hours. After being added to a saturated ammonium chloride aqueous solution, the reaction mixture was stirred for a while, and extracted with diethyl ether. The organic layer was collected, washed once with saturated brine, dried over magnesium sulfate, and concentrated under reduced pressure. The resulting residue was then purified using silica gel column chromatography to obtain the target (698 mg, 66%).

(2) Synthesis of tert-Butyl 3-(hydroxymethyl)-3-methylpiperidine-1-carboxylate

THF (5 mL) was added dropwise to lithium aluminum hydride (97 mg, 2.55 mmol) in a nitrogen atmosphere at 0 degrees, and the mixture was stirred for a while. Then, a THF (5 mL) solution of the compound (693 mg, 2.55 mmol) obtained in (1) was added dropwise at 0 degrees. The reaction mixture was raised to room temperature, and further stirred for 2 hours. After adding sodium sulfate decahydrate, the reaction mixture was stirred for 24 hours. After filtration, the filtrate was concentrated under reduced pressure to obtain the target (418 mg, 71%).

(3) Synthesis of Title Compound

The title compound was synthesized as in Production Example 7, using the compound synthesized in (2) and 4-isopropoxybenzoic acid.

Production Example 12

Synthesis of N-[(3-Ethylpiperidin-3-yl)methyl]-4-isopropoxybenzamide Hydrochloride (1) Synthesis of 1-tert-Butyl 3-ethyl 3-ethylpiperidine-1,3-dicarboxylate The target was synthesized as in Production Example 11(1), using 1-tert-butyl 3-ethylpiperidine-1,3-dicarboxylate and ethyl iodide as the raw material.

(2) Synthesis of Title Compound

The title compound was synthesis as in Production Example 11(2)(3), using the compound synthesized in (1).

Production Example 13

Synthesis of 4-Isopropoxy-N-[(3-isopropylpiperidin-3-yl)methyl]benzamide Hydrochloride The title compound was synthesized as in Production Example 11, using 1-tert-butyl 3-ethylpiperidine-1,3-dicarboxylate and 2-bromopropane as the raw material.

Production Example 14

Synthesis of N-[(3-Benzylpiperidin-3-yl)methyl]-4-isopropoxybenzamide Hydrochloride The title compound was synthesized as in Production Example 11, using 1-tert-butyl 3-ethylpiperidine-1,3-dicarboxylate and benzyl bromide as the raw material.

Production Example 15

Synthesis of 1-{1-[(1-methyl-1H-imidazol-4-yl)sulfonyl]-3-phenylpiperidin-3-yl}methaneamine (1) Synthesis of Methyl 1-[(1-methyl-1H-imidazol-4-yl)sulfonyl]-3-phenylpiperidine-3-carboxylate The target was synthesized as in Production Example 1(1), using the raw material methyl 3-phenylpiperidine-3-carboxylate described in literature (Tetrahedron Letters 42 (2001) 1645-1646) and 1-methyl-1H-imidazole-4-sulfonyl chloride.

(2) Synthesis of {1-[(1-Methyl-1H-imidazol-4-yl)sulfonyl]-3-phenylpiperidin-3-yl}methanol The target was synthesized as in Production Example 11(2), using the compound obtained in (1) as the raw material.

(3) Synthesis of Title Compound

The title compound was obtained as in Production Example 7(1)(2), using the compound synthesized in (2) as the raw material.

Production Example 16

Synthesis of 3-Ethyl-1-[(1-methyl-1H-imidazol-4-yl)sulfonyl]piperidine-3-carboxylic Acid (1) Synthesis of Ethyl 3-ethylpiperidine-3-carboxylate Hydrochloride The target was obtained as in Production Example 2(4), using the compound synthesized in Production Example 12(1) as the raw material.

(2) Synthesis of Title Compound

The title compound was synthesized as in Production Example 1, using the compound synthesized in (1) and 1-methyl-1H-imidazole-4-sulfonyl chloride as the raw material.

Production Example 17

Synthesis of 1-[(1-Methyl-1H-imidazol-4-yl)sulfonyl]-3-phenylpiperidine-3-amine Hydrochloride (1) Synthesis of 1-[(1-Methyl-1H-imidazol-4-yl)sulfonyl]-3-phenylpiperidine-3-carboxylic Acid The target was obtained as in Production Example 1(2), using the compound synthesized in Production Example 15(1) as the raw material.

(2) Synthesis of 3-Isocyanate-1-[(1-methyl-1H-imidazol-4-yl)sulfonyl]-3-phenylpiperidine Triethylamine (0.3 mL, 2.15 mmol) and DPPA (0.463 mL, 2.15 mmol) were added to a tert-butanol (5 mL) solution of the compound (500 mg, 1.43 mmol) synthesized in (1), and the mixture was heated to reflux for 2 hours. The solution was brought back to room temperature, and concentrated under reduced pressure. The resulting residue was dissolved in ethyl acetate, and washed once with 1N-sodium hydroxide aqueous solution. The organic layer was dried over magnesium sulfate, and concentrated under reduced pressure. The resulting residue was filtered after washing with diethyl ether, and dried under reduced pressure to obtain the target (393 mg, 79%).

(3) Synthesis of Title Compound

The compound (383 mg, 11 mmol) synthesized in (2) was dissolved in a 4 N-hydrochloric acid-1,4-dioxane solution (2.76 mL, 11.1 mmol), and the mixture was stirred at 80 degrees for 24 hours. The solution was brought back to room temperature, and concentrated under reduced pressure to obtain the title compound (401 mg, 100%).

Production Example 18

Synthesis of N-(2-Methoxyphenyl)-N'-[(3-phenylpiperidin-3-yl)methyl]urea Hydrochloride

(1) Synthesis of tert-Butyl 3-[({[(2-methoxyphenyl)amino]carbonyl}amino)methyl]-3-phenylpiperidine-1-carboxylate Triethylamine (0.036 mL, 0.258 mmol) and 2-methoxyphenyl isocyanate (28.2 mg, 0.189 mmol) were added to a chloroform (1 mL) solution of the compound (50 mg, 0.172 mmol) synthesized in Production Example 8(1), and the mixture was stirred at room temperature for 24 hours. The reaction mixture was washed once with distilled water, and once with a saturated sodium hydrogen carbonate aqueous solution. The organic layer was dried over magnesium sulfate, and concentrated under reduced pressure. The resulting residue was then purified using silica gel column chromatography to obtain the target (76 mg, 100%).

(2) Synthesis of Title Compound

The title compound was obtained as in Production Example 2(4), using the compound synthesized in (1) as the raw material.

Production Example 19

Synthesis of (1R*,4S*,6R*)-N-(3-Methoxypyridin-2-yl)-2-azabicyclo[2.2.2]octane-6-carboxamide Hydrochloride The title compound was synthesized as in Production Example 2, using methyl 2-azabicyclo[2.2.2]octane-6-carboxylate hydroiodide and 2-amino-3-methoxypyridine as the raw material.

Production Example 20

Synthesis of 5-Isopropoxypyridine-2-amine Hydrochloride

(1) Synthesis of 2-Bromo-5-isopropoxypyridine

2-Bromopropane (1.13 mL, 12 mmol) and potassium carbonate (1.43 g, 10.4 mmol) were successively added to a DMF (10 mL) solution of 6-bromopyridin-3-ol (1 g, 5.75 mmol), and the mixture was stirred at 80 degrees for 2 hours. The solution was brought back to room temperature, diluted with ethyl acetate, and washed twice with distilled water, and once with saturated brine. The organic layer was dried over magnesium sulfate, and concentrated under reduced pressure to obtain the target (1.28 g, 100%).

(2) Synthesis of Ethyl 5-isopropoxypyridine-2-carboxylic Acid

Palladium acetate (31.2 mg, 0.14 mmol) and 1,1'-bis(diphenylphosphino)ferrocene (77.1 mg, 0.14 mmol) were added to a mixture of ethanol (6 mL) and DMF (3 mL) containing the compound (600 mg, 2.78 mmol) obtained in (1), and stirred at 50 degrees for 22 hours in the presence of carbon monoxide. The reaction mixture was then diluted with ethyl acetate, and washed twice with a saturated sodium hydrogen carbonate aqueous solution, and once with saturated brine. The resulting organic layer was dried over magnesium sulfate, and concentrated under reduced pressure. The resulting residue was then purified using silica gel column chromatography to obtain the target (386 mg, 66%).

(3) Synthesis of 5-Isopropoxypyridine-2-carboxylic Acid

A 5N-sodium hydroxide aqueous solution (1.8 mL) was added to an ethanol (3 mL) solution of the compound (386 mg, 1.84 mmol) obtained in (2), and the mixture was stirred at 50 degrees for 3 hours. The reaction mixture was ice-cooled, neutralized with 5N-hydrochloric acid aqueous solution, and extracted with chloroform. The organic layer was collected, dried over magnesium sulfate, and concentrated under reduced pressure to obtain the target (258 mg, 78%).

(4) Synthesis of tert-Butyl (5-isopropoxypyridin-2-yl)carbamate

Triethylamine (0.585 mL, 4.2 mmol) and diphenylphosphoryl azide (0.453 mL, 2.1 mmol) were successively added to a tert-butanol (5 mL) solution of the compound (255 mg, 1.4 mmol) obtained in (3), and the mixture was stirred at 100 degrees for 5 hours. The reaction mixture was brought back to room temperature, and concentrated under reduced pressure. The residue was dissolved in ethyl acetate, and washed twice with 1N-sodium hydroxide aqueous solution, and once with saturated brine. The organic layer was dried over magnesium sulfate, and concentrated under reduced pressure. The resulting residue was then purified using silica gel column chromatography to obtain the target (137 mg, 39%).

(5) Synthesis of Title Compound

A 4N-hydrochloric acid-ethyl acetate solution (4.5 mL) was added to a chloroform (5 mL) solution of the compound (137 mg, 0.54 mmol) obtained in (4), and the mixture was stirred at room temperature for 18 hours. The reaction mixture was then concentrated under reduced pressure to obtain the title compound (102 mg, 100%).

Production Example 21

Synthesis of 5-Isopropoxy-1-{[2-(trimethylsilyl)ethoxy]methyl}-1H-pyrazole-3-amine Sodium hydride (60%, 425 mg, 10.63 mmol) was added to a DMF (mL) solution of 5-isopropoxy-1H-pyrazole-3-amine (1.5 g, 10.63 mmol) at −18 degrees, and the mixture was stirred for 30 minutes. Then, 2-(trimethylsilyl)ethoxymethyl chloride (1.89 mL, 10.63 mmol) was added dropwise, and stirred at room temperature for 24 hours. The reaction mixture was then diluted with ethyl acetate, and washed once with distilled water, and once with saturated brine. The organic layer was dried over magnesium sulfate, and concentrated under reduced pressure. The resulting residue was then purified using silica gel column chromatography to obtain the title compound (462 mg, 16%).

INDUSTRIAL APPLICABILITY

A compound according to the present invention has an excellent LCE inhibiting effect, and is therefore useful as a remedy for a variety of diseases involving LCE, for example, such as cardiovascular disease, neurologic disease, metabolic disease, reproductive disease, and digestive disease. A compound according to the present invention is also useful as a herbicide.

The invention claimed is:

1. A compound represented by the following Formula (I) or a pharmaceutically acceptable salt thereof;

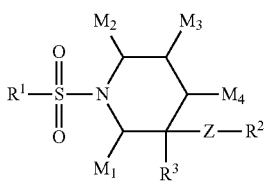

(I)

wherein,
Z is the following Formula (II-1)

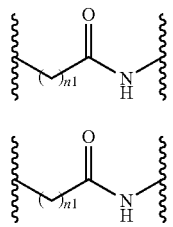

(II-1)

(II-1)

where n1 is 0
wherein,
$R^1$ represents $C_{1-6}$ alkyl, $C_{3-8}$ cycloalkyl, aryl, or heteroaryl, wherein the alkyl, cycloalkyl, aryl, or heteroaryl are unsubstituted or substituted with a substituent selected from the group consisting of: hydroxy, cyano, carboxyl, sulfo, halogen, $C_{1-6}$ alkyl, halo $C_{1-6}$ alkyl, $C_{3-8}$ cycloalkyl, $C_{1-6}$ alkoxy, halo $C_{1-6}$ alkoxy, amino, wherein the amino is unsubstituted or substituted with 1 to 2 $C_{1-6}$ alkyls, aryls, or heteroaryls, carbamoyl, wherein the carbamoyl is unsubstituted or substituted with 1 to 2 $C_{1-6}$ alkyls, aryls, or heteroaryls, sulfanyl, wherein the sulfanyl is unsubstituted or substituted with one $C_{1-6}$ alkyl, aryl, or heteroaryl, $C_{1-6}$ alkylsulfinyl, arylsulfinyl, heteroarylsulfinyl, $C_{1-6}$ alkylsulfonyl, arylsulfonyl, heteroarylsulfonyl, sulfamoyl, wherein the sulfamoyl is unsubstituted or substituted with 1 to 2 $C_{1-6}$ alkyls, aryls, or heteroaryls, $C_{1-6}$ alkylsulfonylamino, arylsulfonylamino, heteroarylsulfonylamino, $C_{1-6}$ alkylcarbonyl, arylcarbonyl, heteroarylcarbonyl, $C_{1-6}$ alkoxycarbonyl, aryloxycarbonyl, heteroaryloxycarbonyl, carbamoylamino, wherein the carbamoylamino is unsubstituted or substituted with 1 to 2 $C_{1-6}$ alkyls, aryls, or heteroaryls, $C_{1-6}$ alkoxycarbonylamino, aryloxycarbonylamino, heteroaryloxycarbonylamino, $C_{1-6}$ alkylcarbonylamino, arylcarbonylamino, heteroarylcarbonylamino, aryl, heteroaryl, aralkyl, heteroaralkyl, aralkyloxy, and heteroaralkyloxy;

$R^2$ represents phenyl or heteroaryl, wherein the phenyl or heteroaryl may be substituted with a substituent selected from the group consisting of: hydroxy, cyano, carboxyl, sulfo, halogen, $C_{1-6}$ alkyl, halo $C_{1-6}$ alkyl, $C_{3-8}$ cycloalkyl, $C_{1-6}$ alkoxy, halo $C_{1-6}$ alkoxy, amino, wherein the amino is unsubstituted or substituted with 1 to 2 $C_{1-6}$ alkyls, aryls, or heteroaryls, carbamoyl, wherein the carbamoyl is unsubstituted or substituted with 1 to 2 $C_{1-6}$ alkyls, aryls, or heteroaryls, sulfanyl, wherein the sulfanyl is unsubstituted or substituted with one $C_{1-6}$ alkyl, aryl, or heteroaryl, $C_{1-6}$ alkylsulfinyl, arylsulfinyl, heteroarylsulfinyl, $C_{1-6}$ alkylsulfonyl, arylsulfonyl, heteroarylsulfonyl, sulfamoyl, wherein the sulfamoyl is unsubstituted or substituted with 1 to 2 $C_{1-6}$ alkyls, aryls, or heteroaryls, $C_{1-6}$ alkylsulfonylamino, arylsulfonylamino, heteroarylsulfonylamino, $C_{1-6}$ alkylcarbonyl, arylcarbonyl, heteroarylcarbonyl, $C_{1-6}$ alkoxycarbonyl, aryloxycarbonyl, heteroaryloxycarbonyl, carbamoylamino, wherein the carbamoylamino is unsubstituted or substituted with 1 to 2 $C_{1-6}$ alkyls, aryls, or heteroaryls, $C_{1-6}$ alkoxycarbonylamino, aryloxycarbonylamino, heteroaryloxycarbonylamino, $C_{1-6}$ alkylcarbonylamino, arylcarbonylamino, heteroarylcarbonylamino, aryl, wherein the aryl is unsubstituted or substituted with $C_{1-6}$ alkoxy, heteroaryl, aryloxy, heteroaryloxy, aralkyl, heteroaralkyl, aralkyloxy, and heteroaralkyloxy;

$R^3$ represents a hydrogen atom; and $M_1$, together with $M_2$, $M_3$ or $M_4$, forms —$CH_2$— or —$CH_2$—$CH_2$—, wherein when $M_2$, $M_3$ or $M_4$ do not form —$CH_2$— or —$CH_2$—$CH_2$—, $M_2$, $M_3$ or $M_4$ are each independently selected from the group consisting of hydrogen, $C_{1-6}$ alkyl and halo $C_{1-6}$ alkyl.

2. The compound or the pharmaceutically acceptable salt thereof according to claim 1, wherein $R^1$ is $C_{1-6}$ alkyl, $C_{3-8}$ cycloalkyl, aryl, or heteroaryl, and wherein the $C_{1-6}$ alkyl, the $C_{3-8}$ cycloalkyl, the aryl, and the heteroaryl are each unsubstituted or substituted with a substituent selected from the group consisting of halogen, $C_{1-6}$ alkyl, and $C_{1-6}$ alkoxy.

3. The compound or the pharmaceutically acceptable salt thereof according to claim 1, wherein $R^1$ is one of propyl, isopropyl, butyl, isobutyl, cyclopropyl, phenyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-methoxyphenyl, 3-methoxyphenyl, 4-methoxyphenyl, pyridin-2-yl, pyridin-3-yl, pyridin-4-yl, pyrimidin-2-yl, pyrazin-2-yl, pyridazin-3-yl, 2-thienyl, 3-thienyl, 1-methyl-1H-imidazol-4-yl, 5-methyl-1,3,4-thiadiazol-2-yl, 1,3-thiazol-2-yl, 1,3-oxazol-2-yl, and 1,3,4-thiadiazol-2-yl.

4. The compound or the pharmaceutically acceptable salt thereof according to claim 1, wherein $R^2$ is phenyl or heteroaryl, and wherein the phenyl and the heteroaryl are each unsubstituted or substituted with a substituent selected from the group consisting of halogen, $C_{1-6}$ alkyl, halo $C_{1-6}$ alkyl, $C_{1-6}$ alkoxy, $C_{3-6}$ cycloalkyl, aryl, aralkyl, and aralkyloxy.

5. The compound or the pharmaceutically acceptable salt thereof according to claim 1, wherein $R^2$ is one of phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-isopropylphenyl, 3-isopropylphenyl, 4-isopropylphenyl, 2-isopropoxyphenyl, 3-isopropoxyphenyl, 4-isopropoxyphenyl, 2-benzylphenyl, 3-benzylphenyl, 4-benzylphenyl, 2-benzyloxyphenyl, 3-benzyloxyphenyl, 4-benzyloxyphenyl, 5-isopropoxyphenylpyridin-2-yl, 6-isopropoxyphenylpyridin-3-yl, 5-isopropoxypyrimidin-2-yl, 3-methoxypyridin-2-yl, 3-cyclopropyl-1H-pyrazol-5-yl, and 5-isopropoxy-1H-pyrazol-3-yl.

6. The compound or the pharmaceutically acceptable salt thereof according to claim 1, wherein $M_1$, together with $M_3$, forms —$CH_2$— or —$CH_2$—$CH_2$—, and $M_2$ and $M_4$ independently represent a hydrogen atom, or $C_{1-6}$ alkyl unsubstituted or substituted with halogen.

7. The compound or the pharmaceutically acceptable salt thereof according to claim 6, wherein $M_1$, together with $M_3$, forms —$CH_2$—$CH_2$—, and $M_2$ and $M_4$ each represent a hydrogen atom.

8. The compound or the pharmaceutically acceptable salt thereof according to claim 1, wherein $M_1$, together with $M_2$, forms —$CH_2$— or —$CH_2$—$CH_2$—, and $M_3$ and $M_4$ independently represent a hydrogen atom, or $C_{1-6}$ alkyl optionally substituted with halogen.

9. The compound or the pharmaceutically acceptable salt thereof according to claim 8, wherein $M_1$, together with $M_2$, forms —$CH_2$—$CH_2$—, and $M_3$ and $M_4$ each represent a hydrogen atom.

10. A compound or the pharmaceutically acceptable salt thereof selected from the group consisting of:

(1R,4S,6R**)-N-(4-isopropoxyphenyl)-2-[(1-methyl-1H-imidazol-4-yl)sulfonyl]-2-azabicyclo[2.2.2]octane-6-carboxamide;

(1S,4R,6S**)-N-(4-isopropoxyphenyl)-2-[(1-methyl-1H-imidazol-4-yl)sulfonyl]-2-azabicyclo[2.2.2]octane-6-carboxamide;

(1R*,4S*,6R*)-2-(butylsulfonyl)-N-(3-cyclopropyl-1H-pyrazol-5-yl)-2-azabicyclo[2.2.2]octane-6-carboxamide;

(1R*,4S*,6R*)-N-(5-isopropoxypyridin-2-yl)-2-(pyridin-2-ylsulfonyl)-2-azabicyclo[2.2.2]octane-6-carboxamide;

(1R,4S,6R**)-N-(5-isopropoxypyridin-2-yl)-2-[(1-methyl-1H-imidazol-4-yl)sulfonyl]-2-azabicyclo[2.2.2]octane-6-carboxamide;

(1R*,4S*,6R*)-N-(5-isopropoxyphenyl-2-yl)-2-(phenylsulfonyl)-2-azabicyclo[2.2.2]octane-6-carboxamide;

(1R*,4S*,6R*)-N-(5-isopropoxypyridin-2-yl)-2-(phenylsulfonyl)-2-azabicyclo[2.2.2]octane-6-carboxamide;

(1S,4R,6S**)-N-(5-isopropoxypyridin-2-yl)-2-[(1-methyl-1H-imidazol-4-yl)sulfonyl]-2-azabicyclo[2.2.2]octane-6-carboxamide;

(1R*,4S*,6R*)-N-(5-isopropoxy-1H-pyrazol-3-yl)-2-[(1-methyl-1H-imidazol-4-yl)sulfonyl]-2-azabicyclo[2.2.2]octane-6-carboxamide.

11. A pharmaceutical composition, which comprises the compound or the pharmaceutically acceptable salt thereof of any one of claim 1.

* * * * *